(12) United States Patent
Garrity et al.

(10) Patent No.: US 9,986,740 B2
(45) Date of Patent: Jun. 5, 2018

(54) METHODS OF IDENTIFYING INSECT-TRPA1 MODULATORS

(71) Applicant: BRANDEIS UNIVERSITY, Waltham, MA (US)

(72) Inventors: Paul Garrity, Waltham, MA (US); Kyeongjin Kang, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days. days.

(21) Appl. No.: 15/276,682

(22) Filed: Sep. 26, 2016

(65) Prior Publication Data

US 2017/0006871 A1    Jan. 12, 2017

Related U.S. Application Data

(62) Division of application No. 13/635,494, filed as application No. PCT/US2011/028853 on Mar. 17, 2011, now Pat. No. 9,488,640.

(60) Provisional application No. 61/314,905, filed on Mar. 17, 2010.

(51) Int. Cl.
| | |
|---|---|
| G01N 33/50 | (2006.01) |
| A01N 43/36 | (2006.01) |
| A01N 35/10 | (2006.01) |
| A01N 47/48 | (2006.01) |
| G01N 35/10 | (2006.01) |
| G01N 33/68 | (2006.01) |
| A23K 50/90 | (2016.01) |
| A01N 35/02 | (2006.01) |

(52) U.S. Cl.
CPC ............ *A01N 47/48* (2013.01); *A01N 35/02* (2013.01); *A01N 43/36* (2013.01); *A23K 50/90* (2016.05); *G01N 33/5008* (2013.01); *G01N 33/5085* (2013.01); *G01N 33/6872* (2013.01); *G01N 35/10* (2013.01); *G01N 2333/43552* (2013.01); *G01N 2333/43573* (2013.01); *G01N 2333/705* (2013.01); *G01N 2500/02* (2013.01)

(58) Field of Classification Search
CPC .......... A61K 2800/782; A61K 49/0008; C07K 14/705; C07K 14/43581; G01N 2333/43552; G01N 2333/705; G01N 33/5017; G01N 33/5085; G01N 33/687; G01N 2500/02; G01N 33/50; A01K 2227/706; A01K 2267/03; A01K 67/0339; A01N 35/02; A01N 35/10
See application file for complete search history.

(56) References Cited

U.S. PATENT DOCUMENTS

2010/0247480 A1* 9/2010 Kupfer .................. A01N 25/006
                                                                        424/84

FOREIGN PATENT DOCUMENTS

WO    WO 2008070612 A2 *   6/2008 ........... A01N 25/006
WO         2009152261 A1  12/2009

OTHER PUBLICATIONS

Cheng, SS et al "Chemical Composition and Mosquito Larvicidal Activity of Essential Oils from Leaves of Different Cinnamomum osmophloeum Provenances" J Agric Food Chem, 2004,52(14),4395-4400. doi:10.1021/jf0497152.*
Broad Institute of Harvard and MIT, <http://www.broadinstitute.org/chembio/platform/screening/compound_%20libraries/index.htm>, 2015 (accessed online Nov. 17, 2015), 1 page.
Xiao, et al., "Identification of Transmembrane Domain 5 as a Critical Molecular Determinant of Menthol Sensitivity in Mammalian TRPA1 Channels", J. Neurosci., 2008, 28(39), p. 9640-9651 and supplemental data (12 pages), DOI: 10, 1523/JNEUROSCI.272-08, 2008.
NCBI-NLM "Transient Receptor Potential Cation Channel subfamily A member 1 [*Homo sapiens*]", NCBI Reference Sequence: NP_0156282, NCBI Protein Database, Mar. 15, 2015 (accessioned Oct. 24, 2006), 5 pages.
Stotz, S.C., et al., "Citral Sensing by TRANSient Receptor Potential Channels in Dorsal Root Ganglion Neurons," PLoS One, 2008, vol. 3, No. 5, article e2082, pp. 1-14 (doi:10.1371/journal.pone.0002082).
Al-Anzi, B. et al., "Response of *Drosophila* to wasabi is medicated by painless, the fly homolog of mammalian TRPA 1/ANKTM1", Curr. Biol. 16: 1034-1040 (2006).
Bandell, M. et al., "Noxious cold ion channel TRPA1 is activated by pungent compounds and bradykinin," Neuron, 41: 849-857 (2004).
Bautista, D.M., et al., "TRPA1 Mediates the Inflammatory Actions of Environmental Irritants and Proalgesic Agents," Cell, 124: 1269-1282 (2006).
Bessac, B.F., et al., "Breaktaking TRP Channels: TRPA1 and TRPV1 in Airway Chemosensation and Reflex Control," Physiology (Bethesda) 23: 360-370 (2008).
Dunipace, L. et al., "Spatially restriction expression of candidate taste receptors in the *Drosophilia* gustatory system," Curr. Bio., 11: 822-835 (2001).
Gendre, N. et al., "Integration of comple larval chemosensory organs into the adult nervous system of *Dropsophilia*," Development, 131: 83-92 (2004).
Hamada, F. N. et al., "An Internal thermal sensor controlling temperatures preference in *Drosphilia*," Nature, 454: 217-220 (2008).
Hinman, A. et al., "TRP channel activation by reversible covalent modification," Pro Natl Acad Sci U.S.A., 103: 19564-19568 (2006).

(Continued)

*Primary Examiner* — Christopher R Tate
*Assistant Examiner* — Aaron J Kosar
(74) *Attorney, Agent, or Firm* — Melissa Hunter-Ensor; Leslie Serunian; Greenberg Traurig, LLP

(57) ABSTRACT

The invention provides a screening method for identifying an insect-specific TRPA1 modulator by comparing modulation of an insect TRPA1 and a mammalian TRPA1. The invention further provides method of insect control by applying to an insect a insect-specific TRPA1 modulator identified by the screening method.

10 Claims, 18 Drawing Sheets

(56) References Cited

OTHER PUBLICATIONS

Jordt, S.E., et al., "Mustard oils and cannabinoids excite sensory nerves fibres through the TRP channel ANKTM1," Nature, 427; 260-265 (2004).
Kindt, K. S. et al., Caenorhabditis elegans TRPA-1 functions in mechanosensation, Nat Neurosci 10(5): 568-577 (2007).
Kwan, K. Y. et al., "TRPA1 Contributes to Coid, Mechanical, and Chemical Nociception but Is Not Essential for Hair-Cell Transduction," Neuron 50: 277-289 (2006).
Macpherson, L. J. et al., "Noxious compounds activate TRPA1 ion channels through covalent modification of cysteines," Nature, 445: 541-545 (2007).
Pulver, S.R. et al., "Temporal Dynamics of Neuronal Activation by Channelrhodopsin-2 and TRPA1 Determine Behavioral Output in Drosophila Larvae," J. Neurophysiol., 101, 3075-3088 (2009).
Rosenzweig, M. et al., "The Drophila orthology of vertabrae TRPA1 regulates themotaxis," Genes Dev. 19: 419-424 (2005).
Sokabe, T. et al., Drosphila Painless is a Ca2+-requiring channel activated by Noxious heat, J. Neurosci 28: 9929-9938 (2008).
Talavera, K. et al.I "Nicotine activates the chemosensory cation channel TRPA1," Nat. Neurosci, 12: 1293-1299 (2009).
Thorne, N. et al., "Taste perception and coding in *Drosphilia*," Curr Biol 14; 1065-1079 (2004).
Tracey, W.D. et al., "Painless, a *Drosphila* gene essential for nociception," Cell, 113: 261-273 (2003).
Viswanath, V. et al., "Opposite thermosensor in fruitfly and mouse," Nature, 423: 822-823 (2003).
Wang, Z. et al., "Taste representations in the *Drosphilia* brain," Cell, 117: 981-991 (2004).
Xiao, B. et al., "Identification of transmembrane domain 5 as critical molecular determinant of menthol sensitivity in mammalian TRPA1 channels," J. Neurosci, 28: 9640-95651 (2008).
NCBI-NLM "Transcient Receptor Potential Cation Channel A1 Ortholog, Isoform J [*Drosphilia melanogaster*]", NCBI Reference Sequence: NP_001097554.4, NCBI Protein Database, Aug. 5, 2014, 5 pages.
NCBI-NLM "Transcient Receptor Potential Cation Channel A1 Ortholog, Isoform J [*Drosphilia melanogaster*]", NCBI Reference Sequence: NP_001097554.3, NCBI Protein Database, May 9, 2012, 3 pages.
Rosenzweig, M., "Distinct TRP channels are required for warm and cool avoidance in *Drosphila melangaster*," Pro Natl. Aca. Sci. USA, 105: 14668-14673 (2008).

* cited by examiner

SEQUENCE LISTING

```
<160> NUMBER OF SEQ ID NOS: 21

<210> SEQ ID NO 1
<211> LENGTH: 1295
<212> TYPE: PRT
<213> ORGANISM: Drosophila melanogaster

<400> SEQUENCE: 1

Met Pro Lys Leu Tyr Asn Gly Val Tyr Ser Gly Gln Cys Gly Ala Leu
1               5                   10                  15

Ser Pro Pro Asp Leu Met Glu Ala Gln Pro Lys Leu Leu Pro Lys Pro
            20                  25                  30

Arg Ser Asn Ser Ser Gly Ser Thr Gly Arg Asn Ser Lys Tyr Trp Ile
        35                  40                  45

Phe Ser Met Ile Ile Glu Arg Ser Ala Gly Pro Lys Arg Ile Glu Ile
    50                  55                  60
```

```
Asp Gly Asp Asp Ala Asp Thr Pro Leu Glu Ala Ile Leu Pro Ala Glu
 65                  70                  75                  80

Pro Pro Ala Glu Val Cys Leu Leu Arg Asp Ser Pro Phe Arg Ile Leu
                 85                  90                  95

Arg Ser Thr Met Thr Ser Gly Asp Lys Glu Thr Pro Lys Arg Glu Asp
            100                 105                 110

Phe Ala Ser Ala Leu Arg Phe Leu Met Gly Gly Cys Ala Arg Glu Pro
        115                 120                 125

Glu Met Thr Ala Met Ala Pro Leu Asn Leu Pro Lys Lys Trp Ala Arg
    130                 135                 140

Ile Leu Arg Met Ser Ser Thr Pro Lys Ile Pro Ile Val Asp Tyr Leu
145                 150                 155                 160

Glu Ala Ala Glu Ser Gly Asn Leu Asp Asp Phe Lys Arg Leu Phe Met
                165                 170                 175

Ala Asp Asn Ser Arg Ile Ala Leu Lys Asp Ala Lys Gly Arg Thr Ala
            180                 185                 190

Ala His Gln Ala Ala Arg Asn Arg Val Asn Ile Leu Arg Tyr Ile
        195                 200                 205

Arg Asp Gln Asn Gly Asp Phe Asn Ala Lys Asp Asn Ala Gly Asn Thr
210                 215                 220

Pro Leu His Ile Ala Val Glu Ser Asp Ala Tyr Asp Ala Leu Asp Tyr
225                 230                 235                 240

Leu Leu Ser Ile Pro Val Asp Thr Gly Val Leu Asn Glu Lys Lys Gln
                245                 250                 255

Ala Pro Val His Leu Ala Thr Glu Leu Asn Lys Val Lys Ser Leu Arg
            260                 265                 270

Val Met Gly Gln Tyr Arg Asn Val Ile Asp Ile Gln Gln Gly Gly Glu
        275                 280                 285

His Gly Arg Thr Ala Leu His Leu Ala Ala Ile Tyr Asp His Glu Glu
    290                 295                 300

Cys Ala Arg Ile Leu Ile Thr Glu Phe Asp Ala Cys Pro Arg Lys Pro
305                 310                 315                 320

Cys Asn Asn Gly Tyr Tyr Pro Ile His Glu Ala Ala Lys Asn Ala Ser
                325                 330                 335

Ser Lys Thr Met Glu Val Phe Phe Gln Trp Gly Glu Gln Arg Gly Cys
            340                 345                 350

Thr Arg Glu Glu Met Ile Ser Phe Tyr Asp Ser Glu Gly Asn Val Pro
        355                 360                 365

Leu His Ser Ala Val His Gly Gly Asp Ile Lys Ala Val Glu Leu Cys
    370                 375                 380

Leu Lys Ser Gly Ala Lys Ile Ser Thr Gln His Asp Leu Ser Thr
385                 390                 395                 400

Pro Val His Leu Ala Cys Ala Gln Gly Ala Ile Asp Ile Val Lys Leu
                405                 410                 415

Met Phe Glu Met Gln Pro Met Glu Lys Arg Leu Cys Leu Ser Cys Thr
            420                 425                 430

Asp Val Gln Lys Met Thr Pro Leu His Cys Ala Ser Met Phe Asp His
        435                 440                 445

Pro Asp Ile Val Ser Tyr Leu Val Ala Glu Gly Ala Asp Ile Asn Ala
    450                 455                 460

Leu Asp Lys Glu His Arg Ser Pro Leu Leu Ala Ala Ser Arg Ser
465                 470                 475                 480

Gly Trp Lys Thr Val His Leu Leu Ile Arg Leu Gly Ala Cys Ile Ser
```

```
                        485                 490                 495
Val Lys Asp Ala Ala Arg Asn Val Leu His Phe Val Ile Met Asn
                    500                 505                 510

Gly Gly Arg Leu Thr Asp Phe Ala Glu Gln Val Ala Asn Cys Gln Thr
                515                 520                 525

Gln Ala Gln Leu Lys Leu Leu Leu Asn Glu Lys Asp Ser Met Gly Cys
        530                 535                 540

Ser Pro Leu His Tyr Ala Ser Arg Asp Gly His Ile Arg Ser Leu Glu
545                 550                 555                 560

Asn Leu Ile Arg Leu Gly Ala Cys Ile Asn Leu Lys Asn Asn Asn Asn
                565                 570                 575

Glu Ser Pro Leu His Phe Ala Ala Arg Tyr Gly Arg Tyr Asn Thr Val
                580                 585                 590

Arg Gln Leu Leu Asp Ser Glu Lys Gly Ser Phe Ile Ile Asn Glu Ser
            595                 600                 605

Asp Gly Ala Gly Met Thr Pro Leu His Ile Ser Ser Gln Gln Gly His
        610                 615                 620

Thr Arg Val Val Gln Leu Leu Leu Asn Arg Gly Ala Leu Leu His Arg
625                 630                 635                 640

Asp His Thr Gly Arg Asn Pro Leu Gln Leu Ala Ala Met Ser Gly Tyr
                645                 650                 655

Thr Glu Thr Ile Glu Leu Leu His Ser Val His Ser His Leu Leu Asp
                660                 665                 670

Gln Val Asp Lys Asp Gly Asn Thr Ala Leu His Leu Ala Thr Met Glu
            675                 680                 685

Asn Lys Pro His Ala Ile Ser Val Leu Met Ser Met Gly Cys Lys Leu
        690                 695                 700

Val Tyr Asn Val Leu Asp Met Ser Ala Ile Asp Tyr Ala Ile Tyr Tyr
705                 710                 715                 720

Lys Tyr Pro Glu Ala Ala Leu Ala Met Val Thr His Glu Glu Arg Ala
                725                 730                 735

Asn Glu Val Met Ala Leu Arg Ser Asp Lys His Pro Cys Val Thr Leu
                740                 745                 750

Ala Leu Ile Ala Ser Met Pro Lys Val Phe Glu Ala Val Gln Asp Lys
            755                 760                 765

Cys Ile Thr Lys Ala Asn Cys Lys Lys Asp Ser Lys Ser Phe Tyr Ile
        770                 775                 780

Lys Tyr Ser Phe Trp Pro Tyr Gln Lys Thr Pro Glu Gln Ile Glu Ala
785                 790                 795                 800

Lys Arg Lys Glu Phe Asn Asp Pro Lys Trp Arg Pro Ala Pro Leu Ala
                805                 810                 815

Val Val Asn Thr Met Val Thr His Gly Arg Val Glu Leu Leu Ala His
                820                 825                 830

Pro Leu Ser Gln Lys Tyr Leu Gln Met Lys Trp Asn Ser Tyr Gly Lys
            835                 840                 845

Tyr Phe His Leu Ala Asn Leu Leu Ile Tyr Ser Ile Phe Leu Val Phe
        850                 855                 860

Val Thr Ile Tyr Ser Ser Leu Met Met Asn Asn Ile Glu Leu Lys Ala
865                 870                 875                 880

Gly Asp Asn Lys Thr Met Ser Gln Tyr Cys Asn Met Gly Trp Glu Gln
                885                 890                 895

Leu Thr Met Asn Leu Ser Gln Asn Pro Ser Val Ala Ser Gln Ile Arg
                900                 905                 910
```

-continued

```
Leu Asp Ser Cys Glu Glu Arg Ile Asn Arg Thr Thr Ala Ile Leu Phe
        915                 920                 925

Cys Ala Val Val Ile Val Val Tyr Ile Leu Leu Asn Ser Met Arg Glu
        930                 935                 940

Leu Ile Gln Ile Tyr Gln Gln Lys Leu His Tyr Ile Leu Glu Thr Val
945                 950                 955                 960

Asn Leu Ile Ser Trp Val Leu Tyr Ile Ser Ala Leu Val Met Val Thr
                965                 970                 975

Pro Ala Phe Gln Pro Asp Gly Gly Ile Asn Thr Ile His Tyr Ser Ala
            980                 985                 990

Ala Ser Ile Ala Val Phe Leu Ser Trp Phe Arg Leu Leu Leu Phe Leu
            995                 1000                1005

Gln Arg Phe Asp Gln Val Gly Ile Tyr Val Val Met Phe Leu Glu
    1010                1015                1020

Ile Leu Gln Thr Leu Ile Lys Val Leu Met Val Phe Ser Ile Leu
    1025                1030                1035

Ile Ile Ala Phe Gly Leu Ala Phe Tyr Ile Leu Leu Ser Lys Ile
    1040                1045                1050

Ile Asp Pro Gln Pro Asn His Leu Ser Phe Ser Asn Ile Pro Met
    1055                1060                1065

Ser Leu Leu Arg Thr Phe Ser Met Met Leu Gly Glu Leu Asp Phe
    1070                1075                1080

Val Gly Thr Tyr Val Asn Thr Tyr Tyr Arg Asp Gln Leu Lys Val
    1085                1090                1095

Pro Met Thr Ser Phe Leu Ile Leu Ser Val Phe Met Ile Leu Met
    1100                1105                1110

Pro Ile Leu Leu Met Asn Leu Leu Ile Gly Leu Ala Val Gly Asp
    1115                1120                1125

Ile Glu Ser Val Arg Arg Asn Ala Gln Leu Lys Arg Leu Ala Met
    1130                1135                1140

Gln Val Val Leu His Thr Glu Leu Glu Arg Lys Leu Pro His Val
    1145                1150                1155

Trp Leu Gln Arg Val Asp Lys Met Glu Leu Ile Glu Tyr Pro Asn
    1160                1165                1170

Glu Thr Lys Cys Lys Leu Gly Phe Cys Asp Phe Ile Leu Arg Lys
    1175                1180                1185

Trp Phe Ser Asn Pro Phe Thr Glu Asp Ser Ser Met Asp Val Ile
    1190                1195                1200

Ser Phe Asp Asn Asn Asp Tyr Ile Asn Ala Glu Leu Glu Arg
    1205                1210                1215

Gln Arg Arg Lys Leu Arg Asp Ile Ser Arg Met Leu Glu Gln Gln
    1220                1225                1230

His His Leu Val Arg Leu Ile Val Gln Lys Met Glu Ile Lys Thr
    1235                1240                1245

Glu Ala Asp Asp Val Asp Glu Gly Ile Ser Pro Asn Glu Leu Arg
    1250                1255                1260

Ser Val Val Gly Leu Arg Ser Ala Gly Gly Asn Arg Trp Asn Ser
    1265                1270                1275

Pro Arg Val Arg Asn Lys Leu Arg Ala Ala Leu Ser Phe Asn Lys
    1280                1285                1290

Ser Met
    1295
```

<210> SEQ ID NO 2
<211> LENGTH: 1296
<212> TYPE: PRT
<213> ORGANISM: Drosophila melanogaster

<400> SEQUENCE: 2

```
Met Pro Lys Leu Tyr Asn Gly Val Tyr Ser Gly Gln Cys Gly Ala Leu
1               5                   10                  15

Ser Pro Pro Asp Leu Met Glu Ala Gln Pro Lys Leu Leu Pro Lys Pro
            20                  25                  30

Arg Ser Asn Ser Ser Gly Ser Thr Gly Arg Asn Ser Lys Tyr Trp Ile
        35                  40                  45

Phe Ser Met Ile Ile Glu Arg Ser Ala Gly Pro Lys Arg Ile Glu Ile
    50                  55                  60

Asp Gly Asp Asp Ala Asp Thr Pro Leu Glu Ala Ile Leu Pro Ala Glu
65                  70                  75                  80

Pro Pro Ala Glu Val Cys Leu Leu Arg Asp Ser Pro Phe Arg Ile Leu
                85                  90                  95

Arg Ser Thr Met Thr Ser Gly Asp Lys Glu Thr Pro Lys Arg Glu Asp
            100                 105                 110

Phe Ala Ser Ala Leu Arg Phe Leu Met Gly Gly Cys Ala Arg Glu Pro
        115                 120                 125

Glu Met Thr Ala Met Ala Pro Leu Asn Leu Pro Lys Lys Trp Ala Arg
    130                 135                 140

Ile Leu Arg Met Ser Ser Thr Pro Lys Ile Pro Ile Val Asp Tyr Leu
145                 150                 155                 160

Glu Ala Ala Glu Ser Gly Asn Leu Asp Asp Phe Lys Arg Leu Phe Met
                165                 170                 175

Ala Asp Asn Ser Arg Ile Ala Leu Lys Asp Ala Lys Gly Arg Thr Ala
            180                 185                 190

Ala His Gln Ala Ala Arg Asn Arg Val Asn Ile Leu Arg Tyr Ile
        195                 200                 205

Arg Asp Gln Asn Gly Asp Phe Asn Ala Lys Asp Asn Ala Gly Asn Thr
    210                 215                 220

Pro Leu His Ile Ala Val Glu Ser Asp Ala Tyr Asp Ala Leu Asp Tyr
225                 230                 235                 240

Leu Leu Ser Ile Pro Val Asp Thr Gly Val Leu Asn Glu Lys Lys Gln
                245                 250                 255

Ala Pro Val His Leu Ala Thr Glu Leu Asn Lys Val Lys Ser Leu Arg
            260                 265                 270

Val Met Gly Gln Tyr Arg Asn Val Ile Asp Ile Gln Gln Gly Gly Glu
        275                 280                 285

His Gly Arg Thr Ala Leu His Leu Ala Ala Ile Tyr Asp His Glu Glu
    290                 295                 300

Cys Ala Arg Ile Leu Ile Thr Glu Phe Asp Ala Cys Pro Arg Lys Pro
305                 310                 315                 320

Cys Asn Asn Gly Tyr Tyr Pro Ile His Glu Ala Ala Lys Asn Ala Ser
                325                 330                 335

Ser Lys Thr Met Glu Val Phe Phe Gln Trp Gly Glu Gln Arg Gly Cys
            340                 345                 350

Thr Arg Glu Glu Met Ile Ser Phe Tyr Asp Ser Glu Gly Asn Val Pro
        355                 360                 365

Leu His Ser Ala Val His Gly Gly Asp Ile Lys Ala Val Glu Leu Cys
    370                 375                 380
```

```
Leu Lys Ser Gly Ala Lys Ile Ser Thr Gln Gln His Asp Leu Ser Thr
385                 390                 395                 400

Pro Val His Leu Ala Cys Ala Gln Gly Ala Ile Asp Ile Val Lys Leu
                405                 410                 415

Met Phe Glu Met Gln Pro Met Glu Lys Arg Leu Cys Leu Ser Cys Thr
            420                 425                 430

Asp Val Gln Lys Met Thr Pro Leu His Cys Ala Ser Met Phe Asp His
        435                 440                 445

Pro Asp Ile Val Ser Tyr Leu Val Ala Glu Gly Ala Asp Ile Asn Ala
    450                 455                 460

Leu Asp Lys Glu His Arg Ser Pro Leu Leu Leu Ala Ala Ser Arg Ser
465                 470                 475                 480

Gly Trp Lys Thr Val His Leu Leu Ile Arg Leu Gly Ala Cys Ile Ser
                485                 490                 495

Val Lys Asp Ala Ala Ala Arg Asn Val Leu His Phe Val Ile Met Asn
            500                 505                 510

Gly Gly Arg Leu Thr Asp Phe Ala Glu Gln Val Ala Asn Cys Gln Thr
        515                 520                 525

Gln Ala Gln Leu Lys Leu Leu Leu Asn Glu Lys Asp Ser Met Gly Cys
    530                 535                 540

Ser Pro Leu His Tyr Ala Ser Arg Asp Gly His Ile Arg Ser Leu Glu
545                 550                 555                 560

Asn Leu Ile Arg Leu Gly Ala Cys Ile Asn Leu Lys Asn Asn Asn Asn
                565                 570                 575

Glu Ser Pro Leu His Phe Ala Ala Arg Tyr Gly Arg Tyr Asn Thr Val
            580                 585                 590

Arg Gln Leu Leu Asp Ser Glu Lys Gly Ser Phe Ile Ile Asn Glu Ser
        595                 600                 605

Asp Gly Ala Gly Met Thr Pro Leu His Ile Ser Ser Gln Gln Gly His
    610                 615                 620

Thr Arg Val Val Gln Leu Leu Leu Asn Arg Gly Ala Leu Leu His Arg
625                 630                 635                 640

Asp His Thr Gly Arg Asn Pro Leu Gln Leu Ala Ala Met Ser Gly Tyr
                645                 650                 655

Thr Glu Thr Ile Glu Leu Leu His Ser Val His Ser His Leu Leu Asp
            660                 665                 670

Gln Val Asp Lys Asp Gly Asn Thr Ala Leu His Leu Ala Thr Met Glu
        675                 680                 685

Asn Lys Pro His Ala Ile Ser Val Leu Met Ser Met Gly Cys Lys Leu
    690                 695                 700

Val Tyr Asn Val Leu Asp Met Ser Ala Ile Asp Tyr Ala Ile Tyr Tyr
705                 710                 715                 720

Lys Tyr Pro Glu Ala Ala Leu Ala Met Val Thr His Glu Glu Arg Ala
                725                 730                 735

Asn Glu Val Met Ala Leu Arg Ser Asp Lys His Pro Cys Val Thr Leu
            740                 745                 750

Ala Leu Ile Ala Ser Met Pro Lys Val Phe Glu Ala Val Gln Asp Lys
        755                 760                 765

Cys Ile Thr Lys Ala Asn Cys Lys Lys Asp Ser Lys Ser Phe Tyr Ile
    770                 775                 780

Lys Tyr Ser Phe Ala Phe Leu Gln Cys Pro Phe Met Phe Ala Lys Ile
785                 790                 795                 800
```

```
Asp Glu Lys Thr Gly Glu Ser Ile Thr Thr Ala Ser Pro Ile Pro Leu
            805                 810                 815

Pro Ala Leu Asn Thr Met Val Thr His Gly Arg Val Glu Leu Leu Ala
            820                 825                 830

His Pro Leu Ser Gln Lys Tyr Leu Gln Met Lys Trp Asn Ser Tyr Gly
            835                 840                 845

Lys Tyr Phe His Leu Ala Asn Leu Leu Ile Tyr Ser Ile Phe Leu Val
            850                 855                 860

Phe Val Thr Ile Tyr Ser Ser Leu Met Met Asn Asn Ile Glu Leu Lys
865                 870                 875                 880

Ala Gly Asp Asn Lys Thr Met Ser Gln Tyr Cys Asn Met Gly Trp Glu
            885                 890                 895

Gln Leu Thr Met Asn Leu Ser Gln Asn Pro Ser Val Ala Ser Gln Ile
            900                 905                 910

Arg Leu Asp Ser Cys Glu Glu Arg Ile Asn Arg Thr Thr Ala Ile Leu
            915                 920                 925

Phe Cys Ala Val Val Ile Val Val Tyr Ile Leu Leu Asn Ser Met Arg
            930                 935                 940

Glu Leu Ile Gln Ile Tyr Gln Gln Lys Leu His Tyr Ile Leu Glu Thr
945                 950                 955                 960

Val Asn Leu Ile Ser Trp Val Leu Tyr Ile Ser Ala Leu Val Met Val
            965                 970                 975

Thr Pro Ala Phe Gln Pro Asp Gly Gly Ile Asn Thr Ile His Tyr Ser
            980                 985                 990

Ala Ala Ser Ile Ala Val Phe Leu Ser Trp Phe Arg Leu Leu Leu Phe
            995                 1000                1005

Leu Gln Arg Phe Asp Gln Val Gly Ile Tyr Val Val Met Phe Leu
            1010                1015                1020

Glu Ile Leu Gln Thr Leu Ile Lys Val Leu Met Val Phe Ser Ile
1025                1030                1035

Leu Ile Ile Ala Phe Gly Leu Ala Phe Tyr Ile Leu Leu Ser Lys
1040                1045                1050

Ile Ile Asp Pro Gln Pro Asn His Leu Ser Phe Ser Asn Ile Pro
1055                1060                1065

Met Ser Leu Leu Arg Thr Phe Ser Met Met Leu Gly Glu Leu Asp
1070                1075                1080

Phe Val Gly Thr Tyr Val Asn Thr Tyr Tyr Arg Asp Gln Leu Lys
1085                1090                1095

Val Pro Met Thr Ser Phe Leu Ile Leu Ser Val Phe Met Ile Leu
1100                1105                1110

Met Pro Ile Leu Leu Met Asn Leu Leu Ile Gly Leu Ala Val Gly
1115                1120                1125

Asp Ile Glu Ser Val Arg Arg Asn Ala Gln Leu Lys Arg Leu Ala
1130                1135                1140

Met Gln Val Val Leu His Thr Glu Leu Glu Arg Lys Leu Pro His
1145                1150                1155

Val Trp Leu Gln Arg Val Asp Lys Met Glu Leu Ile Glu Tyr Pro
1160                1165                1170

Asn Glu Thr Lys Cys Lys Leu Gly Phe Cys Asp Phe Ile Leu Arg
1175                1180                1185

Lys Trp Phe Ser Asn Pro Phe Thr Glu Asp Ser Ser Met Asp Val
1190                1195                1200

Ile Ser Phe Asp Asn Asn Asp Asp Tyr Ile Asn Ala Glu Leu Glu
```

```
            1205                1210                1215

Arg Gln Arg Arg Lys Leu Arg Asp Ile Ser Arg Met Leu Glu Gln
        1220                1225                1230

Gln His His Leu Val Arg Leu Ile Val Gln Lys Met Glu Ile Lys
    1235                1240                1245

Thr Glu Ala Asp Asp Val Asp Glu Gly Ile Ser Pro Asn Glu Leu
        1250                1255                1260

Arg Ser Val Val Gly Leu Arg Ser Ala Gly Gly Asn Arg Trp Asn
        1265                1270                1275

Ser Pro Arg Val Arg Asn Lys Leu Arg Ala Ala Leu Ser Phe Asn
        1280                1285                1290

Lys Ser Met
        1295

<210> SEQ ID NO 3
<211> LENGTH: 1295
<212> TYPE: PRT
<213> ORGANISM: Drosophila melanogaster

<400> SEQUENCE: 3

Met Pro Lys Leu Tyr Asn Gly Val Tyr Ser Gly Gln Cys Gly Ala Leu
1               5                   10                  15

Ser Pro Pro Asp Leu Met Glu Ala Gln Pro Lys Leu Leu Pro Lys Pro
            20                  25                  30

Arg Ser Asn Ser Ser Gly Ser Thr Gly Arg Asn Ser Lys Tyr Trp Ile
        35                  40                  45

Phe Ser Met Ile Ile Glu Arg Ser Ala Gly Pro Lys Arg Ile Glu Ile
    50                  55                  60

Asp Gly Asp Asp Ala Asp Thr Pro Leu Glu Ala Ile Leu Pro Ala Glu
65                  70                  75                  80

Pro Pro Ala Glu Val Cys Leu Leu Arg Asp Ser Pro Phe Arg Ile Leu
                85                  90                  95

Arg Ser Thr Met Thr Ser Gly Asp Lys Glu Thr Pro Lys Arg Glu Asp
            100                 105                 110

Phe Ala Ser Ala Leu Arg Phe Leu Met Gly Gly Cys Ala Arg Glu Pro
        115                 120                 125

Glu Met Thr Ala Met Ala Pro Leu Asn Leu Pro Lys Lys Trp Ala Arg
    130                 135                 140

Ile Leu Arg Met Ser Ser Thr Pro Lys Ile Pro Ile Val Asp Tyr Leu
145                 150                 155                 160

Glu Ala Ala Glu Ser Gly Asn Leu Asp Asp Phe Lys Arg Leu Phe Met
                165                 170                 175

Ala Asp Asn Ser Arg Ile Ala Leu Lys Asp Ala Lys Gly Arg Thr Ala
            180                 185                 190

Ala His Gln Ala Ala Ala Arg Asn Arg Val Asn Ile Leu Arg Tyr Ile
        195                 200                 205

Arg Asp Gln Asn Gly Asp Phe Asn Ala Lys Asp Asn Ala Gly Asn Thr
    210                 215                 220

Pro Leu His Ile Ala Val Glu Ser Asp Ala Tyr Asp Ala Leu Asp Tyr
225                 230                 235                 240

Leu Leu Ser Ile Pro Val Asp Thr Gly Val Leu Asn Glu Lys Lys Gln
                245                 250                 255

Ala Pro Val His Leu Ala Thr Glu Leu Asn Lys Val Lys Ser Leu Arg
            260                 265                 270
```

```
Val Met Gly Gln Tyr Arg Asn Val Ile Asp Ile Gln Gly Gly Glu
            275                 280                 285
His Gly Arg Thr Ala Leu His Leu Ala Ala Ile Tyr Asp His Glu Glu
            290                 295                 300
Cys Ala Arg Ile Leu Ile Thr Glu Phe Asp Ala Cys Pro Arg Lys Pro
305                 310                 315                 320
Cys Asn Asn Gly Tyr Tyr Pro Ile His Glu Ala Ala Lys Asn Ala Ser
                    325                 330                 335
Ser Lys Thr Met Glu Val Phe Phe Gln Trp Gly Glu Gln Arg Gly Cys
            340                 345                 350
Thr Arg Glu Glu Met Ile Ser Phe Tyr Asp Ser Glu Gly Asn Val Pro
            355                 360                 365
Leu His Ser Ala Val His Gly Gly Asp Ile Lys Ala Val Glu Leu Cys
            370                 375                 380
Leu Lys Ser Gly Ala Lys Ile Ser Thr Gln Gln His Asp Leu Ser Thr
385                 390                 395                 400
Pro Val His Leu Ala Cys Ala Gln Gly Ala Ile Asp Ile Val Lys Leu
                    405                 410                 415
Met Phe Glu Met Gln Pro Met Glu Lys Arg Leu Cys Leu Ser Cys Thr
            420                 425                 430
Asp Val Gln Lys Met Thr Pro Leu His Cys Ala Ser Met Phe Asp His
            435                 440                 445
Pro Asp Ile Val Ser Tyr Leu Val Ala Glu Gly Ala Asp Ile Asn Ala
            450                 455                 460
Leu Asp Lys Glu His Arg Ser Pro Leu Leu Ala Ala Ser Arg Ser
465                 470                 475                 480
Gly Trp Lys Thr Val His Leu Leu Ile Arg Leu Gly Ala Cys Ile Ser
                    485                 490                 495
Val Lys Asp Ala Ala Ala Arg Asn Val Leu His Phe Val Ile Met Asn
            500                 505                 510
Gly Gly Arg Leu Thr Asp Phe Ala Glu Gln Val Ala Asn Cys Gln Thr
            515                 520                 525
Gln Ala Gln Leu Lys Leu Leu Leu Asn Glu Lys Asp Ser Met Gly Cys
            530                 535                 540
Ser Pro Leu His Tyr Ala Ser Arg Asp Gly His Ile Arg Ser Leu Glu
545                 550                 555                 560
Asn Leu Ile Arg Leu Gly Ala Cys Ile Asn Leu Lys Asn Asn Asn Asn
                    565                 570                 575
Glu Ser Pro Leu His Phe Ala Ala Arg Tyr Gly Arg Tyr Asn Thr Val
            580                 585                 590
Arg Gln Leu Leu Asp Ser Glu Lys Gly Ser Phe Ile Ile Asn Glu Ser
            595                 600                 605
Asp Gly Ala Gly Met Thr Pro Leu His Ile Ser Ser Gln Gln Gly His
            610                 615                 620
Thr Arg Val Val Gln Leu Leu Leu Asn Arg Gly Ala Leu Leu His Arg
625                 630                 635                 640
Asp His Thr Gly Arg Asn Pro Leu Gln Leu Ala Ala Met Ser Gly Tyr
                    645                 650                 655
Thr Glu Thr Ile Glu Leu Leu His Ser Val His Ser His Leu Leu Asp
            660                 665                 670
Gln Val Asp Lys Asp Gly Asn Thr Ala Leu His Leu Ala Thr Met Glu
            675                 680                 685
Asn Lys Pro His Ala Ile Ser Val Leu Met Ser Met Gly Cys Lys Leu
```

-continued

```
            690             695             700
Val Tyr Asn Val Leu Asp Met Ser Ala Ile Asp Tyr Ala Ile Tyr Tyr
705             710             715             720

Lys Tyr Pro Glu Ala Ala Leu Ala Met Val Thr His Glu Arg Ala
            725             730             735

Asn Glu Val Met Ala Leu Arg Ser Asp Lys His Pro Cys Val Thr Leu
            740             745             750

Ala Leu Ile Ala Ser Met Pro Lys Val Phe Glu Ala Val Gln Asp Lys
            755             760             765

Cys Ile Thr Lys Ala Asn Cys Lys Lys Asp Ser Lys Ser Phe Tyr Ile
            770             775             780

Lys Tyr Ser Phe Trp Pro Tyr Gln Lys Thr Pro Glu Gln Ile Glu Ala
785             790             795             800

Lys Arg Lys Glu Phe Asn Asp Pro Lys Trp Arg Pro Ala Pro Leu Ala
            805             810             815

Val Val Asn Thr Met Val Thr His Gly Arg Val Glu Leu Leu Ala His
            820             825             830

Pro Leu Ser Gln Lys Tyr Leu Gln Met Lys Trp Asn Ser Tyr Gly Lys
            835             840             845

Tyr Phe His Leu Ala Asn Leu Leu Ile Tyr Ser Ile Phe Leu Val Phe
            850             855             860

Val Thr Ile Tyr Ser Ser Leu Met Met Asn Asn Ile Glu Leu Lys Ala
865             870             875             880

Gly Asp Asn Lys Thr Met Ser Gln Tyr Cys Asn Met Gly Trp Glu Gln
            885             890             895

Leu Thr Met Asn Leu Ser Gln Asn Pro Ser Val Ala Ser Gln Ile Arg
            900             905             910

Leu Asp Ser Cys Glu Glu Arg Ile Asn Arg Thr Thr Ala Ile Leu Phe
            915             920             925

Cys Ala Val Val Ile Val Val Tyr Ile Leu Leu Asn Ser Met Arg Glu
            930             935             940

Leu Ile Gln Ile Tyr Gln Gln Lys Leu His Tyr Ile Leu Glu Thr Val
945             950             955             960

Asn Leu Ile Ser Trp Val Leu Tyr Ile Ser Ala Leu Val Met Val Thr
            965             970             975

Pro Ala Phe Gln Pro Asp Gly Ile Asn Thr Ile His Tyr Ser Ala
            980             985             990

Ala Ser Ile Ala Val Phe Leu Ser Trp Phe Arg Leu Leu Leu Phe Leu
            995             1000            1005

Gln Arg Phe Asp Gln Val Gly Ile Tyr Val Val Met Phe Leu Glu
     1010            1015            1020

Ile Leu Gln Thr Leu Ile Lys Val Leu Met Val Phe Ser Ile Leu
     1025            1030            1035

Ile Ile Ala Phe Gly Leu Ala Phe Tyr Ile Leu Leu Ser Lys Ile
     1040            1045            1050

Ile Asp Pro Gln Pro Asn His Leu Ser Phe Ser Asn Ile Pro Met
     1055            1060            1065

Ser Leu Leu Arg Thr Phe Ser Met Met Leu Gly Glu Leu Asp Phe
     1070            1075            1080

Val Gly Thr Tyr Val Asn Thr Tyr Tyr Arg Asp Gln Leu Lys Val
     1085            1090            1095

Pro Met Thr Ser Phe Leu Ile Leu Ser Val Phe Met Ile Leu Met
     1100            1105            1110
```

```
Pro Ile Leu Leu Met Asn Leu Leu Ile Gly Leu Ala Val Gly Asp
    1115                1120                1125

Ile Glu Ser Val Arg Arg Asn Ala Gln Leu Lys Arg Leu Ala Met
    1130                1135                1140

Gln Val Val Leu His Thr Glu Leu Glu Arg Lys Leu Pro His Val
    1145                1150                1155

Trp Leu Gln Arg Val Asp Lys Met Glu Leu Ile Glu Tyr Pro Asn
    1160                1165                1170

Glu Thr Lys Cys Lys Leu Gly Phe Cys Asp Phe Ile Leu Arg Lys
    1175                1180                1185

Trp Phe Ser Asn Pro Phe Thr Glu Asp Ser Ser Met Asp Val Ile
    1190                1195                1200

Ser Phe Asp Asn Asn Asp Asp Tyr Ile Asn Ala Glu Leu Glu Arg
    1205                1210                1215

Gln Arg Arg Lys Leu Arg Asp Ile Ser Arg Met Leu Glu Gln Gln
    1220                1225                1230

His His Leu Val Arg Leu Ile Val Gln Lys Met Glu Ile Lys Thr
    1235                1240                1245

Glu Ala Asp Asp Val Asp Glu Gly Ile Ser Pro Asn Glu Leu Arg
    1250                1255                1260

Ser Val Val Gly Leu Arg Ser Ala Gly Gly Asn Arg Trp Asn Ser
    1265                1270                1275

Pro Arg Val Arg Asn Lys Leu Arg Ala Ala Leu Ser Phe Asn Lys
    1280                1285                1290

Ser Met
    1295

<210> SEQ ID NO 4
<211> LENGTH: 1296
<212> TYPE: PRT
<213> ORGANISM: Drosophila melanogaster

<400> SEQUENCE: 4

Met Pro Lys Leu Tyr Asn Gly Val Tyr Ser Gly Gln Cys Gly Ala Leu
1               5                   10                  15

Ser Pro Pro Asp Leu Met Glu Ala Gln Pro Lys Leu Leu Pro Lys Pro
                20                  25                  30

Arg Ser Asn Ser Ser Gly Ser Thr Gly Arg Asn Ser Lys Tyr Trp Ile
            35                  40                  45

Phe Ser Met Ile Ile Glu Arg Ser Ala Gly Pro Lys Arg Ile Glu Ile
        50                  55                  60

Asp Gly Asp Asp Ala Asp Thr Pro Leu Glu Ala Ile Leu Pro Ala Glu
65                  70                  75                  80

Pro Pro Ala Glu Val Cys Leu Leu Arg Asp Ser Pro Phe Arg Ile Leu
                85                  90                  95

Arg Ser Thr Met Thr Ser Gly Asp Lys Glu Thr Pro Leu Arg Glu Asp
                100                 105                 110

Phe Ala Ser Ala Leu Arg Phe Leu Met Gly Gly Cys Ala Arg Glu Pro
            115                 120                 125

Glu Met Thr Ala Met Ala Pro Leu Asn Leu Pro Lys Lys Trp Ala Arg
        130                 135                 140

Ile Leu Arg Met Ser Ser Thr Pro Lys Ile Pro Ile Val Asp Tyr Leu
145                 150                 155                 160

Glu Ala Ala Glu Ser Gly Asn Leu Asp Asp Phe Lys Arg Leu Phe Met
```

```
                    165                 170                 175
Ala Asp Asn Ser Arg Ile Ala Leu Lys Asp Ala Lys Gly Arg Thr Ala
                180                 185                 190

Ala His Gln Ala Ala Arg Asn Arg Val Asn Ile Leu Arg Tyr Ile
        195                 200                 205

Arg Asp Gln Asn Gly Asp Phe Asn Ala Lys Asp Asn Ala Gly Asn Thr
        210                 215                 220

Pro Leu His Ile Ala Val Glu Ser Asp Ala Tyr Asp Ala Leu Asp Tyr
225                 230                 235                 240

Leu Leu Ser Ile Pro Val Asp Thr Gly Val Leu Asn Glu Lys Lys Gln
                245                 250                 255

Ala Pro Val His Leu Ala Thr Glu Leu Asn Lys Val Lys Ser Leu Arg
                260                 265                 270

Val Met Gly Gln Tyr Arg Asn Val Ile Asp Ile Gln Gln Gly Gly Glu
                275                 280                 285

His Gly Arg Thr Ala Leu His Leu Ala Ala Ile Tyr Asp His Glu Glu
                290                 295                 300

Cys Ala Arg Ile Leu Ile Thr Glu Phe Asp Ala Cys Pro Arg Lys Pro
305                 310                 315                 320

Cys Asn Asn Gly Tyr Tyr Pro Ile His Glu Ala Ala Lys Asn Ala Ser
                325                 330                 335

Ser Lys Thr Met Glu Val Phe Phe Gln Trp Gly Glu Gln Arg Gly Cys
                340                 345                 350

Thr Arg Glu Glu Met Ile Ser Phe Tyr Asp Ser Glu Gly Asn Val Pro
                355                 360                 365

Leu His Ser Ala Val His Gly Gly Asp Ile Lys Ala Val Glu Leu Cys
                370                 375                 380

Leu Lys Ser Gly Ala Lys Ile Ser Thr Gln Gln His Asp Leu Ser Thr
385                 390                 395                 400

Pro Val His Leu Ala Cys Ala Gln Gly Ala Ile Asp Ile Val Lys Leu
                405                 410                 415

Met Phe Glu Met Gln Pro Met Glu Lys Arg Leu Cys Leu Ser Cys Thr
                420                 425                 430

Asp Val Gln Lys Met Thr Pro Leu His Cys Ala Ser Met Phe Asp His
                435                 440                 445

Pro Asp Ile Val Ser Tyr Leu Val Ala Glu Gly Ala Asp Ile Asn Ala
                450                 455                 460

Leu Asp Lys Glu His Arg Ser Pro Leu Leu Ala Ala Ser Arg Ser
465                 470                 475                 480

Gly Trp Lys Thr Val His Leu Leu Ile Arg Leu Gly Ala Cys Ile Ser
                485                 490                 495

Val Lys Asp Ala Ala Arg Asn Val Leu His Phe Val Ile Met Asn
                500                 505                 510

Gly Gly Arg Leu Thr Asp Phe Ala Glu Gln Val Ala Asn Cys Gln Thr
                515                 520                 525

Gln Ala Gln Leu Lys Leu Leu Asn Glu Lys Asp Ser Met Gly Cys
                530                 535                 540

Ser Pro Leu His Tyr Ala Ser Arg Asp Gly His Ile Arg Ser Leu Glu
545                 550                 555                 560

Asn Leu Ile Arg Leu Gly Ala Cys Ile Asn Leu Lys Asn Asn Asn
                565                 570                 575

Glu Ser Pro Leu His Phe Ala Ala Arg Tyr Gly Arg Tyr Asn Thr Val
                580                 585                 590
```

```
Arg Gln Leu Leu Asp Ser Glu Lys Gly Ser Phe Ile Ile Asn Glu Ser
        595                 600                 605

Asp Gly Ala Gly Met Thr Pro Leu His Ile Ser Ser Gln Gln Gly His
610                 615                 620

Thr Arg Val Val Gln Leu Leu Asn Arg Gly Ala Leu Leu His Arg
625                 630                 635                 640

Asp His Thr Gly Arg Asn Pro Leu Gln Leu Ala Ala Met Ser Gly Tyr
                645                 650                 655

Thr Glu Thr Ile Glu Leu Leu His Ser Val His Ser His Leu Leu Asp
                660                 665                 670

Gln Val Asp Lys Asp Gly Asn Thr Ala Leu His Leu Ala Thr Met Glu
            675                 680                 685

Asn Lys Pro His Ala Ile Ser Val Leu Met Ser Met Gly Cys Lys Leu
690                 695                 700

Val Tyr Asn Val Leu Asp Met Ser Ala Ile Asp Tyr Ala Ile Tyr Tyr
705                 710                 715                 720

Lys Tyr Pro Glu Ala Ala Leu Ala Met Val Thr His Glu Glu Arg Ala
                725                 730                 735

Asn Glu Val Met Ala Leu Arg Ser Asp Lys His Pro Cys Val Thr Leu
                740                 745                 750

Ala Leu Ile Ala Ser Met Pro Lys Val Phe Glu Ala Val Gln Asp Lys
            755                 760                 765

Cys Ile Thr Lys Ala Asn Cys Lys Lys Asp Ser Lys Ser Phe Tyr Ile
            770                 775                 780

Lys Tyr Ser Phe Ala Phe Leu Gln Cys Pro Phe Met Phe Ala Lys Ile
785                 790                 795                 800

Asp Glu Lys Thr Gly Glu Ser Ile Thr Thr Ala Ser Pro Ile Pro Leu
                805                 810                 815

Pro Ala Leu Asn Thr Met Val Thr His Gly Arg Val Glu Leu Leu Ala
                820                 825                 830

His Pro Leu Ser Gln Lys Tyr Leu Gln Met Lys Trp Asn Ser Tyr Gly
            835                 840                 845

Lys Tyr Phe His Leu Ala Asn Leu Leu Ile Tyr Ser Ile Phe Leu Val
850                 855                 860

Phe Val Thr Ile Tyr Ser Ser Leu Met Met Asn Asn Ile Glu Leu Lys
865                 870                 875                 880

Ala Gly Asp Asn Lys Thr Met Ser Gln Tyr Cys Asn Met Gly Trp Glu
                885                 890                 895

Gln Leu Thr Met Asn Leu Ser Gln Asn Pro Ser Val Ala Ser Gln Ile
            900                 905                 910

Arg Leu Asp Ser Cys Glu Glu Arg Ile Asn Arg Thr Thr Ala Ile Leu
            915                 920                 925

Phe Cys Ala Val Val Ile Val Val Tyr Ile Leu Leu Asn Ser Met Arg
930                 935                 940

Glu Leu Ile Gln Ile Tyr Gln Gln Lys Leu His Tyr Ile Leu Glu Thr
945                 950                 955                 960

Val Asn Leu Ile Ser Trp Val Leu Tyr Ile Ser Ala Leu Val Met Val
                965                 970                 975

Thr Pro Ala Phe Gln Pro Asp Gly Gly Ile Asn Thr Ile His Tyr Ser
            980                 985                 990

Ala Ala Ser Ile Ala Val Phe Leu  Ser Trp Phe Arg Leu  Leu Leu Phe
            995                 1000                1005
```

```
Leu Gln Arg Phe Asp Gln Val Gly Ile Tyr Val Val Met Phe Leu
    1010                1015                1020

Glu Ile Leu Gln Thr Leu Ile Lys Val Leu Met Val Phe Ser Ile
    1025                1030                1035

Leu Ile Ile Ala Phe Gly Leu Ala Phe Tyr Ile Leu Leu Ser Lys
    1040                1045                1050

Ile Ile Asp Pro Gln Pro Asn His Leu Ser Phe Ser Asn Ile Pro
    1055                1060                1065

Met Ser Leu Leu Arg Thr Phe Ser Met Met Leu Gly Glu Leu Asp
    1070                1075                1080

Phe Val Gly Thr Tyr Val Asn Thr Tyr Tyr Arg Asp Gln Leu Lys
    1085                1090                1095

Val Pro Met Thr Ser Phe Leu Ile Leu Ser Val Phe Met Ile Leu
    1100                1105                1110

Met Pro Ile Leu Leu Met Asn Leu Leu Ile Gly Leu Ala Val Gly
    1115                1120                1125

Asp Ile Glu Ser Val Arg Arg Asn Ala Gln Leu Lys Arg Leu Ala
    1130                1135                1140

Met Gln Val Val Leu His Thr Glu Leu Glu Arg Lys Leu Pro His
    1145                1150                1155

Val Trp Leu Gln Arg Val Asp Lys Met Glu Leu Ile Glu Tyr Pro
    1160                1165                1170

Asn Glu Thr Lys Cys Lys Leu Gly Phe Cys Asp Phe Ile Leu Arg
    1175                1180                1185

Lys Trp Phe Ser Asn Pro Phe Thr Glu Asp Ser Ser Met Asp Val
    1190                1195                1200

Ile Ser Phe Asp Asn Asn Asp Asp Tyr Ile Asn Ala Glu Leu Glu
    1205                1210                1215

Arg Gln Arg Arg Lys Leu Arg Asp Ile Ser Arg Met Leu Glu Gln
    1220                1225                1230

Gln His His Leu Val Arg Leu Ile Val Gln Lys Met Glu Ile Lys
    1235                1240                1245

Thr Glu Ala Asp Asp Val Asp Glu Gly Ile Ser Pro Asn Glu Leu
    1250                1255                1260

Arg Ser Val Val Gly Leu Arg Ser Ala Gly Gly Asn Arg Trp Asn
    1265                1270                1275

Ser Pro Arg Val Arg Asn Lys Leu Arg Ala Ala Leu Ser Phe Asn
    1280                1285                1290

Lys Ser Met
    1295

<210> SEQ ID NO 5
<211> LENGTH: 1296
<212> TYPE: PRT
<213> ORGANISM: Drosophila melanogaster

<400> SEQUENCE: 5

Met Pro Lys Leu Tyr Asn Gly Val Tyr Ser Gly Gln Cys Gly Ala Leu
1               5                   10                  15

Ser Pro Pro Asp Leu Met Glu Ala Gln Pro Lys Leu Leu Pro Lys Pro
            20                  25                  30

Arg Ser Asn Ser Ser Gly Ser Thr Gly Arg Asn Ser Lys Tyr Trp Ile
        35                  40                  45

Phe Ser Met Ile Ile Glu Arg Ser Ala Gly Pro Lys Arg Ile Glu Ile
    50                  55                  60
```

```
Asp Gly Asp Asp Ala Asp Thr Pro Leu Glu Ala Ile Leu Pro Ala Glu
 65                  70                  75                  80

Pro Pro Ala Glu Val Cys Leu Leu Arg Asp Ser Pro Phe Arg Ile Leu
                 85                  90                  95

Arg Ser Thr Met Thr Ser Gly Asp Lys Glu Thr Pro Lys Arg Glu Asp
            100                 105                 110

Phe Ala Ser Ala Leu Arg Phe Leu Met Gly Gly Cys Ala Arg Glu Pro
            115                 120                 125

Glu Met Thr Ala Met Ala Pro Leu Asn Leu Pro Lys Lys Trp Ala Arg
        130                 135                 140

Ile Leu Arg Met Ser Ser Thr Pro Lys Ile Pro Ile Val Asp Tyr Leu
145                 150                 155                 160

Glu Ala Ala Glu Ser Gly Asn Leu Asp Asp Phe Lys Arg Leu Phe Met
                165                 170                 175

Ala Asp Asn Ser Arg Ile Ala Leu Lys Asp Ala Lys Gly Arg Thr Ala
            180                 185                 190

Ala His Gln Ala Ala Arg Asn Arg Val Asn Ile Leu Arg Tyr Ile
        195                 200                 205

Arg Asp Gln Asn Gly Asp Phe Asn Ala Lys Asp Asn Ala Gly Asn Thr
210                 215                 220

Pro Leu His Ile Ala Val Glu Ser Asp Ala Tyr Asp Ala Leu Asp Tyr
225                 230                 235                 240

Leu Leu Ser Ile Pro Val Asp Thr Gly Val Leu Asn Glu Lys Lys Gln
                245                 250                 255

Ala Pro Val His Leu Ala Thr Glu Leu Asn Lys Val Lys Ser Leu Arg
            260                 265                 270

Val Met Gly Gln Tyr Arg Asn Val Ile Asp Ile Gln Gln Gly Gly Glu
        275                 280                 285

His Gly Arg Thr Ala Leu His Leu Ala Ala Ile Tyr Asp His Glu Glu
    290                 295                 300

Cys Ala Arg Ile Leu Ile Thr Glu Phe Asp Ala Cys Pro Arg Lys Pro
305                 310                 315                 320

Cys Asn Asn Gly Tyr Tyr Pro Ile His Glu Ala Ala Lys Asn Ala Ser
                325                 330                 335

Ser Lys Thr Met Glu Val Phe Phe Gln Trp Gly Glu Gln Arg Gly Cys
            340                 345                 350

Thr Arg Glu Glu Met Ile Ser Phe Tyr Asp Ser Glu Gly Asn Val Pro
        355                 360                 365

Leu His Ser Ala Val His Gly Gly Asp Ile Lys Ala Val Glu Leu Cys
    370                 375                 380

Leu Lys Ser Gly Ala Lys Ile Ser Thr Gln Gln His Asp Leu Ser Thr
385                 390                 395                 400

Pro Val His Leu Ala Cys Ala Gln Gly Ala Ile Asp Ile Val Lys Leu
                405                 410                 415

Met Phe Glu Met Gln Pro Met Glu Lys Arg Leu Cys Leu Ser Cys Thr
            420                 425                 430

Asp Val Gln Lys Met Thr Pro Leu His Cys Ala Ser Met Phe Asp His
        435                 440                 445

Pro Asp Ile Val Ser Tyr Leu Val Ala Glu Gly Ala Asp Ile Asn Ala
    450                 455                 460

Leu Asp Lys Glu His Arg Ser Pro Leu Leu Ala Ala Ser Arg Ser
465                 470                 475                 480
```

-continued

```
Gly Trp Lys Thr Val His Leu Leu Ile Arg Leu Gly Ala Cys Ile Ser
                485                 490                 495
Val Lys Asp Ala Ala Arg Asn Val Leu His Phe Val Ile Met Asn
        500                 505                 510
Gly Gly Arg Leu Thr Asp Phe Ala Glu Gln Val Ala Asn Cys Gln Thr
        515                 520                 525
Gln Ala Gln Leu Lys Leu Leu Leu Asn Glu Lys Asp Ser Met Gly Cys
        530                 535                 540
Ser Pro Leu His Tyr Ala Ser Arg Asp Gly His Ile Arg Ser Leu Glu
545                 550                 555                 560
Asn Leu Ile Arg Leu Gly Ala Cys Ile Asn Leu Lys Asn Asn Asn Asn
                565                 570                 575
Glu Ser Pro Leu His Phe Ala Ala Arg Tyr Gly Arg Tyr Asn Thr Val
            580                 585                 590
Arg Gln Leu Leu Asp Ser Glu Lys Gly Ser Phe Ile Ile Asn Glu Ser
                595                 600                 605
Asp Gly Ala Gly Met Thr Pro Leu His Ile Ser Ser Gln Gln Gly His
        610                 615                 620
Thr Arg Val Val Gln Leu Leu Leu Asn Arg Gly Ala Leu Leu His Arg
625                 630                 635                 640
Asp His Thr Gly Arg Asn Pro Leu Gln Leu Ala Ala Met Ser Gly Tyr
                645                 650                 655
Thr Glu Thr Ile Glu Leu Leu His Ser Val His Ser His Leu Leu Asp
                660                 665                 670
Gln Val Asp Lys Asp Gly Asn Thr Ala Leu His Leu Ala Thr Met Glu
            675                 680                 685
Asn Lys Pro His Ala Ile Ser Val Leu Met Ser Met Gly Cys Lys Leu
        690                 695                 700
Val Tyr Asn Val Leu Asp Met Ser Ala Ile Asp Tyr Ala Ile Tyr Tyr
705                 710                 715                 720
Lys Tyr Pro Glu Ala Ala Leu Ala Met Val Thr His Glu Glu Arg Ala
                725                 730                 735
Asn Glu Val Met Ala Leu Arg Ser Asp Lys His Pro Cys Val Thr Leu
            740                 745                 750
Ala Leu Ile Ala Ser Met Pro Lys Val Phe Glu Ala Val Gln Asp Lys
        755                 760                 765
Cys Ile Thr Lys Ala Asn Cys Lys Lys Asp Ser Lys Ser Phe Tyr Ile
        770                 775                 780
Lys Tyr Ser Phe Ala Phe Leu Gln Cys Pro Phe Met Phe Ala Lys Ile
785                 790                 795                 800
Asp Glu Lys Thr Gly Glu Ser Ile Thr Thr Ala Ser Pro Ile Pro Leu
                805                 810                 815
Pro Ala Leu Asn Thr Met Val Thr His Gly Arg Val Glu Leu Leu Ala
            820                 825                 830
His Pro Leu Ser Gln Lys Tyr Leu Gln Met Lys Trp Asn Ser Tyr Gly
        835                 840                 845
Lys Tyr Phe His Leu Ala Asn Leu Leu Ile Tyr Ser Ile Phe Leu Val
        850                 855                 860
Phe Val Thr Ile Tyr Ser Ser Leu Met Met Asn Ile Glu Leu Lys
865                 870                 875                 880
Ala Gly Asp Asn Lys Thr Met Ser Gln Tyr Cys Asn Met Gly Trp Glu
                885                 890                 895
Gln Leu Thr Met Asn Leu Ser Gln Asn Pro Ser Val Ala Ser Gln Ile
```

-continued

```
                900             905             910
Arg Leu Asp Ser Cys Glu Glu Arg Ile Asn Arg Thr Thr Ala Ile Leu
        915             920             925
Phe Cys Ala Val Val Ile Val Tyr Ile Leu Leu Asn Ser Met Arg
        930             935             940
Glu Leu Ile Gln Ile Tyr Gln Gln Lys Leu His Tyr Ile Leu Glu Thr
945             950             955             960
Val Asn Leu Ile Ser Trp Val Leu Tyr Ile Ser Ala Leu Val Met Val
                965             970             975
Thr Pro Ala Phe Gln Pro Asp Gly Gly Ile Asn Thr Ile His Tyr Ser
                980             985             990
Ala Ala Ser Ile Ala Val Phe Leu Ser Trp Phe Arg Leu Leu Leu Phe
        995             1000            1005
Leu Gln Arg Phe Asp Gln Val Gly Ile Tyr Val Val Met Phe Leu
        1010            1015            1020
Glu Ile Leu Gln Thr Leu Ile Lys Val Leu Met Val Phe Ser Ile
        1025            1030            1035
Leu Ile Ile Ala Phe Gly Leu Ala Phe Tyr Ile Leu Leu Ser Lys
        1040            1045            1050
Ile Ile Asp Pro Gln Pro Asn His Leu Ser Phe Ser Asn Ile Pro
        1055            1060            1065
Met Ser Leu Leu Arg Thr Phe Ser Met Met Leu Gly Glu Leu Asp
        1070            1075            1080
Phe Val Gly Thr Tyr Val Asn Thr Tyr Tyr Arg Asp Gln Leu Lys
        1085            1090            1095
Val Pro Met Thr Ser Phe Leu Ile Leu Ser Val Phe Met Ile Leu
        1100            1105            1110
Met Pro Ile Leu Leu Met Asn Leu Leu Ile Gly Leu Ala Val Gly
        1115            1120            1125
Asp Ile Glu Ser Val Arg Arg Asn Ala Gln Leu Lys Arg Leu Ala
        1130            1135            1140
Met Gln Val Val Leu His Thr Glu Leu Glu Arg Lys Leu Pro His
        1145            1150            1155
Val Trp Leu Gln Arg Val Asp Lys Met Glu Leu Ile Glu Tyr Pro
        1160            1165            1170
Asn Glu Thr Lys Cys Lys Leu Gly Phe Cys Asp Phe Ile Leu Arg
        1175            1180            1185
Lys Trp Phe Ser Asn Pro Phe Thr Glu Asp Ser Ser Met Asp Val
        1190            1195            1200
Ile Ser Phe Asp Asn Asn Asp Asp Tyr Ile Asn Ala Glu Leu Glu
        1205            1210            1215
Arg Gln Arg Arg Lys Leu Arg Asp Ile Ser Arg Met Leu Glu Gln
        1220            1225            1230
Gln His His Leu Val Arg Leu Ile Val Gln Lys Met Glu Ile Lys
        1235            1240            1245
Thr Glu Ala Asp Asp Val Asp Glu Gly Ile Ser Pro Asn Glu Leu
        1250            1255            1260
Arg Ser Val Val Gly Leu Arg Ser Ala Gly Gly Asn Arg Trp Asn
        1265            1270            1275
Ser Pro Arg Val Arg Asn Lys Leu Arg Ala Ala Leu Ser Phe Asn
        1280            1285            1290
Lys Ser Met
        1295
```

<210> SEQ ID NO 6
<211> LENGTH: 1248
<212> TYPE: PRT
<213> ORGANISM: Anopheles gambiae

<400> SEQUENCE: 6

```
Met Pro Thr Pro Leu Tyr Leu Ile His Ser Pro Arg Ser Val Arg Ser
1               5                   10                  15

Asp Thr Asp His Asn His Pro Thr Cys Glu Val Asn His Glu Glu Glu
            20                  25                  30

Asp Leu Gln Gln Thr Gln Ala Phe Lys Asn Trp Leu Leu Ser Arg Leu
        35                  40                  45

Lys Leu Pro Thr Gly His Gly Ile Gln Asn Thr Lys Val Asn Gln Ile
    50                  55                  60

Asn Ala His Asp Asn Asn Glu Leu Gln Ala Ile Leu Thr Gln Pro Ala
65                  70                  75                  80

Glu Ala Glu Val Cys Leu Leu Ser Asp Ser Pro Tyr Arg Ile Leu Arg
                85                  90                  95

Ala Ala Glu Ala Gly Asn Leu Glu Glu Phe Ile Arg Leu Tyr Glu Gly
            100                 105                 110

Asp Asn Asn Arg Leu Ser Val Lys Asp Ser Lys Gly Arg Thr Ala Ala
        115                 120                 125

His Gln Ala Ala Ala Arg Asn Arg Val Asn Ile Leu Thr Phe Ile His
    130                 135                 140

Gly Gln Gly Gly Asn Leu Asn Ala Gln Asp Met Val Gly Asn Thr Pro
145                 150                 155                 160

Leu His Thr Ala Val Glu Asn Asp Ser Leu Asp Ala Leu Glu Phe Leu
                165                 170                 175

Leu Lys Ile Pro Val Ala Thr Asn Val Leu Asn Glu Lys Lys Leu Ala
            180                 185                 190

Pro Val His Leu Ala Thr Glu Gln Asn Lys Val His Ala Leu Gln Val
        195                 200                 205

Met Gly Lys Tyr Arg Glu Val Ile Asp Ile Gln Gln Gly Gly Glu His
    210                 215                 220

Gly Arg Thr Ala Leu His Leu Ala Ala Ile Tyr Asp Asn Glu Glu Cys
225                 230                 235                 240

Ala Arg Ile Leu Ile Ser Glu Phe Gly Ala Cys Pro Arg Lys Pro Cys
                245                 250                 255

Asn Asn Gly Tyr Tyr Pro Ile His Glu Ala Ala Lys Asn Ala Ser Ser
            260                 265                 270

Lys Thr Met Glu Val Phe Phe Gln Trp Gly Glu Ser Lys Gly Cys Thr
        275                 280                 285

Arg Glu Glu Met Ile Ser Phe Tyr Asp Ser Glu Gly Asn Val Pro Leu
    290                 295                 300

His Ser Ala Val His Gly Gly Asp Ile Lys Ala Val Glu Leu Cys Leu
305                 310                 315                 320

Lys Ser Gly Ala Lys Ile Ser Thr Gln Gln His Asp Leu Ser Thr Pro
                325                 330                 335

Val His Leu Ala Ala Gln Gly Ala Ile Glu Ile Val Lys Leu Met
            340                 345                 350

Phe Arg Met Gln Pro Leu Glu Lys Arg Ile Ser Leu Asn Cys Thr Asp
        355                 360                 365

Ile Gln Lys Met Thr Pro Leu His Cys Ala Ala Met Phe Asp His Pro
```

```
              370                 375                 380
Glu Ile Val Glu Tyr Leu Val Lys Glu Gly Ala Asp Ile Asn Ala Met
385                 390                 395                 400

Asp Lys Glu Lys Arg Ser Pro Leu Leu Leu Ser Ser Arg Gly Gly
            405                 410                 415

Trp Arg Thr Val Met Ala Leu Ile Arg Leu Gly Ala Asn Ile Ser Leu
                420                 425                 430

Lys Asp Ala Asn Ser Arg Asn Val Leu His Leu Val Ile Met Asn Gly
            435                 440                 445

Gly Cys Leu Asp Glu Phe Ala Lys Glu Val Cys Arg Thr Gln Ser Glu
            450                 455                 460

Ile Tyr Leu Leu Gln Leu Leu Asn Glu Lys Asp Asp Ala Gly Cys Ser
465                 470                 475                 480

Pro Leu His Tyr Ala Ser Arg Glu Gly His Ile Arg Ser Leu Glu Asn
                485                 490                 495

Leu Ile Arg Leu Gly Ala Cys Ile Asn Leu Lys Asn Asn Asn Asn Glu
            500                 505                 510

Ser Pro Leu His Phe Ala Ala Arg Tyr Gly Arg Tyr Asn Thr Val Arg
            515                 520                 525

Gln Leu Leu Asp Ser Glu Lys Gly Thr Phe Ile Ile Asn Glu Ser Asp
            530                 535                 540

Gly Glu Gly Leu Thr Pro Leu His Ile Ala Ser Gln Gln Gly His Thr
545                 550                 555                 560

Arg Val Val Gln Leu Leu Leu Asn Arg Gly Ala Leu Leu His Arg Asp
                565                 570                 575

His Asn Gly Arg Asn Pro Leu His Leu Ala Ala Met Ser Gly Tyr Arg
            580                 585                 590

Gln Thr Ile Glu Leu Leu His Ser Val His Ser His Leu Leu Asp Gln
            595                 600                 605

Val Asp Lys Asp Gly Asn Thr Ala Leu His Leu Ala Thr Met Glu Asn
610                 615                 620

Lys Pro Asn Ala Val Ile Leu Leu Ser Leu Gly Cys Lys Leu Leu
625                 630                 635                 640

His Asn Tyr Met Asp Met Ser Ala Ile Asp Tyr Ala Ile Tyr Tyr Lys
                645                 650                 655

Tyr Pro Glu Ala Ala Leu Ala Met Ala Thr His Glu Glu Arg Ser Ser
            660                 665                 670

Glu Val Met Ala Leu Lys Ser Asp Lys His Pro Cys Val Thr Leu Ala
            675                 680                 685

Leu Ile Ala Ser Met Pro Arg Val Phe Glu Ala Val Gln Asp Asn Cys
690                 695                 700

Ile Thr Lys Ala Asn Cys Lys Lys Asp Ser Lys Ser Phe Tyr Ile Arg
705                 710                 715                 720

Tyr Ser Phe Ser Cys Leu Gln Cys Pro Ala Leu Tyr Ala Gln Met Asp
                725                 730                 735

Ala Arg Thr Gly Glu Ala Val Gln Ile Ser Lys Pro Ile Pro Leu Pro
            740                 745                 750

Ala Leu Asn Ala Met Val Ala His Gly Arg Val Glu Leu Leu Ala His
            755                 760                 765

Pro Leu Ser Gln Lys Tyr Leu Gln Met Lys Trp Asn Ser Tyr Gly Lys
            770                 775                 780

Tyr Phe His Leu Ala Asn Leu Leu Phe Tyr Ser Val Phe Leu Phe Phe
785                 790                 795                 800
```

-continued

```
Val Thr Leu Phe Thr Ser Gln Leu Met Arg Asn Ala Thr Pro Ile Gly
            805                 810                 815

His Thr Asp Gly Asn His Thr Gln Ala Ala Gly Thr Pro Val Asp Ser
        820                 825                 830

Gly Gln His Ile Leu Ala Leu Arg Ser Thr Ile Ala Arg Ser Lys Gly
            835                 840                 845

Tyr Asn Leu Gly Thr Val Ala Asn Val Ser Ser Ser Val Ala Pro Pro
    850                 855                 860

Thr Ile Glu Glu Gln Met Glu Val Thr Thr Thr Leu Val Ser Gly
865                 870                 875                 880

Ile Gly Ile Ile Ile Tyr Ile Val Val Asn Ala Leu Arg Glu Leu Val
                885                 890                 895

Gln Val Tyr Gln Gln Lys Trp His Tyr Leu Leu Glu Pro Asn Asn Phe
            900                 905                 910

Ile Ser Trp Ile Leu Tyr Thr Ser Ala Leu Ile Met Ile Trp Pro Met
            915                 920                 925

Phe Ser Ser Gly Met Cys Phe Ser Ile Asn Tyr Ser Ala Ala Ser Ile
    930                 935                 940

Thr Val Phe Leu Ser Trp Phe Asn Leu Leu Phe Leu Gln Arg Phe
945                 950                 955                 960

Asp Gln Ile Gly Ile Tyr Val Val Met Phe Leu Glu Ile Leu Gln Thr
            965                 970                 975

Leu Ile Lys Val Leu Ile Val Phe Ser Ile Leu Ile Ile Ala Phe Gly
            980                 985                 990

Leu Ala Phe Tyr Ile Leu Leu Ser Lys Val Ser Glu Pro Gln Val Asn
            995                 1000                1005

His Leu Ser Phe Ser Ser Ile Pro Met Ser Leu Val Arg Thr Phe
    1010                1015                1020

Ser Met Met Leu Gly Glu Met Asp Phe Val Gly Thr Tyr Val Gln
    1025                1030                1035

Pro Tyr His Val Gly Asp Leu Pro Phe Pro Phe Pro Ser Phe Val
    1040                1045                1050

Ile Leu Cys Leu Phe Met Ile Leu Met Pro Ile Leu Leu Met Asn
    1055                1060                1065

Leu Leu Ile Gly Leu Ala Val Gly Asp Ile Glu Ser Val Arg Arg
    1070                1075                1080

Asn Ala Gln Leu Lys Arg Leu Ala Met Gln Val Val Leu His Thr
    1085                1090                1095

Glu Leu Glu Arg Lys Leu Pro Gln Met Trp Leu Glu Met Val Asp
    1100                1105                1110

Lys Met Glu Leu Ile Glu Tyr Pro Asn Glu Lys Lys Cys Lys Leu
    1115                1120                1125

Gly Phe Leu Asp Ser Val Leu Arg Lys Trp Phe Cys Asn Pro Phe
    1130                1135                1140

Thr Asp Asp Tyr Lys Gly Gly Ile Asp Tyr Val Leu Glu Asn Thr
    1145                1150                1155

Glu Asp Tyr Val Ala Val Glu Leu Glu Lys Gln Lys Arg Lys Leu
    1160                1165                1170

Arg Asp Ile Gly Thr Ala Leu Asp Ala Gln His Gln Leu Leu Arg
    1175                1180                1185

Leu Ile Val Gln Lys Met Glu Ile Lys Thr Glu Ala Asp Asp Val
    1190                1195                1200
```

-continued

```
Asp Glu Gly Val Ser Thr Ser Asp Leu Lys Ala Ser Ser Gly Leu
    1205                1210                1215

Leu Thr Gly Thr Arg Ser Ser Arg Trp Ser Ser Pro Arg Ile Arg
    1220                1225                1230

Lys Lys Leu Gly Ala Thr Leu Ser Phe Asn Lys Ser Ile Gly Lys
    1235                1240                1245

<210> SEQ ID NO 7
<211> LENGTH: 1317
<212> TYPE: PRT
<213> ORGANISM: Tribolium castaneum

<400> SEQUENCE: 7

Met Asp Lys Lys Arg Tyr Gly Val His Asn Asp Leu Leu Gln Ser Leu
1               5                   10                  15

Lys Asp Phe Gln Ile Ser Leu Arg Arg Thr Thr Met Pro Phe Val Thr
                20                  25                  30

Leu Ala Asn Val Ser Ile Asn Ser Gly Glu Ala Leu Arg Leu Asn Ile
            35                  40                  45

Gln Ala Glu Gly Gly Arg Ile Ser Ile Pro Glu Phe Pro Leu Gly Pro
        50                  55                  60

Arg Gly Leu Gln Arg Phe Arg Pro Arg Gln Thr Leu Ile Glu Ile
65                  70                  75                  80

Gly Thr Thr Lys Thr Ala Arg Ser Trp Arg Ile Asp Thr Glu Asp Pro
                85                  90                  95

Gln Arg Leu Ser Pro Ser Thr Pro Ile Ile Thr Val Leu Pro Ser Val
            100                 105                 110

Glu Val Pro Glu Lys Thr Thr Ile Tyr Pro Asp Glu Val Lys Cys Glu
        115                 120                 125

Thr Ser Gln Asp Arg Thr Arg Arg Asp Thr Leu Asn Trp Leu Met Ser
    130                 135                 140

Ser Leu Arg Ser Ile Leu Pro Ser Ser Gly His Lys Ser Ala Ser Gly
145                 150                 155                 160

Ser Pro Ser Glu Leu Gln Asn Met Leu Pro Ser Ser Val Lys Val His
                165                 170                 175

Arg Leu Ser Asn Ala Gly Lys Pro Pro Glu Asp Asn Gly Gly Ile Cys
            180                 185                 190

Leu Met Thr Glu Ser Pro Phe Arg Ile Leu Arg Val Ala Glu Cys Gly
        195                 200                 205

Asn Leu Glu Thr Phe Gln Arg Leu Tyr Phe Ala Asp Pro Thr Arg Leu
    210                 215                 220

Ser Ile Lys Asp Ser Arg Gly Arg Thr Ala Ala His Gln Ala Ala Ala
225                 230                 235                 240

Lys Asn Arg Ile Thr Ile Leu Gln Phe Ile Leu Ser Gln Gly Gly Asp
                245                 250                 255

Leu Asn Asn Gln Asp Asn Ala Gly Asn Thr Pro Leu His Val Ala Val
            260                 265                 270

Glu His Glu Ser Leu Asp Ala Val Asp Phe Leu Leu Gln Ala Gly Val
        275                 280                 285

Lys Thr Asn Ile Leu Asn Asp Lys Lys Gln Ala Ala Ile His Leu Val
    290                 295                 300

Thr Glu Leu Asn Lys Val Ser Val Leu Glu Val Met Gly Lys His Lys
305                 310                 315                 320

Asp Lys Ile Asp Ile Leu Gln Gly Gly Glu His Gly Arg Thr Ala Leu
                325                 330                 335
```

```
His Ile Ala Ala Ile Tyr Asp His Glu Glu Cys Ala Arg Ile Leu Ile
            340                 345                 350

Ser Val Phe Asp Ala Cys Pro Arg Pro Cys Asn Asn Gly Tyr Tyr
        355                 360                 365

Pro Ile His Glu Ala Ala Lys Asn Ala Ser Ser Lys Thr Leu Glu Ile
370                 375                 380

Phe Leu Gln Trp Gly Glu Ser Arg Gly Cys Thr Arg Glu Glu Met Ile
385                 390                 395                 400

Ser Phe Tyr Asp Ser Glu Gly Asn Val Pro Leu His Ser Ala Val His
                405                 410                 415

Gly Gly Asp Ile Lys Ala Val Glu Leu Cys Leu Arg Ser Gly Ala Lys
                420                 425                 430

Ile Ser Thr Gln Gln His Asp Leu Ser Thr Pro Val His Leu Ala Cys
                435                 440                 445

Ala Gln Gly Ala Thr Asp Ile Val Lys Leu Met Phe Lys Met Gln Pro
        450                 455                 460

Glu Lys Leu Pro Cys Leu Ala Ser Cys Asp Val Gln Lys Met Thr
465                 470                 475                 480

Pro Leu His Cys Ala Ala Met Phe Asp His Pro Glu Ile Val Glu Phe
                485                 490                 495

Leu Ile Asn Glu Gly Ala Asp Ile Asn Pro Met Asp Lys Glu Lys Arg
                500                 505                 510

Ser Pro Leu Leu Leu Ala Ala Leu Arg Gly Gly Trp Arg Thr Val His
        515                 520                 525

Val Leu Ile Arg Leu Gly Ala Asp Ile Asn Val Lys Asp Val Asn Arg
        530                 535                 540

Arg Asn Val Leu His Leu Val Val Met Asn Gly Gly Arg Leu Glu Gln
545                 550                 555                 560

Phe Ala Ser Glu Val Ser Lys Ala Lys Ser Gln Thr Ser Leu Leu Gln
                565                 570                 575

Leu Leu Asn Glu Lys Asp Ile Asn Gly Cys Ser Pro Leu His Tyr Ala
                580                 585                 590

Ser Arg Glu Gly His Ile Arg Ser Leu Glu Asn Leu Ile Arg Leu Gly
        595                 600                 605

Ala Thr Ile Asn Leu Lys Asn Asn Asn Glu Ser Pro Leu His Phe
        610                 615                 620

Ala Ala Arg Tyr Gly Arg Tyr Asn Thr Val Arg Gln Leu Leu Asp Ser
625                 630                 635                 640

Glu Lys Gly Thr Phe Ile Ile Asn Glu Ser Asp Gly Glu Gly Leu Thr
                645                 650                 655

Pro Leu His Ile Ala Ser Lys Gln Gly His Thr Arg Val Val Gln Leu
                660                 665                 670

Leu Leu Asn Arg Gly Ala Leu Leu His Arg Asp His Asn Gly Arg Asn
                675                 680                 685

Pro Leu His Leu Ala Ala Met Asn Gly Tyr Thr Gln Thr Ile Glu Leu
        690                 695                 700

Leu Leu Ser Val His Ser His Leu Leu Asp Gln Thr Asp Lys Asp Gly
705                 710                 715                 720

Asn Thr Ala Leu His Leu Ala Thr Met Glu Asn Lys Pro Asn Ala Ile
                725                 730                 735

Ala Leu Leu Leu Ser Met Asn Cys Lys Leu Leu Tyr Asn Gln Met Glu
                740                 745                 750
```

```
Met Ser Ala Ile Asp Tyr Ala Ile Tyr Tyr Lys Phe Pro Glu Ala Ala
            755                 760                 765
Leu Ala Met Val Thr His Glu Asp Arg Ala Glu Glu Val Met Ala Leu
    770                 775                 780
Lys Ser Ser Lys His Pro Tyr Val Thr Leu Ala Leu Ile Ala Ser Met
785                 790                 795                 800
Pro Arg Val Phe Glu Ala Val Gln Asp Lys Cys Ile Thr Lys Ala Asn
                805                 810                 815
Cys Lys Lys Asp Ser Lys Ser Phe Tyr Ile Lys Tyr Asn Phe Ser Ala
            820                 825                 830
Leu Gln Cys Ser Gln Phe Tyr Ala Asp Met Asp His Lys Thr Gly Asp
        835                 840                 845
Ala Leu Ala Ile Ser Lys Pro Ile Pro Leu Pro Ala Leu Asn Ala Met
850                 855                 860
Val Ser His Gly Arg Val Glu Leu Leu Ala His Pro Leu Ser Gln Lys
865                 870                 875                 880
Tyr Leu Gln Met Lys Trp Asn Ser Tyr Gly Lys Tyr Phe His Leu Thr
                885                 890                 895
Asn Val Leu Phe Tyr Ser Ile Phe Leu Thr Phe Val Thr Cys Phe Ala
                900                 905                 910
Tyr Glu Ile Met Arg His Glu Asp Gln Ile Ile Thr Tyr Asn Ala Thr
            915                 920                 925
Asn Leu Thr His Asp Glu Tyr Val Asn Phe Ser Lys Ala Asn Ile Leu
        930                 935                 940
Asn Val Lys Ile Thr Pro Met Met Tyr Met Ser Ala Leu Ala Ile Ile
945                 950                 955                 960
Thr Tyr Ile Ile Leu Asn Thr Ile Arg Glu Met Val Gln Val Tyr Gln
                965                 970                 975
Gln Lys Phe Met Tyr Phe Leu Asp Pro Asn Asn Leu Val Thr Trp Val
            980                 985                 990
Leu Tyr Thr Cys Ala Val Val Met  Val Phe Pro Ile Phe  Trp Gly Thr
                995                 1000                1005
Met Tyr  Glu Leu Gln Phe Ser  Cys Ala Ser Val Thr  Val Phe Leu
    1010                1015                1020
Ser Trp  Phe Asn Leu Leu Leu  Leu Leu Gln Arg Phe  Asp Gln Val
    1025                1030                1035
Gly Ile  Tyr Val Val Met Phe  Leu Glu Ile Leu Gln  Thr Leu Ile
    1040                1045                1050
Lys Val  Leu Leu Val Phe Ser  Ile Leu Ile Ile Ala  Phe Gly Leu
    1055                1060                1065
Ala Phe  Tyr Ile Leu Leu Ser  Arg Gly Asp His Leu  Ser Phe Lys
    1070                1075                1080
Thr Ile  Pro Met Ser Leu Val  Arg Thr Phe Ser Met  Met Leu Gly
    1085                1090                1095
Glu Ile  Asp Phe Leu Gly Thr  Tyr Val Lys Pro Tyr  Tyr Leu Thr
    1100                1105                1110
Thr Glu  Asp Glu Lys Ser Phe  Leu Pro Phe Pro Leu  Pro Ala Phe
    1115                1120                1125
Phe Ile  Leu Gly Leu Phe Met  Val Leu Met Pro Ile  Leu Leu Met
    1130                1135                1140
Asn Leu  Leu Ile Gly Leu Ala  Val Gly Asp Ile Glu  Ser Val Arg
    1145                1150                1155
Arg Asn  Ala Gln Leu Lys Arg  Leu Ala Met Gln Val  Val Leu His
```

```
              1160                1165                1170

Thr Glu Leu Glu Arg Lys Leu Pro Lys Met Leu Leu Glu Arg Val
        1175                1180                1185

Asp Lys Cys Glu Leu Ile Glu Tyr Pro Asn Asp Thr Lys Cys Lys
        1190                1195                1200

Leu Gly Phe Phe Asp Ser Ile Leu Arg Lys Trp Phe Gly Asn Pro
        1205                1210                1215

Phe Ser Asp Glu Gly Leu Asp Met Ala Met Glu Gly Val Glu Asp
        1220                1225                1230

Tyr Val Val Asn Glu Leu Asp Lys Thr Lys Arg Lys Leu Lys Glu
        1235                1240                1245

Ile Thr Thr Ala Leu Glu Thr Gln Gln Gln Phe Leu Arg Leu Ile
        1250                1255                1260

Val Gln Lys Met Glu Ile Lys Thr Glu Ala Asp Asp Val Asp Glu
        1265                1270                1275

Gly Val Ser Pro Asn Asp Leu Lys Pro Ile Thr Gly His Ala Ser
        1280                1285                1290

Lys Trp Thr Ser Pro Lys Ile Arg Lys Lys Leu Arg Ser Val Val
        1295                1300                1305

Ser Phe Asn Asn Lys Gly Ser Ser Thr
        1310                1315

<210> SEQ ID NO 8
<211> LENGTH: 1125
<212> TYPE: PRT
<213> ORGANISM: Rattus norvegicus

<400> SEQUENCE: 8

Met Lys Arg Ser Leu Arg Arg Val Leu Arg Pro Glu Arg Lys Glu
1               5                   10                  15

Val Gln Gly Val Val Tyr Arg Gly Val Gly Lys Asp Met Asp Cys Ser
                20                  25                  30

Lys Glu Ser Phe Lys Val Asp Ile Glu Gly Asp Met Cys Arg Leu Glu
            35                  40                  45

Ala Phe Ile Lys Asn Arg Arg Lys Leu Ser Lys Tyr Glu Asp Glu Asn
        50                  55                  60

Leu Cys Leu Leu His His Ala Ala Glu Gly Gln Val Glu Leu Met
65                  70                  75                  80

Gln Leu Ile Ile Asn Gly Ser Ser Cys Glu Ala Leu Asn Val Met Asp
                85                  90                  95

Asp Tyr Gly Asn Thr Pro Leu His Trp Ala Ala Glu Lys Asn Gln Val
            100                 105                 110

Glu Ser Val Lys Phe Leu Leu Ser Gln Gly Ala Asn Pro Asn Leu Arg
        115                 120                 125

Asn Arg Asn Met Met Ala Pro Leu His Ile Ala Val Gln Gly Met Tyr
    130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
            180                 185                 190

Cys Lys Ser Asn Lys Trp Gly Asp Tyr Pro Val His Gln Ala Ala Phe
        195                 200                 205
```

-continued

```
Ser Gly Ala Lys Arg Cys Met Glu Leu Ile Leu Ala Tyr Gly Glu Lys
    210                 215                 220

Thr Gly Tyr Ser Arg Glu Ala His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Ser Gly Ala His Ile Asp Met Met Glu Asn Ala
            260                 265                 270

Lys Cys Met Ala Leu His Phe Ala Ala Thr Gln Gly Ala Thr Asp Ile
        275                 280                 285

Val Lys Leu Met Ile Ser Ser Tyr Thr Gly Ser Ser Asp Ile Val Asn
290                 295                 300

Ala Val Asp Gly Asn Gln Glu Thr Leu Leu His Arg Ala Ser Leu Phe
305                 310                 315                 320

Asp His His Asp Leu Ala Asp Tyr Leu Ile Ser Val Gly Ala Asp Ile
                325                 330                 335

Asn Ser Thr Asp Ser Glu Gly Arg Ser Pro Leu Ile Leu Ala Thr Ala
            340                 345                 350

Ser Ala Ser Trp Asn Ile Val Asn Leu Leu Leu Ser Lys Gly Ala Lys
        355                 360                 365

Val Asp Ile Lys Asp His Leu Gly Arg Asn Phe Leu His Leu Thr Val
370                 375                 380

Gln Gln Pro Tyr Gly Leu Arg Asn Leu Arg Pro Glu Phe Leu Gln Met
385                 390                 395                 400

Gln His Ile Lys Glu Leu Val Met Asp Glu Asp Asn Asp Gly Cys Thr
                405                 410                 415

Pro Leu His Tyr Ala Cys Arg Gln Gly Ala Pro Val Ser Val Asn Asn
            420                 425                 430

Leu Leu Arg Phe Asn Val Ser Val His Ser Lys Ser Lys Asp Lys Lys
        435                 440                 445

Ser Pro Leu His Phe Ala Ala Ser Tyr Gly Arg Ile Asn Thr Cys Gln
450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
            500                 505                 510

His Asn Gly Trp Thr Ala Leu His His Ala Ser Met Gly Gly Tyr Thr
        515                 520                 525

Gln Thr Met Lys Val Ile Leu Asp Thr Asn Leu Lys Cys Thr Asp Arg
530                 535                 540

Leu Asp Glu Glu Gly Asn Thr Ala Leu His Phe Ala Ala Arg Glu Gly
545                 550                 555                 560

His Ala Lys Ala Val Ala Met Leu Leu Ser Tyr Asn Ala Asp Ile Leu
                565                 570                 575

Leu Asn Lys Lys Gln Ala Ser Phe Leu His Ile Ala Leu His Asn Lys
            580                 585                 590

Arg Lys Glu Val Val Leu Thr Thr Ile Arg Ser Lys Arg Trp Asp Glu
        595                 600                 605

Cys Leu Gln Val Phe Thr His Asp Ser Pro Ser Asn Arg Cys Pro Ile
610                 615                 620

Met Glu Met Val Glu Tyr Leu Pro Glu Cys Met Lys Val Leu Leu Asp
```

-continued

```
625                 630                 635                 640
Phe Cys Met Ile Pro Ser Thr Glu Asp Lys Ser Cys Gln Asp Tyr His
                    645                 650                 655
Ile Glu Tyr Asn Phe Lys Tyr Leu Gln Cys Pro Leu Ser Met Thr Lys
                    660                 665                 670
Lys Val Thr Pro Thr Gln Asp Val Ile Tyr Glu Pro Leu Thr Ile Leu
                    675                 680                 685
Asn Val Met Val Gln His Asn Arg Ile Glu Leu Leu Asn His Pro Val
                    690                 695                 700
Cys Arg Glu Tyr Leu Leu Met Lys Trp Cys Ala Tyr Gly Phe Arg Ala
705                 710                 715                 720
His Met Met Asn Leu Gly Ser Tyr Cys Leu Gly Leu Ile Pro Met Thr
                    725                 730                 735
Leu Leu Val Val Lys Ile Gln Pro Gly Met Ala Phe Asn Ser Thr Gly
                    740                 745                 750
Ile Ile Asn Glu Thr Ile Ser Thr His Glu Glu Arg Ile Asn Thr Leu
                    755                 760                 765
Asn Ser Phe Pro Leu Lys Ile Cys Met Ile Leu Val Phe Leu Ser Ser
                    770                 775                 780
Ile Phe Gly Tyr Cys Lys Glu Val Val Gln Ile Phe Gln Gln Lys Arg
785                 790                 795                 800
Asn Tyr Phe Leu Asp Tyr Asn Asn Ala Leu Glu Trp Val Ile Tyr Thr
                    805                 810                 815
Thr Ser Met Ile Phe Val Leu Pro Leu Phe Leu Asp Ile Pro Ala Tyr
                    820                 825                 830
Met Gln Trp Gln Cys Gly Ala Ile Ala Ile Phe Phe Tyr Trp Met Asn
                    835                 840                 845
Phe Leu Leu Tyr Leu Gln Arg Phe Glu Asn Cys Gly Ile Phe Ile Val
                    850                 855                 860
Met Leu Glu Val Ile Phe Lys Thr Leu Leu Arg Ser Thr Gly Val Phe
865                 870                 875                 880
Ile Phe Leu Leu Leu Ala Phe Gly Leu Ser Phe Tyr Val Leu Leu Asn
                    885                 890                 895
Phe Gln Asp Ala Phe Ser Thr Pro Leu Leu Ser Leu Ile Gln Thr Phe
                    900                 905                 910
Ser Met Met Leu Gly Asp Ile Asn Tyr Arg Asp Ala Phe Leu Glu Pro
                    915                 920                 925
Leu Phe Arg Asn Glu Leu Ala Tyr Pro Val Leu Thr Phe Gly Gln Leu
                    930                 935                 940
Ile Ala Phe Thr Met Phe Val Pro Ile Val Leu Met Asn Leu Leu Ile
945                 950                 955                 960
Gly Leu Ala Val Gly Asp Ile Ala Glu Val Gln Lys His Ala Ser Leu
                    965                 970                 975
Lys Arg Ile Ala Met Gln Val Glu Leu His Thr Asn Leu Glu Lys Lys
                    980                 985                 990
Leu Pro Phe Trp Tyr Leu Arg Lys  Val Asp Gln Arg Ser  Thr Ile Val
                    995                 1000                1005
Tyr Pro Asn Arg Pro Arg His  Gly Arg Met Leu Arg  Phe Phe His
            1010                1015                1020
Tyr Phe Leu Ser Met Gln Glu  Thr Arg Gln Glu Ala  Pro Asn Ile
            1025                1030                1035
Asp Thr Cys Leu Glu Met Glu  Ile Leu Lys Gln Lys  Tyr Arg Leu
            1040                1045                1050
```

```
Lys Asp Leu Thr Ser Leu Leu Glu Lys Gln His Glu Leu Ile Lys
    1055                1060                1065

Leu Ile Ile Gln Lys Met Glu Ile Ile Ser Glu Thr Glu Asp Glu
    1070                1075                1080

Asp Asn His Cys Ser Phe Asp Arg Phe Lys Lys Glu Arg Leu
    1085                1090                1095

Glu Gln Met His Ser Lys Trp Asn Phe Val Leu Asn Ala Val Lys
    1100                1105                1110

Thr Lys Thr His Cys Ser Ile Ser His Pro Asp Ile
    1115                1120                1125

<210> SEQ ID NO 9
<211> LENGTH: 1125
<212> TYPE: PRT
<213> ORGANISM: Rattus norvegicus

<400> SEQUENCE: 9

Met Lys Arg Ser Leu Arg Arg Val Leu Arg Pro Glu Glu Arg Lys Glu
1               5                   10                  15

Val Gln Gly Val Val Tyr Arg Gly Val Gly Lys Asp Met Asp Cys Ser
                20                  25                  30

Lys Glu Ser Phe Lys Val Asp Ile Glu Gly Asp Met Cys Arg Leu Glu
            35                  40                  45

Ala Phe Ile Lys Asn Arg Arg Lys Leu Ser Lys Tyr Glu Asp Glu Asn
        50                  55                  60

Leu Cys Leu Leu His His Ala Ala Ala Glu Gly Gln Val Glu Leu Met
65                  70                  75                  80

Gln Leu Ile Ile Asn Gly Ser Ser Cys Glu Ala Leu Asn Val Met Asp
                    85                  90                  95

Asp Tyr Gly Asn Thr Pro Leu His Trp Ala Ala Glu Lys Asn Gln Val
                100                 105                 110

Glu Ser Val Lys Phe Leu Leu Ser Gln Gly Ala Asn Pro Asn Leu Arg
            115                 120                 125

Asn Arg Asn Met Met Ala Pro Leu His Ile Ala Val Gln Gly Met Tyr
        130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                    165                 170                 175

Asp Asn Ser Glu Ala Leu Gln Ile Leu Leu Glu Lys Gly Ala Lys Leu
                180                 185                 190

Cys Lys Ser Asn Lys Trp Gly Asp Tyr Pro Val His Gln Ala Ala Phe
            195                 200                 205

Ser Gly Ala Lys Arg Cys Met Glu Leu Ile Leu Ala Tyr Gly Glu Lys
        210                 215                 220

Thr Gly Tyr Ser Arg Glu Ala His Ile Asn Phe Val Asn His Lys Lys
225                 230                 235                 240

Ala Ser Pro Leu His Leu Ala Val Gln Ser Gly Asp Leu Asp Met Ile
                    245                 250                 255

Lys Met Cys Leu Asp Ser Gly Ala His Ile Asp Met Met Glu Asn Ala
                260                 265                 270

Lys Cys Met Ala Leu His Phe Ala Ala Thr Gln Gly Ala Thr Asp Ile
            275                 280                 285

Val Lys Leu Met Ile Ser Ser Tyr Thr Gly Ser Ser Asp Ile Val Asn
```

```
              290                 295                 300

Ala Val Asp Gly Asn Gln Glu Thr Leu Leu His Arg Ala Ser Leu Phe
305                 310                 315                 320

Asp His His Asp Leu Ala Asp Tyr Leu Ile Ser Val Gly Ala Asp Ile
                325                 330                 335

Asn Ser Thr Asp Ser Glu Gly Arg Ser Pro Leu Ile Leu Ala Thr Ala
                340                 345                 350

Ser Ala Ser Trp Asn Ile Val Asn Leu Leu Leu Ser Lys Gly Ala Lys
                355                 360                 365

Val Asp Ile Lys Asp His Leu Gly Arg Asn Phe Leu His Leu Thr Val
370                 375                 380

Gln Gln Pro Tyr Gly Leu Arg Asn Leu Arg Pro Glu Phe Leu Gln Met
385                 390                 395                 400

Gln His Ile Lys Glu Leu Val Met Asp Glu Asp Asn Asp Gly Cys Thr
                405                 410                 415

Pro Leu His Tyr Ala Cys Arg Gln Gly Ala Pro Val Ser Val Asn Asn
                420                 425                 430

Leu Leu Arg Phe Asn Val Ser Val His Ser Lys Ser Lys Asp Lys Lys
                435                 440                 445

Ser Pro Leu His Phe Ala Ala Ser Tyr Gly Arg Ile Asn Thr Cys Gln
450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
                500                 505                 510

His Asn Gly Trp Thr Ala Leu His His Ala Ser Met Gly Gly Tyr Thr
                515                 520                 525

Gln Thr Met Lys Val Ile Leu Asp Thr Asn Leu Lys Cys Thr Asp Arg
530                 535                 540

Leu Asp Glu Glu Gly Asn Thr Ala Leu His Phe Ala Ala Arg Glu Gly
545                 550                 555                 560

His Ala Lys Ala Val Ala Met Leu Leu Ser Tyr Asn Ala Asp Ile Leu
                565                 570                 575

Leu Asn Lys Lys Gln Ala Ser Phe Leu His Ile Ala Leu His Asn Lys
                580                 585                 590

Arg Lys Glu Val Val Leu Thr Thr Ile Arg Ser Lys Arg Trp Asp Glu
                595                 600                 605

Cys Leu Gln Val Phe Thr His Asp Ser Pro Ser Asn Arg Cys Pro Ile
                610                 615                 620

Met Glu Met Val Glu Tyr Leu Pro Glu Cys Met Lys Val Leu Leu Asp
625                 630                 635                 640

Phe Cys Met Ile Pro Ser Thr Glu Asp Lys Ser Cys Gln Asp Tyr His
                645                 650                 655

Ile Glu Tyr Asn Phe Lys Tyr Leu Gln Cys Pro Leu Ser Met Thr Lys
                660                 665                 670

Lys Val Thr Pro Thr Gln Asp Val Ile Tyr Glu Pro Leu Thr Ile Leu
                675                 680                 685

Asn Val Met Val Gln His Asn Arg Ile Glu Leu Leu Asn His Pro Val
                690                 695                 700

Cys Arg Glu Tyr Leu Leu Met Lys Trp Cys Ala Tyr Gly Phe Arg Ala
705                 710                 715                 720
```

```
His Met Met Asn Leu Gly Ser Tyr Cys Leu Gly Leu Ile Pro Met Thr
                725                 730                 735

Leu Leu Val Val Lys Ile Gln Pro Gly Met Ala Phe Asn Ser Thr Gly
            740                 745                 750

Ile Ile Asn Glu Thr Ile Ser Thr His Glu Glu Arg Ile Asn Thr Leu
        755                 760                 765

Asn Ser Phe Pro Leu Lys Ile Cys Met Ile Leu Val Phe Leu Ser Ser
770                 775                 780

Ile Phe Gly Tyr Cys Lys Glu Val Val Gln Ile Phe Gln Gln Lys Arg
785                 790                 795                 800

Asn Tyr Phe Leu Asp Tyr Asn Asn Ala Leu Glu Trp Val Ile Tyr Thr
                805                 810                 815

Thr Ser Met Ile Phe Val Leu Pro Leu Phe Leu Asp Ile Pro Ala Tyr
            820                 825                 830

Met Gln Trp Gln Cys Gly Ala Ile Ala Ile Phe Phe Tyr Trp Met Asn
        835                 840                 845

Phe Leu Leu Tyr Leu Gln Arg Phe Glu Asn Cys Gly Ile Phe Ile Val
850                 855                 860

Met Leu Glu Val Ile Phe Lys Thr Leu Leu Arg Ser Thr Gly Val Phe
865                 870                 875                 880

Ile Phe Leu Leu Leu Ala Phe Gly Leu Ser Phe Tyr Val Leu Leu Asn
                885                 890                 895

Phe Gln Asp Ala Phe Ser Thr Pro Leu Leu Ser Leu Ile Gln Thr Phe
            900                 905                 910

Ser Met Met Leu Gly Asp Ile Asn Tyr Arg Asp Ala Phe Leu Glu Pro
        915                 920                 925

Leu Phe Arg Asn Glu Leu Ala Tyr Pro Val Leu Thr Phe Gly Gln Leu
    930                 935                 940

Ile Ala Phe Thr Met Phe Val Pro Ile Val Leu Met Asn Leu Leu Ile
945                 950                 955                 960

Gly Leu Ala Val Gly Asp Ile Ala Glu Val Gln Lys His Ala Ser Leu
                965                 970                 975

Lys Arg Ile Ala Met Gln Val Glu Leu His Thr Asn Leu Glu Lys Lys
            980                 985                 990

Leu Pro Phe Trp Tyr Leu Arg Lys  Val Asp Gln Arg Ser Thr Ile Val
        995                 1000                1005

Tyr Pro  Asn Arg Pro Arg His  Gly Arg Met Leu Arg  Phe Phe His
    1010                1015                1020

Tyr Phe  Leu Ser Met Gln Glu  Thr Arg Gln Glu Ala  Pro Asn Ile
    1025                1030                1035

Asp Thr  Cys Leu Glu Met Glu  Ile Leu Lys Gln Lys  Tyr Arg Leu
    1040                1045                1050

Lys Asp  Leu Thr Ser Leu Leu  Glu Lys Gln His Glu  Leu Ile Lys
    1055                1060                1065

Leu Ile  Ile Gln Lys Met Glu  Ile Ile Ser Glu Thr  Glu Asp Glu
    1070                1075                1080

Asp Asn  His Cys Ser Phe Gln  Asp Arg Phe Lys Lys  Glu Arg Leu
    1085                1090                1095

Glu Gln  Met His Ser Lys Trp  Asn Phe Val Leu Asn  Ala Val Lys
    1100                1105                1110

Thr Lys  Thr His Cys Ser Ile  Ser His Pro Asp Ile
    1115                1120                1125
```

<210> SEQ ID NO 10
<211> LENGTH: 1125
<212> TYPE: PRT
<213> ORGANISM: Mus musculus

<400> SEQUENCE: 10

```
Met Lys Arg Gly Leu Arg Arg Ile Leu Leu Pro Glu Glu Arg Lys Glu
1               5                   10                  15

Val Gln Gly Val Val Tyr Arg Gly Val Gly Glu Asp Met Asp Cys Ser
            20                  25                  30

Lys Glu Ser Phe Lys Val Asp Ile Glu Gly Asp Met Cys Arg Leu Glu
        35                  40                  45

Asp Phe Ile Lys Asn Arg Arg Lys Leu Ser Lys Tyr Glu Asp Glu Asn
    50                  55                  60

Leu Cys Pro Leu His His Ala Ala Glu Gly Gln Val Glu Leu Met
65                  70                  75                  80

Glu Leu Ile Ile Asn Gly Ser Ser Cys Glu Val Leu Asn Ile Met Asp
                85                  90                  95

Gly Tyr Gly Asn Thr Pro Leu His Cys Ala Ala Glu Lys Asn Gln Val
            100                 105                 110

Glu Ser Val Lys Phe Leu Leu Ser Gln Gly Ala Asn Pro Asn Leu Arg
        115                 120                 125

Asn Arg Asn Met Met Ser Pro Leu His Ile Ala Val His Gly Met Tyr
    130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
            180                 185                 190

Cys Lys Ser Asn Lys Trp Gly Asp Tyr Pro Val His Gln Ala Ala Phe
        195                 200                 205

Ser Gly Ala Lys Lys Cys Met Glu Leu Ile Leu Ala Tyr Gly Glu Lys
    210                 215                 220

Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Asn Gly His Ile Asp Met Met Glu Asn Ala
            260                 265                 270

Lys Cys Met Ala Leu His Phe Ala Ala Thr Gln Gly Ala Thr Asp Ile
        275                 280                 285

Val Lys Leu Met Ile Ser Ser Tyr Thr Gly Ser Ser Asp Ile Val Asn
    290                 295                 300

Ala Val Asp Gly Asn Gln Glu Thr Leu Leu His Arg Ala Ser Leu Phe
305                 310                 315                 320

Asp His His Asp Leu Ala Glu Tyr Leu Ile Ser Val Gly Ala Asp Ile
                325                 330                 335

Asn Ser Thr Asp Ser Glu Gly Arg Ser Pro Leu Ile Leu Ala Thr Ala
            340                 345                 350

Ser Ala Ser Trp Asn Ile Val Asn Leu Leu Leu Cys Lys Gly Ala Lys
        355                 360                 365

Val Asp Ile Lys Asp His Leu Gly Arg Asn Phe Leu His Leu Thr Val
    370                 375                 380
```

```
Gln Gln Pro Tyr Gly Leu Arg Asn Leu Arg Pro Glu Phe Met Gln Met
385                 390                 395                 400

Gln His Ile Lys Glu Leu Val Met Asp Glu Asp Asn Asp Gly Cys Thr
            405                 410                 415

Pro Leu His Tyr Ala Cys Arg Gln Gly Val Pro Val Ser Val Asn Asn
        420                 425                 430

Leu Leu Gly Phe Asn Val Ser Ile His Ser Lys Ser Lys Asp Lys Lys
    435                 440                 445

Ser Pro Leu His Phe Ala Ala Ser Tyr Gly Arg Ile Asn Thr Cys Gln
450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
            500                 505                 510

His Asn Gly Trp Thr Ala Leu His His Ala Ser Met Gly Gly Tyr Thr
        515                 520                 525

Gln Thr Met Lys Val Ile Leu Asp Thr Asn Leu Lys Cys Thr Asp Arg
    530                 535                 540

Leu Asp Glu Glu Gly Asn Thr Ala Leu His Phe Ala Ala Arg Glu Gly
545                 550                 555                 560

His Ala Lys Ala Val Ala Met Leu Leu Ser Tyr Asn Ala Asp Ile Leu
                565                 570                 575

Leu Asn Lys Lys Gln Ala Ser Phe Leu His Ile Ala Leu His Asn Lys
            580                 585                 590

Arg Lys Glu Val Val Leu Thr Thr Ile Arg Asn Lys Arg Trp Asp Glu
        595                 600                 605

Cys Leu Gln Val Phe Thr His Asn Ser Pro Ser Asn Arg Cys Pro Ile
    610                 615                 620

Met Glu Met Val Glu Tyr Leu Pro Glu Cys Met Lys Val Leu Leu Asp
625                 630                 635                 640

Phe Cys Met Ile Pro Ser Thr Glu Asp Lys Ser Cys Gln Asp Tyr His
                645                 650                 655

Ile Glu Tyr Asn Phe Lys Tyr Leu Gln Cys Pro Leu Ser Met Thr Lys
            660                 665                 670

Lys Val Ala Pro Thr Gln Asp Val Val Tyr Glu Pro Leu Thr Ile Leu
        675                 680                 685

Asn Val Met Val Gln His Asn Arg Ile Glu Leu Leu Asn His Pro Val
    690                 695                 700

Cys Arg Glu Tyr Leu Leu Met Lys Trp Cys Ala Tyr Gly Phe Arg Ala
705                 710                 715                 720

His Met Met Asn Leu Gly Ser Tyr Cys Leu Gly Leu Ile Pro Met Thr
                725                 730                 735

Leu Leu Val Val Lys Ile Gln Pro Gly Met Ala Phe Asn Ser Thr Gly
            740                 745                 750

Ile Ile Asn Gly Thr Ser Ser Thr His Glu Glu Arg Ile Asp Thr Leu
        755                 760                 765

Asn Ser Phe Pro Ile Lys Ile Cys Met Ile Leu Val Phe Leu Ser Ser
    770                 775                 780

Ile Phe Gly Tyr Cys Lys Glu Val Ile Gln Ile Phe Gln Gln Lys Arg
785                 790                 795                 800
```

Asn Tyr Phe Leu Asp Tyr Asn Asn Ala Leu Glu Trp Val Ile Tyr Thr
                805                 810                 815

Thr Ser Ile Ile Phe Val Leu Pro Leu Phe Leu Asn Ile Pro Ala Tyr
            820                 825                 830

Met Gln Trp Gln Cys Gly Ala Ile Ala Ile Phe Phe Tyr Trp Met Asn
        835                 840                 845

Phe Leu Leu Tyr Leu Gln Arg Phe Glu Asn Cys Gly Ile Phe Ile Val
    850                 855                 860

Met Leu Glu Val Ile Phe Lys Thr Leu Leu Arg Ser Thr Gly Val Phe
865                 870                 875                 880

Ile Phe Leu Leu Leu Ala Phe Gly Leu Ser Phe Tyr Val Leu Leu Asn
                885                 890                 895

Phe Gln Asp Ala Phe Ser Thr Pro Leu Leu Ser Leu Ile Gln Thr Phe
            900                 905                 910

Ser Met Met Leu Gly Asp Ile Asn Tyr Arg Asp Ala Phe Leu Glu Pro
        915                 920                 925

Leu Phe Arg Asn Glu Leu Ala Tyr Pro Val Leu Thr Phe Gly Gln Leu
    930                 935                 940

Ile Ala Phe Thr Met Phe Val Pro Ile Val Leu Met Asn Leu Leu Ile
945                 950                 955                 960

Gly Leu Ala Val Gly Asp Ile Ala Glu Val Gln Lys His Ala Ser Leu
                965                 970                 975

Lys Arg Ile Ala Met Gln Val Glu Leu His Thr Asn Leu Glu Lys Lys
            980                 985                 990

Leu Pro Leu Trp Tyr Leu Arg Lys Val Asp Gln Arg Ser Thr Ile Val
        995                 1000                1005

Tyr Pro Asn Arg Pro Arg His Gly Arg Met Leu Arg Phe Phe His
    1010                1015                1020

Tyr Phe Leu Asn Met Gln Glu Thr Arg Gln Glu Val Pro Asn Ile
    1025                1030                1035

Asp Thr Cys Leu Glu Met Glu Ile Leu Lys Gln Lys Tyr Arg Leu
    1040                1045                1050

Lys Asp Leu Thr Ser Leu Leu Glu Lys Gln His Glu Leu Ile Lys
    1055                1060                1065

Leu Ile Ile Gln Lys Met Glu Ile Ile Ser Glu Thr Glu Asp Glu
    1070                1075                1080

Asp Asn His Cys Ser Phe Gln Asp Arg Phe Lys Lys Glu Arg Leu
    1085                1090                1095

Glu Gln Met His Ser Lys Trp Asn Phe Val Leu Asn Ala Val Lys
    1100                1105                1110

Thr Lys Thr His Cys Ser Ile Ser His Pro Asp Phe
    1115                1120                1125

<210> SEQ ID NO 11
<211> LENGTH: 1119
<212> TYPE: PRT
<213> ORGANISM: Homo sapiens

<400> SEQUENCE: 11

Met Lys Arg Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
            20                  25                  30

Lys Glu Ser Leu Lys Val Val Phe Glu Gly Ser Ala Tyr Gly Leu Gln
        35                  40                  45

-continued

Asn Phe Asn Lys Gln Lys Lys Leu Lys Arg Cys Asp Asp Met Asp Thr
    50              55                  60

Phe Phe Leu His Tyr Ala Ala Glu Gly Gln Ile Glu Leu Met Glu
65              70                  75                  80

Lys Ile Thr Arg Asp Ser Ser Leu Glu Val Leu His Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Ile Ala Val Gln Gly Met Asn Asn
    130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
                165                 170                 175

Asn Ser Glu Ala Leu Gln Ile Leu Leu Lys Lys Gly Ala Lys Pro Cys
            180                 185                 190

Lys Ser Asn Lys Trp Gly Cys Phe Pro Ile His Gln Ala Ala Phe Ser
        195                 200                 205

Gly Ser Lys Glu Cys Met Glu Ile Ile Leu Arg Phe Gly Glu Glu His
    210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285

Lys Leu Met Ile Ser Ser Tyr Ser Gly Ser Val Asp Ile Val Asn Thr
    290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
        355                 360                 365

Asp Ile Lys Asp Asn Phe Gly Arg Asn Phe Leu His Leu Thr Val Gln
    370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Gly Ser Val Asn Asn Leu
            420                 425                 430

Leu Gly Phe Asn Val Ser Ile His Ser Lys Ser Lys Asp Lys Lys Ser
        435                 440                 445

Pro Leu His Phe Ala Ala Ser Tyr Gly Arg Ile Asn Thr Cys Gln Arg
    450                 455                 460

```
Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
            515                 520                 525

Thr Met Lys Val Ile Leu Asp Thr Asn Leu Lys Cys Thr Asp Arg Leu
        530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
            675                 680                 685

Met Val Gln Asn Asn Arg Ile Glu Leu Leu Asn His Pro Val Cys Lys
        690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
            755                 760                 765

Leu Ile Lys Thr Cys Met Ile Leu Val Phe Leu Ser Ser Ile Phe Gly
        770                 775                 780

Tyr Cys Lys Glu Ala Gly Gln Ile Phe Gln Gln Lys Arg Asn Tyr Phe
785                 790                 795                 800

Met Asp Ile Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
            850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
```

```
                            885                 890                 895
Pro Phe Ser Ser Pro Leu Leu Ser Ile Ile Gln Thr Phe Ser Met Met
                900                 905                 910

Leu Gly Asp Ile Asn Tyr Arg Glu Ser Phe Leu Glu Pro Tyr Leu Arg
                915                 920                 925

Asn Glu Leu Ala His Pro Val Leu Ser Phe Ala Gln Leu Val Ser Phe
            930                 935                 940

Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
        995                 1000                1005

Lys Pro Arg Ser Gly Gly Met Leu Phe His Ile Phe Cys Phe Leu
    1010                1015                1020

Phe Cys Thr Gly Glu Ile Arg Gln Glu Ile Pro Asn Ala Asp Lys
    1025                1030                1035

Ser Leu Glu Met Glu Ile Leu Lys Gln Lys Tyr Arg Leu Lys Asp
    1040                1045                1050

Leu Thr Phe Leu Leu Glu Lys Gln His Glu Leu Ile Lys Leu Ile
    1055                1060                1065

Ile Gln Lys Met Glu Ile Ile Ser Glu Thr Glu Asp Asp Asp Ser
    1070                1075                1080

His Cys Ser Phe Gln Asp Arg Phe Lys Lys Glu Gln Met Glu Gln
    1085                1090                1095

Arg Asn Ser Arg Trp Asn Thr Val Leu Arg Ala Val Lys Ala Lys
    1100                1105                1110

Thr His His Leu Glu Pro
    1115

<210> SEQ ID NO 12
<211> LENGTH: 1125
<212> TYPE: PRT
<213> ORGANISM: Mus musculus

<400> SEQUENCE: 12

Met Lys Arg Gly Leu Arg Arg Ile Leu Leu Pro Glu Glu Arg Lys Glu
1               5                   10                  15

Val Gln Gly Val Val Tyr Arg Gly Val Gly Glu Asp Met Asp Cys Ser
                20                  25                  30

Lys Glu Ser Phe Lys Val Asp Ile Glu Gly Asp Met Cys Arg Leu Glu
            35                  40                  45

Asp Phe Ile Lys Asn Arg Arg Lys Leu Ser Lys Tyr Glu Asp Glu Asn
        50                  55                  60

Leu Cys Pro Leu His His Ala Ala Ala Glu Gly Gln Val Glu Leu Met
65                  70                  75                  80

Glu Leu Ile Ile Asn Gly Ser Ser Cys Glu Val Leu Asn Ile Met Asp
                85                  90                  95

Gly Tyr Gly Asn Thr Pro Leu His Cys Ala Ala Glu Lys Asn Gln Val
                100                 105                 110

Glu Ser Val Lys Phe Leu Leu Ser Gln Gly Ala Asn Pro Asn Leu Arg
            115                 120                 125
```

-continued

```
Asn Arg Asn Met Met Ser Pro Leu His Ile Ala Val His Gly Met Tyr
    130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
            180                 185                 190

Cys Lys Ser Asn Lys Trp Gly Asp Tyr Pro Val His Gln Ala Ala Phe
        195                 200                 205

Ser Gly Ala Lys Lys Cys Met Glu Leu Ile Leu Ala Tyr Gly Glu Lys
    210                 215                 220

Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Asn Gly Ala His Ile Asp Met Met Glu Asn Ala
            260                 265                 270

Lys Cys Met Ala Leu His Phe Ala Ala Thr Gln Gly Ala Thr Asp Ile
        275                 280                 285

Val Lys Leu Met Ile Ser Ser Tyr Thr Gly Ser Ser Asp Ile Val Asn
    290                 295                 300

Ala Val Asp Gly Asn Gln Glu Thr Leu Leu His Arg Ala Ser Leu Phe
305                 310                 315                 320

Asp His His Asp Leu Ala Glu Tyr Leu Ile Ser Val Gly Ala Asp Ile
                325                 330                 335

Asn Ser Thr Asp Ser Glu Gly Arg Ser Pro Leu Ile Leu Ala Thr Ala
            340                 345                 350

Ser Ala Ser Trp Asn Ile Val Asn Leu Leu Leu Cys Lys Gly Ala Lys
        355                 360                 365

Val Asp Ile Lys Asp His Leu Gly Arg Asn Phe Leu His Leu Thr Val
    370                 375                 380

Gln Gln Pro Tyr Gly Leu Arg Asn Leu Arg Pro Glu Phe Met Gln Met
385                 390                 395                 400

Gln His Ile Lys Glu Leu Val Met Asp Glu Asp Asn Asp Gly Cys Thr
                405                 410                 415

Pro Leu His Tyr Ala Cys Arg Gln Gly Val Pro Val Ser Val Asn Asn
            420                 425                 430

Leu Leu Gly Phe Asn Val Ser Ile His Ser Lys Ser Lys Asp Lys Lys
        435                 440                 445

Ser Pro Leu His Phe Ala Ala Ser Tyr Gly Arg Ile Asn Thr Cys Gln
    450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
            500                 505                 510

His Asn Gly Trp Thr Ala Leu His Ala Ser Met Gly Gly Tyr Thr
        515                 520                 525

Gln Thr Met Lys Val Ile Leu Asp Thr Asn Leu Lys Cys Thr Asp Arg
    530                 535                 540

Leu Asp Glu Glu Gly Asn Thr Ala Leu His Phe Ala Ala Arg Glu Gly
```

```
                545                 550                 555                 560
        His Ala Lys Ala Val Ala Met Leu Leu Ser Tyr Asn Ala Asp Ile Leu
                        565                 570                 575

Leu Asn Lys Lys Gln Ala Ser Phe Leu His Ile Ala Leu His Asn Lys
                        580                 585                 590

Arg Lys Glu Val Val Leu Thr Thr Ile Arg Asn Lys Arg Trp Asp Glu
                        595                 600                 605

Cys Leu Gln Val Phe Thr His Asn Ser Pro Ser Asn Arg Cys Pro Ile
                        610                 615                 620

Met Glu Met Val Glu Tyr Leu Pro Glu Cys Met Lys Val Leu Leu Asp
        625                 630                 635                 640

Phe Cys Met Ile Pro Ser Thr Glu Asp Lys Ser Cys Gln Asp Tyr His
                        645                 650                 655

Ile Glu Tyr Asn Phe Lys Tyr Leu Gln Cys Pro Leu Ser Met Thr Lys
                        660                 665                 670

Lys Val Ala Pro Thr Gln Asp Val Val Tyr Glu Pro Leu Thr Ile Leu
                        675                 680                 685

Asn Val Met Val Gln His Asn Arg Ile Glu Leu Leu Asn His Pro Val
                        690                 695                 700

Cys Arg Glu Tyr Leu Leu Met Lys Trp Cys Ala Tyr Gly Phe Arg Ala
        705                 710                 715                 720

His Met Met Asn Leu Gly Ser Tyr Cys Leu Gly Leu Ile Pro Met Thr
                        725                 730                 735

Leu Leu Val Val Lys Ile Gln Pro Gly Met Ala Phe Asn Ser Thr Gly
                        740                 745                 750

Ile Ile Asn Gly Thr Ser Ser Thr His Glu Glu Arg Ile Asp Thr Leu
                        755                 760                 765

Asn Ser Phe Pro Ile Lys Ile Cys Met Ile Leu Val Phe Leu Ser Ser
                        770                 775                 780

Ile Phe Gly Tyr Cys Lys Glu Val Ile Gln Ile Phe Gln Gln Lys Arg
        785                 790                 795                 800

Asn Tyr Phe Leu Asp Tyr Asn Asn Ala Leu Glu Trp Val Ile Tyr Thr
                        805                 810                 815

Thr Ser Ile Ile Phe Val Leu Pro Leu Phe Leu Asn Ile Pro Ala Tyr
                        820                 825                 830

Met Gln Trp Gln Cys Gly Ala Ile Ala Ile Phe Phe Tyr Trp Met Asn
                        835                 840                 845

Phe Leu Leu Tyr Leu Gln Arg Phe Glu Asn Cys Gly Ile Phe Ile Val
                        850                 855                 860

Met Leu Glu Val Ile Phe Lys Thr Leu Leu Arg Ser Thr Gly Val Phe
        865                 870                 875                 880

Ile Phe Leu Leu Leu Ala Phe Gly Leu Ser Phe Tyr Val Leu Leu Asn
                        885                 890                 895

Phe Gln Asp Ala Phe Ser Thr Pro Leu Leu Ser Leu Ile Gln Thr Phe
                        900                 905                 910

Ser Met Met Leu Gly Asp Ile Asn Tyr Arg Asp Ala Phe Leu Glu Pro
                        915                 920                 925

Leu Phe Arg Asn Glu Leu Ala Tyr Pro Val Leu Thr Phe Gly Gln Leu
                        930                 935                 940

Ile Ala Phe Thr Met Phe Val Pro Ile Val Leu Met Asn Leu Leu Ile
        945                 950                 955                 960

Gly Leu Ala Val Gly Asp Ile Ala Glu Val Gln Lys His Ala Ser Leu
                        965                 970                 975
```

```
Lys Arg Ile Ala Met Gln Val Glu Leu His Thr Asn Leu Glu Lys Lys
            980                 985                 990

Leu Pro Leu Trp Tyr Leu Arg Lys  Val Asp Gln Arg Ser  Thr Ile Val
            995                 1000                1005

Tyr Pro  Asn Arg Pro Arg His  Gly Arg Met Leu Arg  Phe Phe His
         1010                1015                1020

Tyr Phe  Leu Asn Met Gln Glu  Thr Arg Gln Glu Val  Pro Asn Ile
         1025                1030                1035

Asp Thr  Cys Leu Glu Met Glu  Ile Leu Lys Gln Lys  Tyr Arg Leu
         1040                1045                1050

Lys Asp  Leu Thr Ser Leu Leu  Glu Lys Gln His Glu  Leu Ile Lys
         1055                1060                1065

Leu Ile  Ile Gln Lys Met Glu  Ile Ile Ser Glu Thr  Glu Asp Glu
         1070                1075                1080

Asp Asn  His Cys Ser Phe Gln  Asp Arg Phe Lys Lys  Glu Arg Leu
         1085                1090                1095

Glu Gln  Met His Ser Lys Trp  Asn Phe Val Leu Asn  Ala Val Lys
         1100                1105                1110

Thr Lys  Thr His Cys Ser Ile  Ser His Pro Asp Phe
         1115                1120                1125

<210> SEQ ID NO 13
<211> LENGTH: 1125
<212> TYPE: PRT
<213> ORGANISM: Mus musculus

<400> SEQUENCE: 13

Met Lys Arg Gly Leu Arg Arg Ile Leu Leu Pro Glu Glu Arg Lys Glu
1               5                   10                  15

Val Gln Gly Val Val Tyr Arg Gly Val Gly Glu Asp Met Asp Cys Ser
            20                  25                  30

Lys Glu Ser Phe Lys Val Asp Ile Glu Gly Asp Met Cys Arg Leu Glu
        35                  40                  45

Asp Phe Ile Lys Asn Arg Arg Lys Leu Ser Lys Tyr Glu Asp Glu Asn
    50                  55                  60

Leu Cys Pro Leu His His Ala Ala Glu Gly Gln Val Glu Leu Met
65                  70                  75                  80

Glu Leu Ile Ile Asn Gly Ser Ser Cys Glu Val Leu Asn Ile Met Asp
                85                  90                  95

Gly Tyr Gly Asn Thr Pro Leu His Cys Ala Ala Glu Lys Asn Gln Val
            100                 105                 110

Glu Ser Val Lys Phe Leu Leu Ser Gln Gly Ala Asn Pro Asn Leu Arg
        115                 120                 125

Asn Arg Asn Met Met Ser Pro Leu His Ile Ala Val His Gly Met Tyr
    130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Glu Lys Gly Ala Lys Leu
            180                 185                 190

Cys Lys Ser Asn Lys Trp Gly Asp Tyr Pro Val His Gln Ala Ala Phe
        195                 200                 205

Ser Gly Ala Lys Lys Cys Met Glu Leu Ile Leu Ala Tyr Gly Glu Lys
```

```
                    210                 215                 220
Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Asn Gly Ala His Ile Asp Met Met Glu Asn Ala
                260                 265                 270

Lys Cys Met Ala Leu His Phe Ala Ala Thr Gln Gly Ala Thr Asp Ile
            275                 280                 285

Val Lys Leu Met Ile Ser Ser Tyr Thr Gly Ser Ser Asp Ile Val Asn
        290                 295                 300

Ala Val Asp Gly Asn Gln Glu Thr Leu Leu His Arg Ala Ser Leu Phe
305                 310                 315                 320

Asp His His Asp Leu Ala Glu Tyr Leu Ile Ser Val Gly Ala Asp Ile
                325                 330                 335

Asn Ser Thr Asp Ser Glu Gly Arg Ser Pro Leu Ile Leu Ala Thr Ala
                340                 345                 350

Ser Ala Ser Trp Asn Ile Val Asn Leu Leu Leu Cys Lys Gly Ala Lys
            355                 360                 365

Val Asp Ile Lys Asp His Leu Gly Arg Asn Phe Leu His Leu Thr Val
370                 375                 380

Gln Gln Pro Tyr Gly Leu Arg Asn Leu Arg Pro Glu Phe Met Gln Met
385                 390                 395                 400

Gln His Ile Lys Glu Leu Val Met Asp Glu Asp Asn Asp Gly Cys Thr
                405                 410                 415

Pro Leu His Tyr Ala Cys Arg Gln Gly Val Pro Val Ser Val Asn Asn
                420                 425                 430

Leu Leu Gly Phe Asn Val Ser Ile His Ser Lys Ser Lys Asp Lys Lys
            435                 440                 445

Ser Pro Leu His Phe Ala Ala Ser Tyr Gly Arg Ile Asn Thr Cys Gln
450                 455                 460

Arg Leu Leu Gln Asp Ile Ser Asp Thr Arg Leu Leu Asn Glu Gly Asp
465                 470                 475                 480

Leu His Gly Met Thr Pro Leu His Leu Ala Ala Lys Asn Gly His Asp
                485                 490                 495

Lys Val Val Gln Leu Leu Leu Lys Lys Gly Ala Leu Phe Leu Ser Asp
                500                 505                 510

His Asn Gly Trp Thr Ala Leu His His Ala Ser Met Gly Gly Tyr Thr
            515                 520                 525

Gln Thr Met Lys Val Ile Leu Asp Thr Asn Leu Lys Cys Thr Asp Arg
        530                 535                 540

Leu Asp Glu Glu Gly Asn Thr Ala Leu His Phe Ala Ala Arg Glu Gly
545                 550                 555                 560

His Ala Lys Ala Val Ala Met Leu Leu Ser Tyr Asn Ala Asp Ile Leu
                565                 570                 575

Leu Asn Lys Lys Gln Ala Ser Phe Leu His Ile Ala Leu His Asn Lys
                580                 585                 590

Arg Lys Glu Val Val Leu Thr Thr Ile Arg Asn Lys Arg Trp Asp Glu
            595                 600                 605

Cys Leu Gln Val Phe Thr His Asn Ser Pro Ser Asn Arg Cys Pro Ile
610                 615                 620

Met Glu Met Val Glu Tyr Leu Pro Glu Cys Met Lys Val Leu Leu Asp
625                 630                 635                 640
```

```
Phe Cys Met Ile Pro Ser Thr Glu Asp Lys Ser Cys Gln Asp Tyr His
                645                 650                 655
Ile Glu Tyr Asn Phe Lys Tyr Leu Gln Cys Pro Leu Ser Met Thr Lys
            660                 665                 670
Lys Val Ala Pro Thr Gln Asp Val Val Tyr Glu Pro Leu Thr Ile Leu
            675                 680                 685
Asn Val Met Val Gln His Asn Arg Ile Glu Leu Leu Asn His Pro Val
        690                 695                 700
Cys Arg Glu Tyr Leu Leu Met Lys Trp Cys Ala Tyr Gly Phe Arg Ala
705                 710                 715                 720
His Met Met Asn Leu Gly Ser Tyr Cys Leu Gly Leu Ile Pro Met Thr
                725                 730                 735
Leu Leu Val Val Lys Ile Gln Pro Gly Met Ala Phe Asn Ser Thr Gly
            740                 745                 750
Ile Ile Asn Gly Thr Ser Ser Thr His Glu Glu Arg Ile Asp Thr Leu
            755                 760                 765
Asn Ser Phe Pro Ile Lys Ile Cys Met Ile Leu Val Phe Leu Ser Ser
    770                 775                 780
Ile Phe Gly Tyr Cys Lys Glu Val Ile Gln Ile Phe Gln Gln Lys Arg
785                 790                 795                 800
Asn Tyr Phe Leu Asp Tyr Asn Asn Ala Leu Glu Trp Val Ile Tyr Thr
                805                 810                 815
Thr Ser Ile Ile Phe Val Leu Pro Leu Phe Leu Asn Ile Pro Ala Tyr
            820                 825                 830
Met Gln Trp Gln Cys Gly Ala Ile Ala Ile Phe Phe Tyr Trp Met Asn
            835                 840                 845
Phe Leu Leu Tyr Leu Gln Arg Phe Glu Asn Cys Gly Ile Phe Ile Val
    850                 855                 860
Met Leu Glu Val Ile Phe Lys Thr Leu Arg Ser Thr Gly Val Phe Phe
865                 870                 875                 880
Ile Phe Leu Leu Leu Ala Phe Gly Leu Ser Phe Tyr Val Leu Leu Asn
                885                 890                 895
Phe Gln Asp Ala Phe Ser Thr Pro Leu Leu Ser Leu Ile Gln Thr Phe
            900                 905                 910
Ser Met Met Leu Gly Asp Ile Asn Tyr Arg Asp Ala Phe Leu Glu Pro
            915                 920                 925
Leu Phe Arg Asn Glu Leu Ala Tyr Pro Val Leu Thr Phe Gly Gln Leu
    930                 935                 940
Ile Ala Phe Thr Met Phe Val Pro Ile Val Leu Met Asn Leu Leu Ile
945                 950                 955                 960
Gly Leu Ala Val Gly Asp Ile Ala Glu Val Gln Lys His Ala Ser Leu
                965                 970                 975
Lys Arg Ile Ala Met Gln Val Glu Leu His Thr Asn Leu Glu Lys Lys
            980                 985                 990
Leu Pro Leu Trp Tyr Leu Arg Lys Val Asp Gln Arg Ser Thr Ile Val
        995                 1000                1005
Tyr Pro Asn Arg Pro Arg His Gly Arg Met Leu Arg Phe Phe His
    1010                1015                1020
Tyr Phe Leu Asn Met Gln Glu Thr Arg Gln Glu Val Pro Asn Ile
    1025                1030                1035
Asp Thr Cys Leu Glu Met Glu Ile Leu Lys Gln Lys Tyr Arg Leu
    1040                1045                1050
```

```
Lys Asp Leu Thr Ser Leu Leu Glu Lys Gln His Glu Leu Ile Lys
    1055                1060                1065

Leu Ile Ile Gln Lys Met Glu Ile Ile Ser Glu Thr Glu Asp Glu
    1070                1075                1080

Asp Asn His Cys Ser Phe Gln Asp Arg Phe Lys Lys Glu Arg Leu
    1085                1090                1095

Glu Gln Met His Ser Lys Trp Asn Phe Val Leu Asn Ala Val Lys
    1100                1105                1110

Thr Lys Thr His Cys Ser Ile Ser His Pro Asp Phe
    1115                1120                1125

<210> SEQ ID NO 14
<211> LENGTH: 1134
<212> TYPE: PRT
<213> ORGANISM: Mus musculus

<400> SEQUENCE: 14

Ala Pro Ala Gly Val Gln Val Glu Ser Met Lys Arg Gly Leu Arg Arg
1               5                   10                  15

Ile Leu Leu Pro Glu Glu Arg Lys Glu Val Gln Gly Val Val Tyr Arg
            20                  25                  30

Gly Val Gly Glu Asp Met Asp Cys Ser Lys Glu Ser Phe Lys Val Asp
        35                  40                  45

Ile Glu Gly Asp Met Cys Arg Leu Glu Asp Phe Ile Lys Asn Arg Arg
    50                  55                  60

Lys Leu Ser Lys Tyr Glu Asp Glu Asn Leu Cys Pro Leu His His Ala
65              70                  75                  80

Ala Ala Glu Gly Gln Val Glu Leu Met Glu Leu Ile Ile Asn Gly Ser
            85                  90                  95

Ser Cys Glu Val Leu Asn Ile Met Asp Gly Tyr Gly Asn Thr Pro Leu
        100                 105                 110

His Cys Ala Ala Glu Lys Asn Gln Val Glu Ser Val Lys Phe Leu Leu
    115                 120                 125

Ser Gln Gly Ala Asn Pro Asn Leu Arg Asn Arg Asn Met Met Ser Pro
130                 135                 140

Leu His Ile Ala Val His Gly Met Tyr Asn Glu Val Ile Lys Val Leu
145             150                 155                 160

Thr Glu His Lys Ala Thr Asn Ile Asn Leu Glu Gly Glu Asn Gly Asn
            165                 170                 175

Thr Ala Leu Met Ser Thr Cys Ala Lys Asp Asn Ser Glu Ala Leu Gln
        180                 185                 190

Ile Leu Leu Glu Lys Gly Ala Lys Leu Cys Lys Ser Asn Lys Trp Gly
    195                 200                 205

Asp Tyr Pro Val His Gln Ala Ala Phe Ser Gly Ala Lys Lys Cys Met
210                 215                 220

Glu Leu Ile Leu Ala Tyr Gly Glu Lys Asn Gly Tyr Ser Arg Glu Thr
225             230                 235                 240

His Ile Asn Phe Val Asn His Lys Lys Ala Ser Pro Leu His Leu Ala
            245                 250                 255

Val Gln Ser Gly Asp Leu Asp Met Ile Lys Met Cys Leu Asp Asn Gly
        260                 265                 270

Ala His Ile Asp Met Met Glu Asn Ala Lys Cys Met Ala Leu His Phe
    275                 280                 285

Ala Ala Thr Gln Gly Ala Thr Asp Ile Val Lys Leu Met Ile Ser Ser
290                 295                 300
```

```
Tyr Thr Gly Ser Ser Asp Ile Val Asn Ala Val Asp Gly Asn Gln Glu
305                 310                 315                 320

Thr Leu Leu His Arg Ala Ser Leu Phe Asp His His Asp Leu Ala Glu
            325                 330                 335

Tyr Leu Ile Ser Val Gly Ala Asp Ile Asn Ser Thr Asp Ser Glu Gly
            340                 345                 350

Arg Ser Pro Leu Ile Leu Ala Thr Ala Ser Ala Ser Trp Asn Ile Val
            355                 360                 365

Asn Leu Leu Leu Cys Lys Gly Ala Lys Val Asp Ile Lys Asp His Leu
370                 375                 380

Gly Arg Asn Phe Leu His Leu Thr Val Gln Gln Pro Tyr Gly Leu Arg
385                 390                 395                 400

Asn Leu Arg Pro Glu Phe Met Gln Met Gln His Ile Lys Glu Leu Val
            405                 410                 415

Met Asp Glu Asp Asn Asp Gly Cys Thr Pro Leu His Tyr Ala Cys Arg
            420                 425                 430

Gln Gly Val Pro Val Ser Val Asn Asn Leu Leu Gly Phe Asn Val Ser
            435                 440                 445

Ile His Ser Lys Ser Lys Asp Lys Lys Ser Pro Leu His Phe Ala Ala
450                 455                 460

Ser Tyr Gly Arg Ile Asn Thr Cys Gln Arg Leu Leu Gln Asp Ile Ser
465                 470                 475                 480

Asp Thr Arg Leu Leu Asn Glu Gly Asp Leu His Gly Met Thr Pro Leu
            485                 490                 495

His Leu Ala Ala Lys Asn Gly His Asp Lys Val Val Gln Leu Leu Leu
            500                 505                 510

Lys Lys Gly Ala Leu Phe Leu Ser Asp His Asn Gly Trp Thr Ala Leu
            515                 520                 525

His His Ala Ser Met Gly Gly Tyr Thr Gln Thr Met Lys Val Ile Leu
530                 535                 540

Asp Thr Asn Leu Lys Cys Thr Asp Arg Leu Asp Glu Glu Gly Asn Thr
545                 550                 555                 560

Ala Leu His Phe Ala Ala Arg Glu Gly His Ala Lys Ala Val Ala Met
            565                 570                 575

Leu Leu Ser Tyr Asn Ala Asp Ile Leu Leu Asn Lys Lys Gln Ala Ser
            580                 585                 590

Phe Leu His Ile Ala Leu His Asn Lys Arg Lys Glu Val Val Leu Thr
            595                 600                 605

Thr Ile Arg Asn Lys Arg Trp Asp Glu Cys Leu Gln Val Phe Thr His
            610                 615                 620

Asn Ser Pro Ser Asn Arg Cys Pro Ile Met Glu Met Val Glu Tyr Leu
625                 630                 635                 640

Pro Glu Cys Met Lys Val Leu Leu Asp Phe Cys Met Ile Pro Ser Thr
            645                 650                 655

Glu Asp Lys Ser Cys Gln Asp Tyr His Ile Glu Tyr Asn Phe Lys Tyr
            660                 665                 670

Leu Gln Cys Pro Leu Ser Met Thr Lys Lys Val Ala Pro Thr Gln Asp
            675                 680                 685

Val Val Tyr Glu Pro Leu Thr Ile Leu Asn Val Met Val Gln His Asn
            690                 695                 700

Arg Ile Glu Leu Leu Asn His Pro Val Cys Arg Glu Tyr Leu Leu Met
705                 710                 715                 720
```

-continued

```
Lys Trp Cys Ala Tyr Gly Phe Arg Ala His Met Met Asn Leu Gly Ser
            725                 730                 735

Tyr Cys Leu Gly Leu Ile Pro Met Thr Leu Leu Val Val Lys Ile Gln
            740                 745                 750

Pro Gly Met Ala Phe Asn Ser Thr Gly Ile Ile Asn Gly Thr Ser Ser
            755                 760                 765

Thr His Glu Glu Arg Ile Asp Thr Leu Asn Ser Phe Pro Ile Lys Ile
    770                 775                 780

Cys Met Ile Leu Val Phe Leu Ser Ser Ile Phe Gly Tyr Cys Lys Glu
785                 790                 795                 800

Val Ile Gln Ile Phe Gln Gln Lys Arg Asn Tyr Phe Leu Asp Tyr Asn
                805                 810                 815

Asn Ala Leu Glu Trp Val Ile Tyr Thr Thr Ser Ile Ile Phe Val Leu
            820                 825                 830

Pro Leu Phe Leu Asn Ile Pro Ala Tyr Met Gln Trp Gln Cys Gly Ala
            835                 840                 845

Ile Ala Ile Phe Phe Tyr Trp Met Asn Phe Leu Leu Tyr Leu Gln Arg
    850                 855                 860

Phe Glu Asn Cys Gly Ile Phe Ile Val Met Leu Glu Val Ile Phe Lys
865                 870                 875                 880

Thr Leu Leu Arg Ser Thr Gly Val Phe Ile Phe Leu Leu Ala Phe
                885                 890                 895

Gly Leu Ser Phe Tyr Val Leu Leu Asn Phe Gln Asp Ala Phe Ser Thr
                900                 905                 910

Pro Leu Leu Ser Leu Ile Gln Thr Phe Ser Met Met Leu Gly Asp Ile
            915                 920                 925

Asn Tyr Arg Asp Ala Phe Leu Glu Pro Leu Phe Arg Asn Glu Leu Ala
    930                 935                 940

Tyr Pro Val Leu Thr Phe Gly Gln Leu Ile Ala Phe Thr Met Phe Val
945                 950                 955                 960

Pro Ile Val Leu Met Asn Leu Leu Ile Gly Leu Ala Val Gly Asp Ile
                965                 970                 975

Ala Glu Val Gln Lys His Ala Ser Leu Lys Arg Ile Ala Met Gln Val
            980                 985                 990

Glu Leu His Thr Asn Leu Glu Lys Lys Leu Pro Leu Trp Tyr Leu Arg
    995                 1000                1005

Lys Val Asp Gln Arg Ser Thr Ile Val Tyr Pro Asn Arg Pro Arg
    1010                1015                1020

His Gly Arg Met Leu Arg Phe His Tyr Phe Leu Asn Met Gln
    1025                1030                1035

Glu Thr Arg Gln Glu Val Pro Asn Ile Asp Thr Cys Leu Glu Met
    1040                1045                1050

Glu Ile Leu Lys Gln Lys Tyr Arg Leu Lys Asp Leu Thr Ser Leu
    1055                1060                1065

Leu Glu Lys Gln His Glu Leu Ile Lys Leu Ile Ile Gln Lys Met
    1070                1075                1080

Glu Ile Ile Ser Glu Thr Glu Asp Glu Asp Asn His Cys Ser Phe
    1085                1090                1095

Gln Asp Arg Phe Lys Lys Glu Arg Leu Glu Gln Met His Ser Lys
    1100                1105                1110

Trp Asn Phe Val Leu Asn Ala Val Lys Thr Lys Thr His Cys Ser
    1115                1120                1125

Ile Ser His Pro Asp Phe
```

1130

<210> SEQ ID NO 15
<211> LENGTH: 1129
<212> TYPE: PRT
<213> ORGANISM: Mus musculus

<400> SEQUENCE: 15

```
Met Lys Arg Gly Leu Arg Arg Ile Leu Leu Pro Glu Glu Arg Lys Glu
1               5                   10                  15

Val Gln Gly Val Val Tyr Arg Gly Val Gly Glu Asp Met Asp Cys Ser
            20                  25                  30

Lys Glu Ser Phe Lys Val Asp Ile Glu Gly Asp Met Cys Arg Leu Glu
        35                  40                  45

Asp Phe Ile Lys Asn Arg Arg Lys Leu Ser Lys Tyr Glu Asp Glu Asn
    50                  55                  60

Leu Cys Pro Leu His His Ala Ala Glu Gly Gln Val Glu Leu Met
65                  70                  75                  80

Glu Leu Ile Ile Asn Gly Ser Ser Cys Glu Val Leu Asn Ile Met Asp
                85                  90                  95

Gly Tyr Gly Asn Thr Pro Leu His Cys Ala Ala Glu Lys Asn Gln Val
            100                 105                 110

Glu Ser Val Lys Phe Leu Leu Ser Gln Gly Ala Asn Pro Asn Leu Arg
        115                 120                 125

Asn Arg Asn Met Met Ser Pro Leu His Ile Ala Val His Gly Met Tyr
    130                 135                 140

Asn Glu Val Ile Lys Val Leu Thr Glu His Lys Ala Thr Asn Ile Asn
145                 150                 155                 160

Leu Glu Gly Glu Asn Gly Asn Thr Ala Leu Met Ser Thr Cys Ala Lys
                165                 170                 175

Asp Asn Ser Glu Ala Leu Gln Ile Leu Leu Lys Gly Ala Lys Leu
            180                 185                 190

Cys Lys Ser Asn Lys Trp Gly Asp Tyr Pro Val His Gln Ala Ala Phe
        195                 200                 205

Ser Gly Ala Lys Lys Cys Met Glu Leu Ile Leu Ala Tyr Gly Glu Lys
    210                 215                 220

Asn Gly Tyr Ser Arg Glu Thr His Ile Asn Phe Val Asn His Lys Lys
225                 230                 235                 240

Ala Ser Pro Leu His Leu Ala Val Gln Ser Gly Asp Leu Asp Met Ile
                245                 250                 255

Lys Met Cys Leu Asp Asn Gly Ala His Ile Asp Met Met Glu Ala Ser
            260                 265                 270

Asn Ala Lys Cys Met Ala Leu His Phe Ala Ala Thr Gln Gly Ala Thr
        275                 280                 285

Asp Ile Val Lys Leu Met Ile Ser Ser Tyr Thr Gly Ser Ser Asp Ile
    290                 295                 300

Val Asn Ala Val Asp Gly Asn Gln Glu Thr Leu Leu His Arg Gly Ala
305                 310                 315                 320

Asp Ile Asn Ser Thr Asp Ser Glu Gly Arg Ser Pro Leu Ile Leu Ala
                325                 330                 335

Thr Ala Ser Ala Ser Trp Asn Ile Val Asn Leu Leu Leu Cys Lys Gly
            340                 345                 350

Ala Lys Val Asp Ile Lys Asp His Leu Gly Arg Asn Phe Leu His Leu
        355                 360                 365
```

```
Thr Val Gln Gln Pro Tyr Gly Leu Arg Asn Leu Arg Pro Glu Phe Met
    370             375                 380

Gln Met Gln His Ile Lys Glu Leu Val Met Asp Glu Asp Asn Asp Gly
385             390                 395                 400

Cys Thr Pro Leu His Tyr Ala Cys Arg Gln Gly Val Pro Val Ser Val
                405                 410                 415

Asn Asn Leu Leu Gly Phe Asn Val Ser Ile His Ser Lys Ser Lys Asp
            420                 425             430

Lys Lys Ser Pro Leu His Phe Ala Ala Ser Tyr Gly Arg Ile Asn Thr
        435             440                 445

Cys Gln Arg Leu Leu Gln Asp Ile Ser Asp Thr Arg Leu Leu Asn Glu
    450                 455                 460

Gly Asp Leu His Gly Met Thr Pro Leu His Leu Ala Ala Lys Asn Gly
465             470                 475                 480

His Asp Lys Val Val Gln Leu Leu Leu Lys Lys Gly Ala Leu Phe Leu
                485                 490                 495

Ser Asp His Asn Gly Trp Thr Ala Leu His His Ala Ser Met Gly Gly
            500                 505                 510

Tyr Thr Gln Thr Met Lys Val Ile Leu Asp Thr Asn Leu Lys Cys Thr
    515                 520                 525

Asp Arg Leu Asp Glu Glu Gly Asn Thr Ala Leu His Phe Ala Ala Arg
    530                 535                 540

Glu Gly His Ala Lys Ala Val Ala Met Leu Leu Ser Tyr Asn Ala Asp
545                 550                 555                 560

Ile Leu Leu Asn Lys Lys Gln Ala Ser Phe Leu His Ile Ala Leu His
                565                 570                 575

Asn Lys Arg Lys Glu Val Val Leu Thr Thr Ile Arg Asn Lys Arg Trp
        580                 585                 590

Asp Glu Cys Leu Gln Val Phe Thr His Asn Ser Pro Ser Asn Arg Cys
    595                 600                 605

Pro Ile Met Glu Met Val Glu Tyr Leu Pro Glu Cys Met Lys Val Leu
    610                 615                 620

Leu Asp Phe Cys Met Ile Pro Ser Thr Glu Asp Lys Ser Cys Gln Asp
625             630                 635                 640

Tyr His Ile Glu Tyr Asn Phe Lys Tyr Leu Gln Cys Pro Leu Ser Met
                645                 650                 655

Thr Lys Lys Val Ala Pro Thr Gln Asp Val Val Tyr Glu Pro Leu Thr
            660                 665                 670

Ile Leu Asn Val Met Val Gln His Asn Arg Ile Glu Leu Leu Asn His
        675                 680                 685

Pro Val Cys Arg Glu Tyr Leu Leu Met Lys Trp Cys Ala Tyr Gly Phe
    690                 695                 700

Arg Ala His Met Met Asn Leu Gly Ser Tyr Cys Leu Gly Leu Ile Pro
705             710                 715                 720

Met Thr Leu Leu Val Val Lys Ile Gln Pro Gly Met Ala Phe Asn Ser
                725                 730                 735

Thr Gly Ile Ile Asn Gly Thr Ser Ser Thr His Glu Glu Arg Ile Asp
            740                 745                 750

Thr Leu Asn Ser Phe Pro Ile Lys Ile Cys Met Ile Leu Val Phe Leu
        755                 760                 765

Ser Ser Ile Phe Gly Tyr Cys Lys Glu Val Ile Gln Ile Phe Gln Gln
    770                 775                 780

Lys Arg Asn Tyr Phe Leu Asp Tyr Asn Asn Ala Leu Glu Trp Val Ile
```

```
                  785                 790                 795                 800
        Tyr Thr Thr Ser Ile Ile Phe Val Leu Pro Leu Phe Leu Asn Ile Pro
                            805                 810                 815

Ala Tyr Met Gln Trp Gln Cys Gly Ala Ile Ala Ile Phe Phe Tyr Trp
                            820                 825                 830

Met Asn Phe Leu Leu Tyr Leu Gln Arg Phe Glu Asn Cys Gly Ile Phe
                            835                 840                 845

Ile Val Met Leu Glu Val Ile Phe Lys Thr Leu Leu Arg Ser Thr Gly
                            850                 855                 860

Val Phe Ile Phe Leu Leu Leu Ala Phe Gly Leu Ser Phe Tyr Val Leu
        865                 870                 875                 880

Leu Asn Phe Gln Asp Ala Phe Ser Thr Pro Leu Leu Ser Leu Ile Gln
                            885                 890                 895

Thr Phe Ser Met Met Leu Gly Asp Ile Asn Tyr Arg Asp Ala Phe Leu
                            900                 905                 910

Glu Pro Leu Phe Arg Asn Glu Leu Ala Tyr Pro Val Leu Thr Phe Gly
                            915                 920                 925

Gln Leu Ile Ala Phe Thr Met Phe Val Pro Ile Val Leu Met Asn Leu
                            930                 935                 940

Leu Val Gly Arg Phe Glu Asn Cys Gly Ile Phe Ile Val Met Leu Glu
        945                 950                 955                 960

Val Ile Phe Lys Thr Leu Leu Arg Ser Thr Gly Val Phe Ile Phe Leu
                            965                 970                 975

Leu Leu Ala Phe Gly Leu Ser Phe Tyr Val Leu Leu Asn Phe Gln Asp
                            980                 985                 990

Ala Phe Ser Thr Pro Leu Leu Ser  Leu Ile Gln Thr Phe  Ser Met Met
                            995                1000                1005

Leu Gly  Asp Ile Asn Tyr Arg  Asp Ala Phe Leu Glu  Pro Leu Phe
                            1010                1015                1020

Arg Asn  Glu Leu Ala Tyr Pro  Val Leu Thr Phe Gly  Gln Leu Ile
                            1025                1030                1035

Ala Phe  Thr Met Phe Val Pro  Ile Val Leu Met Asn  Leu Leu Ile
                            1040                1045                1050

Gly Leu  Ala Val Gly Asp Ile  Ala Glu Val Gln Lys  His Ala Ser
                            1055                1060                1065

Leu Lys  Arg Ile Ala Met Gln  Val Glu Leu His Thr  Asn Leu Glu
                            1070                1075                1080

Lys Lys  Leu Pro Leu Trp Tyr  Leu Arg Lys Val Asp  Gln Arg Ser
                            1085                1090                1095

Thr Ile  Val Tyr Pro Asn Arg  Pro Arg His Gly Arg  Met Leu Lys
                            1100                1105                1110

His Asp  Lys Lys Tyr Gln Thr  Leu Thr His Ala Trp  Lys Trp Lys
                            1115                1120                1125

Tyr

<210> SEQ ID NO 16
<211> LENGTH: 1135
<212> TYPE: PRT
<213> ORGANISM: Bos taurus

<400> SEQUENCE: 16

Met Lys Lys Thr Asn Leu Arg Glu Asn Leu Asp Ile Leu Glu Ser Ser
1               5                   10                  15

Phe Ser Pro Leu Thr Ser Val Asp Ile Asn Val Cys Leu Glu Ser Tyr
```

-continued

```
                   20                  25                  30
Cys Ser Arg Pro Val Thr Thr Ala Asn Tyr Ala Gln Asn Leu Trp Asn
            35                  40                  45
Leu Ser Cys Lys Val Val Phe Glu Gly Asn Lys Cys Gly Leu Gln Asn
        50                  55                  60
Phe Val Lys Lys Gln Lys Arg Phe Lys Lys Tyr Asp Asp Val Asn Ala
 65                 70                  75                  80
Ser Pro Leu His His Ala Ala Glu Glu Gly Gln Val Glu Leu Met Glu
                85                  90                  95
Met Ile Val Asn Glu Ser Ser Cys Glu Val Leu Asn Val Met Asp Asp
            100                 105                 110
Tyr Gly Asn Thr Pro Leu His Trp Ala Ala Gly Lys Asn Gln Val Glu
        115                 120                 125
Ser Val Lys Phe Leu Leu Arg Lys Gly Ala Asn Pro Asn Leu Arg Asn
        130                 135                 140
Cys Ser Met Met Ala Pro Leu His Val Ala Val Gln Gly Gly Tyr Asn
145                 150                 155                 160
Asp Val Met Lys Val Leu Ile Glu His Ser Ser Thr Asp Val Asn Leu
                165                 170                 175
Glu Gly Glu Asn Gly Asn Thr Ala Leu Ile Ile Thr Cys Phe Thr Asp
            180                 185                 190
Asn Ser Glu Ala Met Gln Leu Leu Leu Asn Lys Gly Ala Lys Pro Cys
        195                 200                 205
Lys Ser Asn Lys Trp Gly Cys Phe Pro Ile His Gln Ala Ala Phe Ser
        210                 215                 220
Gly Ala Lys Lys Cys Met Glu Ile Ile Leu Lys Phe Gly Glu Glu His
225                 230                 235                 240
Gly Tyr Ser Arg Leu Ser His Ile Asn Phe Val Asn Ser Gly Lys Ala
                245                 250                 255
Ser Pro Leu His Met Ala Val Gln Ser Gly Asp Leu Asp Met Ile Lys
            260                 265                 270
Met Cys Leu Asp Asn Gly Ala Gln Leu Asp Leu Leu Glu Lys Gly Lys
        275                 280                 285
Cys Thr Ala Leu His Phe Ala Ala Thr Gln Gly Ala Thr Glu Ile Val
        290                 295                 300
Lys Leu Met Val Ser Ser Tyr Ser Gly Asn Ser Asp Ile Val Asn Glu
305                 310                 315                 320
Val Asp Gly Asn His Glu Thr Leu Leu His Arg Ala Ser Leu Phe Asp
                325                 330                 335
His His Glu Leu Ala Asp Tyr Leu Ile Ser Val Gly Ala Asp Ile Asp
            340                 345                 350
Ile Thr Asp Ser Glu Gly Arg Ser Pro Leu Leu Leu Ala Thr Ala Ser
        355                 360                 365
Ala Ser Trp Asn Thr Val Asn Leu Leu Leu Ser Lys Gly Ala Arg Val
        370                 375                 380
Asp Ile Lys Asp Asn Leu Gly Arg Asn Phe Leu His Leu Thr Val Gln
385                 390                 395                 400
Gln Pro Tyr Gly Leu Lys Asn Leu His Pro Glu Phe Leu Gln Met Gln
                405                 410                 415
His Ile Lys Glu Leu Val Met Asp Glu Asp Asn Asp Gly Cys Thr Pro
            420                 425                 430
Leu His Tyr Ala Cys Arg Gln Gly Val Pro Val Ser Val Asn Asn Leu
        435                 440                 445
```

```
Leu Asn Phe Asn Val Ser Ile His Ser Lys Ser Lys Asp Lys Lys Ser
        450                 455                 460
Pro Leu His Phe Ala Ala Ser Tyr Gly Arg Ile Asn Thr Cys Gln Arg
465                 470                 475                 480
Leu Leu Gln Asp Ile Ser Asp Thr Arg Leu Leu Asn Glu Gly Asp Leu
                485                 490                 495
His Gly Met Thr Pro Leu His Leu Ala Ala Lys Asn Gly His Asp Lys
            500                 505                 510
Val Val Gln Leu Leu Leu Lys Lys Gly Ala Leu Phe Leu Ser Asp His
        515                 520                 525
Asn Gly Trp Thr Ala Leu His His Ala Ser Leu Gly Gly Tyr Thr Gln
530                 535                 540
Thr Met Lys Val Ile Leu Asp Thr Asn Leu Lys Cys Thr Asp Arg Leu
545                 550                 555                 560
Asp Glu Glu Gly Asn Thr Ala Leu His Phe Ala Ala Arg Glu Gly His
                565                 570                 575
Ala Lys Ala Val Ser Leu Leu Leu Ser Tyr Asp Ala Asp Val Val Leu
            580                 585                 590
Asn Lys Gln Gln Ala Ser Phe Leu His Val Ala Ile His Asn Lys Arg
        595                 600                 605
Lys Glu Val Val Leu Thr Thr Ile Arg Ser Lys Arg Trp Gly Glu Cys
610                 615                 620
Phe Lys Val Phe Asn His Cys Ser Pro Thr Asn Arg Cys Pro Val Ile
625                 630                 635                 640
Glu Leu Val Glu Tyr Leu Pro Glu Cys Met Lys Val Leu Leu Asp Phe
                645                 650                 655
Cys Val Met Pro Ser Thr Glu Asp Lys Ser Ser Gln Asp Tyr His Ile
            660                 665                 670
Glu Tyr Asn Phe Thr Tyr Leu Gln Cys Pro Leu Glu Phe Thr Lys Lys
        675                 680                 685
Gly Thr Pro Val Pro Asp Ile Val Tyr Glu Pro Leu Leu Thr Leu Asn
690                 695                 700
Ala Met Val Gln His Asn Arg Ile Glu Leu Leu Asn His Pro Val Cys
705                 710                 715                 720
Lys Glu Tyr Leu Leu Met Lys Trp Leu Ala Tyr Gly Phe Arg Ala His
                725                 730                 735
Val Leu Asn Leu Gly Ser Tyr Cys Leu Gly Leu Phe Pro Met Thr Phe
            740                 745                 750
Leu Val Val Ser Ile Arg Pro Gly Met Ala Phe Asn Ser Thr Gly Ile
        755                 760                 765
Ile Asn Glu Thr Ser Asp His Ser Glu Ile Leu Asp Thr Lys Asn Ser
770                 775                 780
Phe Ala Ile Asn Phe Cys Met Ile Leu Val Leu Leu Ser Ser Ile Leu
785                 790                 795                 800
Gly Tyr Cys Lys Glu Val Ala Gln Ile Phe Gln Gln Lys Arg Asn Tyr
                805                 810                 815
Phe Leu Asp Lys Asp Asn Ala Ala Glu Trp Ile Ile Tyr Thr Thr Ser
            820                 825                 830
Ile Ile Phe Val Ser Pro Leu Phe Arg Ile Pro Ala Tyr Val Gln
        835                 840                 845
Trp Gln Cys Gly Ala Val Ala Ile Phe Leu Tyr Trp Met Asn Phe Leu
850                 855                 860
```

```
Leu Tyr Leu Gln Arg Phe Glu Lys Cys Gly Ile Phe Ile Val Met Leu
865                 870                 875                 880

Glu Val Ile Met Lys Thr Leu Leu Lys Ser Thr Ile Val Phe Val Phe
                885                 890                 895

Leu Leu Val Ala Phe Gly Leu Cys Phe Tyr Val Leu Leu Asn Ile Gln
            900                 905                 910

Asp Ala Phe Ser Ser Pro Phe Leu Ser Ile Ile Gln Thr Phe Ser Met
            915                 920                 925

Met Leu Gly Asp Ile Asn Tyr His Asp Ala Phe Leu Glu Pro Tyr Leu
        930                 935                 940

Lys Asn Glu Leu Glu Tyr Pro Leu Leu Ser Phe Val His Leu Ile Ile
945                 950                 955                 960

Phe Thr Met Phe Val Pro Ile Val Leu Met Asn Leu Leu Ile Gly Leu
                965                 970                 975

Ala Val Gly Asp Ile Ala Glu Val Gln Lys His Ala Leu Leu Lys Arg
            980                 985                 990

Ile Ala Met Gln Val Glu Leu His Thr Ser Leu Glu Lys Lys Leu Pro
        995                 1000                1005

Leu Trp Phe Leu His Lys Val Asp Gln Lys Ser Ile Ile Val Tyr
    1010                1015                1020

Pro Asn Arg Pro Arg Tyr Ser Arg Gly Ile Leu Arg Gly Val Phe
    1025                1030                1035

His Tyr Ile Phe Cys Pro His Glu Thr Arg Gln Glu Ile Pro Asn
    1040                1045                1050

Val Asp Thr Ser Leu Glu Thr Glu Ile Met Lys Gln Lys Tyr Arg
    1055                1060                1065

Leu Lys Asp Leu Ser Ser Leu Leu Glu Lys Gln His Glu Leu Ile
    1070                1075                1080

Lys Leu Ile Ile Gln Lys Met Glu Ile Ile Ser Glu Thr Glu Asp
    1085                1090                1095

Glu Asp Tyr His Ser Ser Phe Gln Asp Arg Phe Lys Lys Gln Gln
    1100                1105                1110

Leu Glu Gln Arg Asn Ser Lys Trp Asn Cys Val Leu Arg Ala Val
    1115                1120                1125

Lys Ala Lys Thr His Ser Pro
    1130                1135

<210> SEQ ID NO 17
<211> LENGTH: 1119
<212> TYPE: PRT
<213> ORGANISM: Pan troglodytes

<400> SEQUENCE: 17

Met Lys Cys Ser Leu Arg Lys Met Trp Arg Pro Gly Glu Lys Lys Glu
1               5                   10                  15

Pro Gln Gly Val Val Tyr Glu Asp Val Pro Asp Asp Thr Glu Asp Phe
                20                  25                  30

Lys Glu Ser Leu Lys Val Val Phe Glu Gly Ser Ala Tyr Gly Leu Gln
            35                  40                  45

Asn Phe Asn Lys Gln Lys Lys Leu Lys Arg Cys Asp Asp Met Asp Thr
        50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu His Glu Met Asp Asp
                85                  90                  95
```

```
Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
            115                 120                 125

Phe Asn Met Met Ala Pro Leu His Ile Ala Val Gln Gly Met Asn Asn
            130                 135                 140

Glu Val Met Lys Val Leu Leu Glu His Arg Thr Ile Asp Val Asn Leu
145                 150                 155                 160

Glu Gly Glu Asn Gly Asn Thr Ala Val Ile Ile Ala Cys Thr Thr Asn
            165                 170                 175

Asn Ser Glu Ala Leu Gln Ile Leu Leu Asn Lys Gly Ala Lys Pro Cys
            180                 185                 190

Lys Ser Asn Lys Trp Gly Cys Phe Pro Ile His Gln Ala Ala Phe Ser
            195                 200                 205

Gly Ser Lys Glu Cys Met Glu Ile Ile Leu Arg Phe Gly Glu Glu His
            210                 215                 220

Gly Tyr Ser Arg Gln Leu His Ile Asn Phe Met Asn Asn Gly Lys Ala
225                 230                 235                 240

Thr Pro Leu His Leu Ala Val Gln Asn Gly Asp Leu Glu Met Ile Lys
            245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
            275                 280                 285

Lys Leu Met Ile Ser Ser Tyr Ser Gly Ser Val Asp Ile Val Asn Thr
            290                 295                 300

Thr Asp Gly Cys His Glu Thr Met Leu His Arg Ala Ser Leu Phe Asp
305                 310                 315                 320

His His Glu Leu Ala Asp Tyr Leu Ile Ser Val Gly Ala Asp Ile Asn
            325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Ser Lys Gly Ala Gln Val
            355                 360                 365

Asp Ile Lys Asp Asn Phe Gly Arg Asn Phe Leu His Leu Thr Val Gln
            370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
            405                 410                 415

Leu His Tyr Ala Cys Arg Gln Gly Gly Pro Gly Ser Val Asn Asn Leu
            420                 425                 430

Leu Gly Phe Asn Val Ser Ile His Ser Lys Ser Lys Asp Lys Lys Ser
            435                 440                 445

Pro Leu His Phe Ala Ala Ser Tyr Gly Arg Ile Asn Thr Cys Gln Arg
            450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly Tyr Asp Lys
            485                 490                 495

Val Val Gln Leu Leu Leu Lys Lys Gly Ala Leu Phe Leu Ser Asp His
            500                 505                 510
```

```
Asn Gly Trp Thr Ala Leu His His Ala Ser Met Gly Tyr Thr Gln
        515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys
        595                 600                 605

Leu Lys Ile Phe Ser His Asn Ser Pro Gly Asn Lys Cys Pro Ile Thr
    610                 615                 620

Glu Met Ile Glu Tyr Leu Pro Glu Cys Met Lys Val Leu Leu Asp Phe
625                 630                 635                 640

Cys Met Leu His Ser Thr Glu Asp Lys Ser Cys Arg Asp Tyr Tyr Ile
                645                 650                 655

Glu Tyr Asn Phe Lys Tyr Leu Gln Cys Pro Leu Glu Phe Thr Lys Lys
            660                 665                 670

Thr Pro Thr Gln Asp Val Ile Tyr Glu Pro Leu Thr Ala Leu Asn Ala
        675                 680                 685

Met Val Gln Asn Asn Arg Ile Glu Leu Leu Asn His Pro Val Cys Lys
    690                 695                 700

Glu Tyr Leu Leu Met Lys Trp Leu Ala Tyr Gly Phe Arg Ala His Met
705                 710                 715                 720

Met Asn Leu Gly Ser Tyr Cys Leu Gly Leu Ile Pro Met Thr Ile Leu
                725                 730                 735

Val Val Asn Ile Lys Pro Gly Met Ala Phe Asn Ser Thr Gly Ile Ile
            740                 745                 750

Asn Glu Thr Ser Asp His Ser Glu Ile Leu Asp Thr Thr Asn Ser Tyr
        755                 760                 765

Leu Ile Lys Thr Cys Met Ile Leu Val Phe Leu Ser Ser Ile Phe Gly
    770                 775                 780

Tyr Cys Lys Glu Ala Gly Gln Ile Phe Gln Gln Lys Arg Asn Tyr Phe
785                 790                 795                 800

Met Asp Met Ser Asn Val Leu Glu Trp Ile Ile Tyr Thr Thr Gly Ile
                805                 810                 815

Ile Phe Val Leu Pro Leu Phe Val Glu Ile Pro Ala His Leu Gln Trp
            820                 825                 830

Gln Cys Gly Ala Ile Ala Val Tyr Phe Tyr Trp Met Asn Phe Leu Leu
        835                 840                 845

Tyr Leu Gln Arg Phe Glu Asn Cys Gly Ile Phe Ile Val Met Leu Glu
    850                 855                 860

Val Ile Leu Lys Thr Leu Leu Arg Ser Thr Val Val Phe Ile Phe Leu
865                 870                 875                 880

Leu Leu Ala Phe Gly Leu Ser Phe Tyr Ile Leu Leu Asn Leu Gln Asp
                885                 890                 895

Pro Phe Ser Ser Pro Leu Leu Ser Ile Ile Gln Thr Phe Ser Met Met
            900                 905                 910

Leu Gly Asp Ile Asn Tyr Arg Glu Ser Phe Leu Glu Pro Tyr Leu Arg
        915                 920                 925

Asn Glu Leu Ala His Pro Val Leu Ser Phe Ala Gln Leu Val Ser Phe
```

```
                930           935           940
Thr Ile Phe Val Pro Ile Val Leu Met Asn Leu Leu Ile Gly Leu Ala
945                 950                 955                 960

Val Gly Asp Ile Ala Glu Val Gln Lys His Ala Ser Leu Lys Arg Ile
                965                 970                 975

Ala Met Gln Val Glu Leu His Thr Ser Leu Glu Lys Lys Leu Pro Leu
            980                 985                 990

Trp Phe Leu Arg Lys Val Asp Gln Lys Ser Thr Ile Val Tyr Pro Asn
        995                1000               1005

Lys Pro Arg Ser Gly Gly Met Leu Phe His Ile Phe Cys Phe Leu
    1010               1015               1020

Phe Cys Thr Gly Glu Ile Arg Gln Glu Ile Pro Asn Ala Asp Lys
    1025               1030               1035

Ser Leu Glu Met Glu Ile Leu Lys Gln Lys Tyr Arg Leu Lys Asp
    1040               1045               1050

Leu Thr Phe Leu Leu Glu Lys Gln His Glu Leu Ile Lys Leu Ile
    1055               1060               1065

Ile Gln Lys Met Glu Ile Ile Ser Glu Thr Glu Asp Asp Ser
    1070               1075               1080

His Cys Ser Phe Gln Asp Arg Phe Lys Lys Glu Gln Met Glu Gln
    1085               1090               1095

Arg Asn Ser Arg Trp Asn Thr Val Leu Arg Ala Val Lys Ala Lys
    1100               1105               1110

Thr His His Leu Glu Pro
    1115

<210> SEQ ID NO 18
<211> LENGTH: 1119
<212> TYPE: PRT
<213> ORGANISM: Macaca mulatta

<400> SEQUENCE: 18

Met Lys Arg Ser Leu Arg Lys Met Trp Arg Pro Gly Glu Lys Lys Ala
1               5                   10                  15

Ser Gln Gly Val Val Tyr Glu Asp Val Gln Asp Thr Asp Asp Cys
            20                  25                  30

Lys Glu Thr Leu Lys Val Val Phe Glu Gly Ser Ala Tyr Gly Leu Gln
        35                  40                  45

Asn Tyr Asn Lys Gln Lys Lys Leu Lys Arg Cys Asp Asp Met Asp Thr
50                  55                  60

Phe Phe Leu His Tyr Ala Ala Ala Glu Gly Gln Ile Glu Leu Met Glu
65                  70                  75                  80

Lys Ile Thr Arg Asp Ser Ser Leu Glu Val Leu Asn Glu Met Asp Asp
                85                  90                  95

Tyr Gly Asn Thr Pro Leu His Cys Ala Val Glu Lys Asn Gln Ile Glu
            100                 105                 110

Ser Val Lys Phe Leu Leu Ser Arg Gly Ala Asn Pro Asn Leu Arg Asn
        115                 120                 125

Phe Asn Met Met Ala Pro Leu His Leu Ala Val Gln Gly Thr His Asn
    130                 135                 140

Glu Val Met Lys Val Leu Leu Glu His Arg Thr Ile Asp Ile Asn Leu
145                 150                 155                 160

Glu Gly Glu Asn Gly Asn Thr Ala Val Ile Ile Ala Cys Thr Thr Asn
                165                 170                 175
```

-continued

Asn Ser Glu Ala Leu Gln Ile Leu Leu Asn Lys Gly Ala Lys Pro Cys
                180                 185                 190

Lys Ser Asn Lys Trp Gly Cys Phe Pro Ile His Gln Ala Ala Phe Ser
            195                 200                 205

Gly Ser Lys Glu Cys Met Glu Ile Ile Leu Arg Phe Gly Glu His
        210                 215                 220

Gly Tyr Ser Arg Gln Leu His Ile Asn Phe Val Asn Asn Gly Lys Ala
225                 230                 235                 240

Ser Pro Leu His Leu Ala Val Gln Asn Gly Asp Leu Glu Met Ile Lys
                245                 250                 255

Met Cys Leu Asp Asn Gly Ala Gln Ile Asp Pro Val Glu Lys Gly Arg
            260                 265                 270

Cys Thr Ala Ile His Phe Ala Ala Thr Gln Gly Ala Thr Glu Ile Val
        275                 280                 285

Lys Leu Met Ile Ser Ser Tyr Ser Gly Ser Val Asp Ile Val Asn Thr
                290                 295                 300

Thr Asp Gly Ser His Glu Thr Met Leu His Arg Ala Ser Leu Phe Asp
305                 310                 315                 320

His His Glu Leu Ala Asp Tyr Leu Ile Ser Val Gly Ala Asp Ile Asn
                325                 330                 335

Lys Ile Asp Ser Glu Gly Arg Ser Pro Leu Ile Leu Ala Thr Ala Ser
            340                 345                 350

Ala Ser Trp Asn Ile Val Asn Leu Leu Leu Ser Lys Gly Ala Gln Val
        355                 360                 365

Asp Ile Lys Asp Asn Phe Gly Arg Asn Phe Leu His Leu Thr Val Gln
                370                 375                 380

Gln Pro Tyr Gly Leu Lys Asn Leu Arg Pro Glu Phe Met Gln Met Gln
385                 390                 395                 400

Gln Ile Lys Glu Leu Val Met Asp Glu Asp Asn Asp Gly Cys Thr Pro
                405                 410                 415

Leu His Tyr Ala Cys Arg Gln Gly Gly Pro Asp Ser Val Asn Asn Leu
            420                 425                 430

Leu Gly Phe Asn Val Ser Ile His Ser Lys Ser Lys Asp Lys Lys Ser
        435                 440                 445

Pro Leu His Phe Ala Ala Ser Tyr Gly Arg Ile Asn Thr Cys Gln Arg
    450                 455                 460

Leu Leu Gln Asp Ile Ser Asp Thr Arg Leu Leu Asn Glu Gly Asp Leu
465                 470                 475                 480

His Gly Met Thr Pro Leu His Leu Ala Ala Lys Asn Gly His Asp Lys
                485                 490                 495

Val Val Gln Leu Leu Leu Lys Lys Gly Ala Leu Phe Leu Ser Asp His
            500                 505                 510

Asn Gly Trp Thr Ala Leu His His Ala Ser Met Gly Gly Tyr Thr Gln
        515                 520                 525

Thr Met Lys Val Ile Leu Asp Thr Asn Leu Lys Cys Thr Asp Arg Leu
    530                 535                 540

Asp Glu Asp Gly Asn Thr Ala Leu His Phe Ala Ala Arg Glu Gly His
545                 550                 555                 560

Ala Lys Ala Val Ala Leu Leu Leu Ser His Asn Ala Asp Ile Val Leu
                565                 570                 575

Asn Lys Gln Gln Ala Ser Phe Leu His Leu Ala Leu His Asn Lys Arg
            580                 585                 590

Lys Glu Val Val Leu Thr Ile Ile Arg Ser Lys Arg Trp Asp Glu Cys

-continued

```
            595                 600                 605
Leu Lys Val Phe Ser His Asn Ser Pro Gly Asn Lys Cys Pro Ile Thr
610                 615                 620
Glu Met Ile Glu Tyr Leu Pro Glu Cys Met Lys Val Leu Leu Asp Phe
625                 630                 635                 640
Cys Met Leu His Ser Thr Glu Asp Lys Ser Cys Arg Asp Tyr Tyr Ile
                645                 650                 655
Glu Tyr Asn Phe Lys Tyr Leu Gln Cys Pro Leu Glu Phe Thr Lys Lys
                660                 665                 670
Thr Pro Thr Gln Asp Val Ile Tyr Glu Pro Leu Thr Ala Leu Asn Ala
                675                 680                 685
Met Val Gln Asn Asn Arg Ile Glu Leu Leu Asn His Pro Val Cys Lys
690                 695                 700
Glu Tyr Leu Leu Met Lys Trp Leu Ala Tyr Gly Phe Arg Ala His Met
705                 710                 715                 720
Met Asn Leu Gly Ser Tyr Cys Leu Gly Leu Ile Pro Met Thr Ile Leu
                725                 730                 735
Val Val Asn Ile Lys Pro Gly Met Ala Phe Asn Ser Thr Gly Ile Ile
                740                 745                 750
Asn Glu Thr Ser Asp His Ser Glu Ile Leu Asp Thr Thr Asn Ser Tyr
                755                 760                 765
Leu Ile Lys Thr Cys Met Ile Leu Val Phe Leu Ser Ser Ile Phe Gly
770                 775                 780
Tyr Cys Lys Glu Ala Gly Gln Ile Phe Gln Gln Lys Arg Asn Tyr Phe
785                 790                 795                 800
Met Asp Met Asn Asn Val Leu Glu Trp Ile Ile Tyr Thr Thr Gly Ile
                805                 810                 815
Ile Phe Val Leu Pro Leu Phe Val Glu Ile Pro Ala His Leu Gln Trp
                820                 825                 830
Gln Cys Gly Ala Ile Ala Val Tyr Leu Tyr Trp Met Asn Phe Leu Leu
                835                 840                 845
Tyr Leu Gln Arg Phe Glu Asn Cys Gly Ile Phe Ile Val Met Leu Glu
850                 855                 860
Val Ile Leu Lys Thr Leu Leu Arg Ser Thr Val Val Phe Ile Phe Leu
865                 870                 875                 880
Leu Leu Ala Phe Gly Leu Ser Phe Tyr Ile Leu Leu Asn Leu Gln Asp
                885                 890                 895
Pro Phe Ser Ser Pro Leu Leu Ser Ile Ile Gln Thr Phe Ser Met Met
                900                 905                 910
Leu Gly Asp Ile Asn Tyr Arg Glu Ser Phe Leu Glu Pro Tyr Leu Arg
                915                 920                 925
Asn Glu Leu Ala His Pro Leu Ser Phe Ala Gln Leu Ile Cys Phe
                930                 935                 940
Ala Ile Phe Val Pro Ile Val Leu Met Asn Leu Leu Ile Gly Leu Ala
945                 950                 955                 960
Val Gly Asp Ile Ala Glu Val Gln Lys His Ala Ser Leu Lys Arg Ile
                965                 970                 975
Ala Met Gln Val Glu Leu His Thr Ser Leu Glu Lys Lys Leu Pro Leu
                980                 985                 990
Trp Phe Leu Arg Lys Val Asp Gln Lys Ser Ile Ile Val Tyr Pro Asn
                995                 1000                1005
Lys Pro Arg Cys Gly Gly Leu Leu Phe His Ile Phe Tyr Phe Leu
                1010                1015                1020
```

```
Phe Cys Thr Gly Glu Ile Arg Gln Glu Ile Pro Asn Ala Asp Thr
    1025                1030                1035

Ser Leu Glu Met Glu Ile Leu Lys Gln Lys Tyr Arg Leu Lys Asp
    1040                1045                1050

Leu Thr Phe Leu Leu Glu Lys Gln His Glu Leu Ile Lys Leu Ile
    1055                1060                1065

Ile Gln Lys Met Glu Ile Ile Ser Glu Thr Glu Asp Glu Asp Asn
    1070                1075                1080

His Cys Ser Phe Gln Asp Arg Phe Lys Lys Glu Gln Met Glu Gln
    1085                1090                1095

Arg Asn Ser Arg Trp Asn Thr Val Leu Arg Ala Val Lys Ala Lys
    1100                1105                1110

Thr His His Leu Glu Pro
    1115

<210> SEQ ID NO 19
<211> LENGTH: 1010
<212> TYPE: PRT
<213> ORGANISM: Gallus gallus

<400> SEQUENCE: 19

Met Ser Asn Leu Asn Glu Val Asn Gly Thr Ile Lys Leu Lys Glu Val
1               5                   10                  15

Lys His Ala Leu Lys Cys Leu Asn Glu Gln Pro Tyr Lys Val Ile Ser
                20                  25                  30

Asp Gly Ser Ala Cys Arg Leu Arg Ser Phe Ile Lys Lys Asn Arg Ser
            35                  40                  45

Gly Leu Thr Lys Val Asp Glu Leu Asn Ala Thr Pro Leu His His Ala
        50                  55                  60

Ala Glu Gly Gly Gln Ile Glu Leu Met Gln Leu Ile Ile Asp Asp Ser
65                  70                  75                  80

Ser Ser Glu Val Leu Asn Val Met Asp Ser Ser Gly Asn Thr Pro Leu
                85                  90                  95

His Trp Ala Thr Arg Lys Asn Gln Val Glu Ser Val Arg Leu Leu Leu
                100                 105                 110

Ser Arg Gly Ala Asn Pro Asn Ile Leu Asn Ser Asn Met Met Ala Pro
            115                 120                 125

Leu His Met Ala Ile Gln Ser Leu His Asn Glu Ile Val Lys Ile Leu
        130                 135                 140

Val Gln His Ser Ser Thr Asp Val Asn Leu Glu Gly Glu Ala Gly Asn
145                 150                 155                 160

Thr Pro Ile Ile Val Ala Cys Tyr Lys Asp Asn Pro Glu Ala Leu Thr
                165                 170                 175

Phe Leu Ile Glu Asn Gly Gly Lys Ile Cys Lys Pro Asn Lys Thr Gly
                180                 185                 190

Cys Met Pro Ile His Ala Ala Ala Phe Ser Gly Ala Lys Thr Cys Met
            195                 200                 205

Glu Ile Leu Leu Lys Lys Gly Glu Glu Leu Gly His Ser Ala Lys Thr
        210                 215                 220

His Ile Asn Phe Thr Asn Asn Gly Lys Cys Ser Pro Leu His Leu Ala
225                 230                 235                 240

Val Gln Ser Gly Asp Leu Glu Met Ile Lys Met Cys Ile Glu Phe Gly
                245                 250                 255

Ala Gln Ile Asp Leu Lys Gln Asn Glu Lys Cys Thr Ala Leu His Phe
```

-continued

```
                260                 265                 270
Ala Ala Thr Gln Gly Ala Thr Glu Ile Val Lys Leu Met Met Ser Ser
            275                 280                 285
Tyr Ala Gly Asp Glu Ser Ile Ile Asp Ala Val Asp Gly Asn Lys Glu
290                 295                 300
Thr Leu Leu His Arg Thr Ala Leu Phe Asp His Tyr Glu Leu Ala Glu
305                 310                 315                 320
Tyr Leu Ile Ser Thr Gly Ala Asn Ile Asp Ser Val Asp Thr Glu Gly
                325                 330                 335
Arg Ser Pro Leu Leu Ala Thr Ser Cys Ala Ser Trp Lys Ile Val
                340                 345                 350
Asn Leu Leu Leu Ser Lys Gly Ala Asn Val Ser Leu Lys Asp His Leu
            355                 360                 365
Gly Arg Asn Phe Leu His Leu Thr Val Leu Gln Pro Gly Gly Leu Gln
        370                 375                 380
His Leu Asn Glu Lys Phe Leu Gln Met Glu His Ile Lys Asn Leu Val
385                 390                 395                 400
Val Asp Glu Asp Asn Glu Gly Cys Thr Pro Leu His Tyr Ala Cys Arg
                405                 410                 415
Gln Gly Val Ala Leu Ser Val Asn Asn Leu Leu Ser Leu Asn Val Ser
                420                 425                 430
Ile Tyr Ser Lys Ser Arg Asp Lys Lys Ser Pro Leu His Phe Ala Ala
            435                 440                 445
Ser Tyr Gly Arg Ile Asn Thr Cys Gln Arg Leu Ile Arg Asp Met Lys
        450                 455                 460
Asp Thr Arg Leu Leu Asn Glu Gly Asp Lys Lys Gly Met Thr Pro Leu
465                 470                 475                 480
His Leu Ala Ala Gln Asn Gly His Glu Lys Val Val Gln Phe Leu Leu
                485                 490                 495
Lys Arg Gly Ala Leu Phe Leu Cys Asp Tyr Lys Gly Trp Thr Ala Leu
            500                 505                 510
His His Ala Ala Phe Gly Gly Tyr Thr Arg Thr Met Gln Ile Ile Leu
        515                 520                 525
Asp Thr Asn Val Lys Cys Thr Asp Lys Val Asp Glu Glu Gly Asn Thr
        530                 535                 540
Ala Leu His Leu Ala Ala Lys Glu Gly His Ala Lys Ala Val Arg Leu
545                 550                 555                 560
Leu Leu Asp Tyr Gly Ala Lys Ile Leu Leu Asn Lys Ala Val Ala Ser
                565                 570                 575
Phe Phe His Glu Ala Ile His Asn Arg Arg Lys Asp Val Val Ser Thr
            580                 585                 590
Val Ile Leu His Lys Arg Trp Glu Glu Ala Val Leu Thr Phe Ser His
        595                 600                 605
Tyr Ser Ser Ala Asn Lys Cys Pro Leu Leu Glu Met Ile Glu Tyr Leu
        610                 615                 620
Pro Asp Ser Phe Lys Leu Val Leu Asp Asn Cys Ile Ile Glu Ser Ser
625                 630                 635                 640
Glu Glu Lys Thr Ser Arg Asp Phe Tyr Ile Glu Tyr Asn Phe Arg Tyr
                645                 650                 655
Leu Gln Cys Pro Leu Ala Leu Asn Arg Lys Leu Lys Glu Ala Glu Asp
                660                 665                 670
Ile Phe Tyr Glu Pro Leu Ala Ile Leu Asn Ala Met Val Arg His Asn
            675                 680                 685
```

```
Arg Met Glu Leu Leu Ser His Pro Val Cys Lys Glu Tyr Leu Leu Met
    690                 695                 700

Lys Trp Met Ala Tyr Gly Phe Arg Ala His Leu Met Asn Leu Gly Ile
705                 710                 715                 720

Tyr Ser Leu Gly Leu Ile Pro Leu Thr Leu Leu Val Thr His Ile Gln
                725                 730                 735

Pro Gly Arg Pro Leu Asn Gly Thr Glu Ile Tyr Glu Ala Arg Pro Leu
            740                 745                 750

Glu Tyr Glu Val Leu Thr Thr Asp Ser Tyr Phe Thr Arg Val Cys Met
        755                 760                 765

Cys Leu Val Leu Ile Met Ser Leu Leu Gly Ile Cys Lys Glu Ile Phe
    770                 775                 780

Gln Leu Ile Gln Gln Lys Leu Lys Tyr Leu Leu Asp Tyr Ser Asn Leu
785                 790                 795                 800

Leu Asp Trp Thr Ile Tyr Ser Thr Ser Ile Ile Phe Val Ser Ser Leu
                805                 810                 815

Phe Ile Asn Thr Pro Ala His Leu Gln Trp Glu Cys Gly Ala Ile Ala
            820                 825                 830

Val Tyr Leu Ser Trp Met Asn Phe Leu Leu Tyr Leu Gln Arg Phe Glu
        835                 840                 845

Asn Tyr Gly Ile Tyr Val Val Met Phe Trp Glu Ile Leu Arg Thr Leu
    850                 855                 860

Ile Arg Ile Ala Val Val Phe Phe Leu Ile Leu Ala Phe Gly Leu
865                 870                 875                 880

Ser Phe Phe Val Leu Leu Gly Ser Gln Gln Thr Tyr Ser Thr Pro Leu
                885                 890                 895

Leu Ser Val Met Lys Thr Phe Ala Met Met Leu Gly Asp Ile Asn Tyr
            900                 905                 910

His Asp Ala Phe Leu Asp Pro Leu Leu Ser Ser Glu Leu Pro Tyr Pro
        915                 920                 925

Phe Leu Ser Tyr Thr Val Leu Ile Ile Phe Thr Leu Leu Ile Pro Ile
    930                 935                 940

Leu Leu Met Asn Leu Leu Ile Gly Leu Ala Val Gly Asp Ile Ala Glu
945                 950                 955                 960

Val Gln Lys Tyr Ala Ala Leu Lys Arg Ile Ala Met Gln Val Asn Leu
                965                 970                 975

His Thr Asn Leu Glu Lys Lys Leu Pro Phe Trp Phe Leu Ser Arg Val
            980                 985                 990

Asp Gln Glu Ser Ile Thr Val Tyr Pro Asn Arg Pro Arg Tyr Cys Gly
        995                 1000                1005

Phe Met
    1010

<210> SEQ ID NO 20
<211> LENGTH: 1115
<212> TYPE: PRT
<213> ORGANISM: Danio rerio

<400> SEQUENCE: 20

Met Thr Lys Lys Met Thr His Ile Ser Lys Ser Glu Lys Ser Arg Gln
1                   5                   10                  15

Gln Ser Tyr Asp Asn Val Met Asp Gly Asp Glu Ser Asn Gln Ile Ser
                20                  25                  30

Ala Asn Val Phe Glu Trp Thr Lys Gln Gly Asn Ala Ala Ala Leu Glu
```

```
                    35                  40                  45
Lys Asn Ser Arg Tyr Leu Asp Thr Arg Asp Asn Ile Gly Ala Ser Pro
             50                  55                  60

Leu His Tyr Ala Ser Ala Asn Gly His Phe Arg Ile Ile Arg His Ile
 65                  70                  75                  80

Val Gln Ile Val Gly His Gln Glu Leu Asn Val Arg Asp Glu Glu Gly
                     85                  90                  95

Asn Thr Pro Leu His Trp Ala Val Gln Lys Asp Gln Pro Gly Ser Cys
                    100                 105                 110

Ser Val Leu Leu Ser Leu Gly Ala Asp Pro Asn Val Leu Asn Asn Ser
                115                 120                 125

His Gln Ala Pro Ile His Met Ala Val Ser Leu Gly Lys Asn Phe Val
            130                 135                 140

Leu Glu Gln Leu Val Ser His Lys Gln Thr Asp Val Asn Leu Glu Gly
145                 150                 155                 160

Asp Leu Gly Asn Thr Pro Val Ile Leu Ser Ala Ala Leu Asp Asn His
                165                 170                 175

Glu Ala Leu Gly Ile Leu Tyr Lys His Gly Ala Lys Phe Cys Arg Gln
                180                 185                 190

Asn Asn Leu Gly His Phe Pro Ile His Ala Ala Ala Phe Ser Gly Ala
            195                 200                 205

Lys Lys Ser Met Glu Val Ile Leu Leu Lys Gly Glu Glu Ala Gly Leu
210                 215                 220

Ser Ile Asp Ala His Ile Asn Tyr Val Asp Lys Ser Cys Ser Ser Pro
225                 230                 235                 240

Leu His Leu Ala Val Arg Gly Gly Asn Leu Asp Ile Ile Lys Leu Cys
                245                 250                 255

Ile Gly Tyr Gly Ala Lys Ile Asp Gln Gln Gln Cys Asp Lys Ser Thr
                260                 265                 270

Ala Leu His Phe Ala Cys Ser Gln Gly Ala Thr Glu Val Val Lys Val
            275                 280                 285

Met Leu Ser Ser Tyr Pro Lys Val Cys Asp Leu Ile Asn Ile Thr Asp
290                 295                 300

Gly Ala Asn Gln Thr Pro Leu His Lys Ala Val Ile Phe Asp His Phe
305                 310                 315                 320

Glu Leu Ser Glu Tyr Leu Met Ser Gln Gly Ala Asn Ile Asp Phe Val
                325                 330                 335

Asp Cys Lys Gly His Ser Pro Leu Leu Leu Ala Thr Ser Cys Gly Ala
            340                 345                 350

Trp Arg Thr Val Asn Leu Leu Leu Ser His Gly Ala Asp Leu Thr Lys
            355                 360                 365

Lys Asp Lys Ser Gly Cys Asn Phe Leu His Leu Ala Ile Leu Gln Pro
        370                 375                 380

Arg Gly Leu Lys Asn Leu Pro Thr Glu Val Leu Gln His Glu Ser Val
385                 390                 395                 400

Arg Glu Leu Leu Asn Asp Glu Asp Ile Glu Gly Cys Thr Pro Leu His
                405                 410                 415

Tyr Ala Cys Arg Leu Gly Ile Pro Asp Ser Val Lys Asn Met Leu Gly
                420                 425                 430

Leu Glu Val Ser Leu Asp Gln Lys Ser Lys Glu Lys Lys Ser Ala Leu
            435                 440                 445

His Phe Ala Ala Glu Phe Gly Arg Ile Asn Thr Cys His Arg Leu Leu
            450                 455                 460
```

```
Glu Met Val Thr Asp Thr Arg Leu Leu Asn Glu Gly Asp Glu Lys Gly
465                 470                 475                 480

Leu Thr Pro Leu His Leu Ala Ser Arg Glu Gly His Val Lys Val Val
            485                 490                 495

Glu Leu Leu Leu Arg Lys Gly Ala Leu Phe His Ser Asp Tyr Arg Gly
                500                 505                 510

Trp Ser Gly Leu His His Ala Ala Ser Glu Gly Tyr Thr Gln Thr Met
            515                 520                 525

Asp Thr Leu Leu Thr Ser Asn Ile Lys Leu Leu Asn Lys Thr Asp Gly
            530                 535                 540

Asp Gly Asn Thr Ala Leu His Leu Ala Ala Arg Ala Gly His Val Ala
545                 550                 555                 560

Ala Val Arg Leu Leu Leu Tyr Arg Gly Ala Lys Ile Ile Leu Asn Lys
                565                 570                 575

Asn Asp Ala Ser Phe Leu His Glu Ala Val His Asn Ala Arg Arg Glu
                580                 585                 590

Val Thr Asn Met Val Ile Glu Ser Asp Arg Cys Glu Ala Met Thr
                595                 600                 605

Thr Tyr Lys Pro Asn Ser Thr Lys Arg Cys Ile Val Met Asp Met Ile
            610                 615                 620

Glu Phe Leu Pro Glu Ser Phe Lys His Leu Leu Asp Thr Cys Ile Arg
625                 630                 635                 640

Glu Ser Glu Glu Asp Val Asn Cys Thr Asn Tyr Tyr Ile Glu Tyr Asn
                645                 650                 655

Phe Arg Trp Leu Gln His Pro Leu Gln Asn Leu Lys Lys Thr Gly Met
                660                 665                 670

Glu Lys Asp Met Ala Tyr Lys Pro Leu Ser Ala Leu Asn Ala Met Val
            675                 680                 685

Asn Phe Asn Arg Val Asn Leu Leu Thr His Pro Val Cys Lys Lys Tyr
            690                 695                 700

Leu Glu Met Lys Trp Ser Ala Tyr Gly Ile Lys Ala His Leu Leu Asn
705                 710                 715                 720

Met Thr Val Tyr Ala Leu Gly Val Phe Pro Leu Thr Tyr Leu Ile Val
                725                 730                 735

Asn Leu Lys Pro Thr Leu Val Thr Ser Arg Asn Val Thr Ser Val Asn
            740                 745                 750

Met Val Cys Thr Ser Leu Tyr Lys Gln Ser Tyr Leu Thr Thr Ser Ser
            755                 760                 765

Met Leu Leu Val Leu Ala Met Asn Met Tyr Ala Val Gly Lys Glu Ile
            770                 775                 780

Leu Gln Met Phe Gln Gln Arg Leu Asn Tyr Leu Arg Asp Leu Ser Asn
785                 790                 795                 800

Tyr Met Asp Trp Ala Ala Ala Ile Cys Ala Leu Leu Phe Val Val Pro
                805                 810                 815

Leu Leu Met Asn Leu Lys Ser Ser Trp His Trp Gln Ala Gly Ala Leu
            820                 825                 830

Ala Ala Leu Thr Ser Trp Leu Asn Leu Leu Tyr Leu Gln Arg Phe
            835                 840                 845

Glu Arg Ile Gly Ile Tyr Val Val Met Phe Arg Glu Ile Ser Arg Thr
            850                 855                 860

Leu Leu Ser Ile Ile Val Leu Phe Phe Tyr Leu Ile Leu Gly Phe Ala
865                 870                 875                 880
```

```
Leu Ser Phe Tyr Ala Leu Met Ile Glu Gln Gln His Phe Gly Arg Met
                885                 890                 895

Phe Leu Ser Leu Leu Gln Thr Phe Val Met Met Val Gly Glu Met Asn
            900                 905                 910

Tyr Gln Asp Asn Phe Met Lys Pro Tyr Leu Gln Gly Asp Leu Pro Phe
            915                 920                 925

Pro Asp Leu Thr Leu Ala Ile Phe Val Trp Phe Val Leu Val Pro
            930                 935                 940

Ile Leu Leu Met Asn Leu Leu Ile Gly Leu Ala Val Gly Asp Ile Ala
945                 950                 955                 960

Glu Val Gln Thr Asn Ala Cys Leu Lys Arg Ile Ala Met Gln Ile Glu
            965                 970                 975

Leu His Thr Asn Leu Glu Glu Arg Leu Pro Tyr Trp Phe Met Lys Arg
            980                 985                 990

Val Asp Gln Val Thr Ile Arg Glu Tyr Pro Asn Arg Cys Phe Ser Gly
            995                 1000                1005

Lys Lys Arg Trp Phe Phe Gly Gly Asn Glu Val Lys Ser Arg Thr
        1010                1015                1020

Arg Leu Gly Pro Thr Phe His Gln Leu Thr Pro Leu Glu Arg Glu
        1025                1030                1035

Leu Thr Lys Gln Lys Tyr Arg Leu Lys Glu Ile Ser Glu Thr Met
        1040                1045                1050

Glu Lys Gln His Asn Leu Leu Lys Leu Ile Val Gln Lys Met Glu
        1055                1060                1065

Ile Ser Ser Glu Ala Asp Glu His Asp Gly Pro Pro Val Phe Gln
        1070                1075                1080

Glu Leu Lys Glu Lys Leu Leu Thr Lys Ser Lys Trp Gly Pro Leu
        1085                1090                1095

Leu Arg Ala Val Thr Ala Arg Lys Lys Gly Ile Cys Ser Phe Gly
        1100                1105                1110

Lys Thr
    1115

<210> SEQ ID NO 21
<211> LENGTH: 1115
<212> TYPE: PRT
<213> ORGANISM: Danio rerio

<400> SEQUENCE: 21

Met Thr Lys Lys Met Thr His Ile Ser Lys Ser Glu Lys Ser Arg Gln
1               5                   10                  15

Gln Ser Tyr Asp Asn Val Met Asp Gly Asp Glu Ser Asn Gln Ile Ser
            20                  25                  30

Ala Asn Val Phe Glu Trp Thr Lys Gln Gly Asn Ala Ala Leu Glu
        35                  40                  45

Lys Asn Ser Arg Tyr Leu Asp Thr Arg Asp Asn Ile Gly Ala Ser Pro
    50                  55                  60

Leu His Tyr Ala Ser Ala Asn Gly His Phe Arg Ile Ile Arg His Ile
65                  70                  75                  80

Val Gln Ile Val Gly His Gln Glu Leu Asn Val Arg Asp Glu Glu Gly
                85                  90                  95

Asn Thr Pro Leu His Trp Ala Val Gln Lys Asp Gln Pro Gly Ser Cys
            100                 105                 110

Ser Val Leu Leu Ser Leu Gly Ala Asp Pro Asn Val Leu Asn Asn Ser
            115                 120                 125
```

```
His Gln Ala Pro Ile His Met Ala Val Ser Leu Gly Lys Asn Phe Val
    130                 135                 140

Leu Glu Gln Leu Val Ser His Lys Gln Thr Asp Val Asn Leu Glu Gly
145                 150                 155                 160

Asp Leu Gly Asn Thr Pro Val Ile Leu Ser Ala Leu Asp Asn His
                165                 170                 175

Glu Ala Leu Gly Ile Leu Tyr Lys His Gly Ala Lys Phe Cys Arg Gln
                180                 185                 190

Asn Asn Leu Gly His Phe Pro Ile His Ala Ala Ala Phe Ser Gly Ala
        195                 200                 205

Lys Lys Ser Met Glu Val Ile Leu Leu Lys Gly Glu Glu Ala Gly Leu
    210                 215                 220

Ser Ile Asp Ala His Ile Asn Tyr Val Asp Lys Ser Cys Ser Ser Pro
225                 230                 235                 240

Leu His Leu Ala Val Arg Gly Gly Asn Leu Asp Ile Ile Lys Leu Cys
                245                 250                 255

Ile Gly Tyr Gly Ala Lys Ile Asp Gln Gln Cys Asp Lys Ser Thr
                260                 265                 270

Ala Leu His Phe Ala Cys Ser Gln Gly Ala Thr Glu Val Val Lys Val
        275                 280                 285

Met Leu Ser Ser Tyr Pro Lys Val Cys Asp Leu Ile Asn Ile Thr Asp
    290                 295                 300

Gly Ala Asn Gln Thr Pro Leu His Lys Ala Val Ile Phe Asp His Phe
305                 310                 315                 320

Glu Leu Ser Glu Tyr Leu Met Ser Gln Gly Ala Asn Ile Asp Phe Val
                325                 330                 335

Asp Cys Lys Gly His Ser Pro Leu Leu Leu Ala Thr Ser Cys Gly Ala
                340                 345                 350

Trp Arg Thr Val Asn Leu Leu Leu Ser His Gly Ala Asp Leu Thr Lys
            355                 360                 365

Lys Asp Lys Ser Gly Cys Asn Phe Leu His Leu Ala Ile Leu Gln Pro
    370                 375                 380

Arg Gly Leu Lys Asn Leu Pro Thr Glu Val Leu Gln His Glu Ser Val
385                 390                 395                 400

Arg Glu Leu Leu Asn Asp Glu Asp Ile Glu Gly Cys Thr Pro Leu His
                405                 410                 415

Tyr Ala Cys Arg Leu Gly Ile Pro Asp Ser Val Lys Asn Met Leu Gly
                420                 425                 430

Leu Glu Val Ser Leu Asp Gln Lys Ser Lys Glu Lys Ser Ala Leu
        435                 440                 445

His Phe Ala Ala Glu Phe Gly Arg Ile Asn Thr Cys His Arg Leu Leu
    450                 455                 460

Glu Met Val Thr Asp Thr Arg Leu Leu Asn Glu Gly Asp Glu Lys Gly
465                 470                 475                 480

Leu Thr Pro Leu His Leu Ala Ser Arg Glu Gly His Val Lys Val Val
                485                 490                 495

Glu Leu Leu Leu Arg Lys Gly Ala Leu Phe His Ser Asp Tyr Arg Gly
                500                 505                 510

Trp Ser Gly Leu His His Ala Ala Ser Glu Gly Tyr Thr Gln Thr Met
            515                 520                 525

Asp Thr Leu Leu Thr Ser Asn Ile Lys Leu Leu Asn Lys Thr Asp Gly
    530                 535                 540
```

-continued

```
Asp Gly Asn Thr Ala Leu His Leu Ala Ala Arg Ala Gly His Val Ala
545                 550                 555                 560

Ala Val Arg Leu Leu Leu Tyr Arg Gly Ala Lys Ile Ile Leu Asn Lys
                565                 570                 575

Asn Asp Ala Ser Phe Leu His Glu Ala Val His Asn Ala Arg Arg Glu
                580                 585                 590

Val Thr Asn Met Val Ile Glu Ser Asp Arg Cys Glu Glu Ala Met Thr
            595                 600                 605

Thr Tyr Lys Pro Asn Ser Thr Lys Arg Cys Ile Val Met Asp Met Ile
        610                 615                 620

Glu Phe Leu Pro Glu Ser Phe Lys His Leu Leu Asp Thr Cys Ile Arg
625                 630                 635                 640

Glu Ser Glu Glu Asp Val Asn Cys Thr Asn Tyr Tyr Ile Glu Tyr Asn
                645                 650                 655

Phe Arg Trp Leu Gln His Pro Leu Gln Asn Leu Lys Lys Thr Gly Met
            660                 665                 670

Glu Lys Asp Met Ala Tyr Lys Pro Leu Ser Ala Leu Asn Ala Met Val
        675                 680                 685

Asn Phe Asn Arg Val Asn Leu Leu Thr His Pro Val Cys Lys Lys Tyr
690                 695                 700

Leu Glu Met Lys Trp Ser Ala Tyr Gly Ile Lys Ala His Leu Leu Asn
705                 710                 715                 720

Met Thr Val Tyr Ala Leu Gly Val Phe Pro Leu Thr Tyr Leu Ile Val
                725                 730                 735

Asn Leu Lys Pro Thr Leu Val Thr Ser Arg Asn Val Thr Ser Val Asn
            740                 745                 750

Met Val Cys Thr Ser Leu Tyr Lys Gln Ser Tyr Leu Thr Thr Ser Ser
        755                 760                 765

Met Leu Leu Val Leu Ala Met Asn Met Tyr Ala Val Gly Lys Glu Ile
770                 775                 780

Leu Gln Met Phe Gln Gln Arg Leu Asn Tyr Leu Arg Asp Leu Ser Asn
785                 790                 795                 800

Tyr Met Asp Trp Ala Ala Ala Ile Cys Ala Leu Leu Phe Val Val Pro
                805                 810                 815

Leu Leu Met Asn Leu Lys Ser Ser Trp His Trp Gln Ala Gly Ala Leu
            820                 825                 830

Ala Ala Leu Thr Ser Trp Leu Asn Leu Leu Tyr Leu Gln Arg Phe
        835                 840                 845

Glu Arg Ile Gly Ile Tyr Val Val Met Phe Arg Glu Ile Ser Arg Thr
850                 855                 860

Leu Leu Ser Ile Ile Val Leu Phe Phe Tyr Leu Ile Leu Gly Phe Ala
865                 870                 875                 880

Leu Ser Phe Tyr Ala Leu Met Ile Glu Gln Gln His Phe Gly Arg Met
                885                 890                 895

Phe Leu Ser Leu Leu Gln Thr Phe Val Met Met Val Gly Glu Met Asn
            900                 905                 910

Tyr Gln Asp Asn Phe Met Lys Pro Tyr Leu Gln Gly Asp Leu Pro Phe
        915                 920                 925

Pro Asp Leu Thr Leu Ala Ile Phe Val Trp Phe Val Leu Leu Val Pro
930                 935                 940

Ile Leu Leu Met Asn Leu Leu Ile Gly Leu Ala Val Gly Asp Ile Ala
945                 950                 955                 960

Glu Val Gln Thr Asn Ala Cys Leu Lys Arg Ile Ala Met Gln Ile Glu
```

```
                965                 970                 975
Leu His Thr Asn Leu Glu Glu Arg Leu Pro Tyr Trp Phe Met Lys Arg
                980                 985                 990
Val Asp Gln Val Thr Ile Arg Glu Tyr Pro Asn Arg Cys Phe Ser Gly
                995                1000                1005
Lys Lys Arg Trp Phe Phe Gly Gly Asn Glu Val Lys Ser Arg Thr
    1010                1015                1020
Arg Leu Gly Pro Thr Phe His Gln Leu Thr Pro Leu Glu Arg Glu
    1025                1030                1035
Leu Thr Lys Gln Lys Tyr Arg Leu Lys Glu Ile Ser Glu Thr Met
    1040                1045                1050
Glu Lys Gln His Asn Leu Leu Lys Leu Ile Val Gln Lys Met Glu
    1055                1060                1065
Ile Ser Ser Glu Ala Asp Glu His Asp Gly Pro Pro Val Phe Gln
    1070                1075                1080
Glu Leu Lys Glu Lys Leu Leu Thr Lys Ser Lys Trp Gly Pro Leu
    1085                1090                1095
Leu Arg Ala Val Thr Ala Arg Lys Lys Gly Ile Cys Ser Phe Gly
    1100                1105                1110
Lys Thr
    1115
```

US 9,986,740 B2

METHODS OF IDENTIFYING INSECT-TRPA1 MODULATORS

CROSS-REFERENCED TO RELATED APPLICATIONS

This application is a divisional application of U.S. patent application Ser. No. 13/635,494, filed May 9, 2013, Allowed, which is the U.S. national phase application pursuant to 35 U.S.C. § 371, of PCT International Application Ser. No. PCT/US2011/028853, filed Mar. 17, 2011, which claims the benefit of and priority to U.S. Provisional Application No. 61/314,905, filed Mar. 17, 2010. The entire contents of the aforementioned patent applications are incorporated herein by this reference.

GOVERNMENT SUPPORT

This invention was made with government support under R21 MH080206, R01 MH067284 and P01 NS044232 awarded by the National Institutes of Health. The Government has certain rights in the invention.

BACKGROUND OF INVENTION

Insects cause great losses and damages to human agriculture, food supply, post-harvest storage, horticulture, animal health and public health. While advances have been made in the control of these insects, these insects have been able to adapt and evade the control measures.

Animals from flies to humans are equipped with biological sensors for sensing the environment and its changes, and help dictate the behavioral response to the environmental changes. Accordingly, there remains a need for methods identifying compounds that are species specific modulators of biological sensors.

SUMMARY OF THE INVENTION

In one aspect the invention provides a method of identifying insect-specific TRPA1 modulator comprising: (a) contacting a test compound with an insect TRPA1 and a mammalian TRPA1; and (b) assaying modulation of insect and mammalian TRPA1 activity.

In another aspect the invention provides a method of insect control comprising modulating chemo- and/or thermo-sensing in an insect with a compound identified by the methods described herein.

BRIEF DESCRIPTION OF THE DRAWINGS

In FIG. 1D, for each TrpA1 allel: upper bar (light), first offering; lower bar (dark), second to fifth offerings combined. Statistically distinct groups marked by different letters (Tukey HSD, $\alpha=0.01$). Data are mean+/−SEM. All studies use 12% (350 mM) sucrose, alone or with 100 mM caffeine, 2 mM AITC, 10 mM NMM, or 6 mM CA. n=3 groups of ≥7 flies, unless noted.

In FIGS. 2A and 2B, for each construct: upper bar (light), first offering; lower bar (dark), second to fifth offerings combined.

FIGS. 3F and 3G show ectopic dTRPA1 expression confers electrophile sensitivity upon motor neurons. Motor neuron-driven excitatory junction potentials (EJPs) from third instar larval muscles (FIG. 3F) and mean EJP frequencies (FIG. 3G). In controls, no EJPs were observed.

In FIGS. 6A-6C, +60 mV (o) and −60 mV (●).

DETAILED DESCRIPTION OF THE INVENTION

Figure 1A:
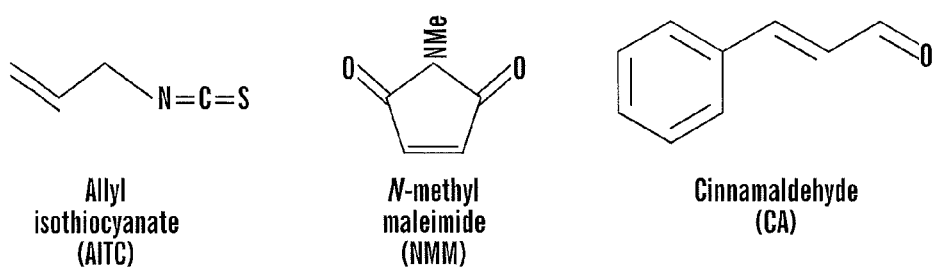
FIGS. 1A-1D show that dTrpA1 mediates gustatory responses to reactive electrophiles. Chemical structures of allyl isothiocyanate (AITC), N-methyl-maleimide (NMM) and cinnamaldehyde (CA) (FIG. 1A). Proboscis extension response (PER) frequency at five sequential tastant offerings, ingestion permitted, for wild type (-●-) and dTrpA1$^{ins}$ (-■-) (FIG. 1B); $*p<0.05$, $**p<0.01$, unpaired t-test). PER frequency when tastant contacts only legs (FIG. 1C). Five sequential offerings combined (n≥10 flies). PER frequency when ingestion permitted (FIG. 1D).

TRPA1 is a non-selective cation channel belonging to the larger family of TRP ion channels. The TRP channels constitute a large and important class of channels involved in modulating cellular homeostasis. TRP channels have been classified into at least six groups: TRPC (short), TRPV (vanilloid), TRPM (long, melastatin), TRPP (polycystins), TRPML (mucolipins), and TRPA (ANKTM1). The TRPC group can be divided into 4 subfamilies (TRPC1, TRPC4,5, TRPC3,6,7 and TRPC2) based on sequence homology and functional similarities. Currently the TRPV family has 6 members. TRP V5 and TRP V6 are more closely related to each other than to TRPV1, TRP V2, TRPV3, or TRPV4. TRPA1 is most closely related to TRPV3, and is more closely related to TRPV1 and TRPV2 than to TRPV5 and TRPV6. The TRPM family has 8 members. Constituents include the following: the founding member TRPM1 (Melastatin or LTRPC1), TRPM3 (KIAA1 616 or LTRPC3), TRPM7 (TRP-PLIK, ChaK(1), LTRPC7), TRPM6 (ChaK2), TRPM2 (TRPC7 or LTRPC2), TRPM8 (Trp-p8 or CMR1), TRPM5 (Mtr1 or LTRPC5), and TRPM4 (F1120041 or LTRPC4). The sole mammalian member of the TRPA family is ANKTM1. The TRPML family consists of the mucolipins, which include TRPML1 (mucolipins 1), TRPML2 (mucolipins 2), and TRPML3 (mucolipin3). The TRPP family consists of two groups of channels: those predicted to have six transmembrane domains and those that have 11. TRPP2 (PKD2), TRPP3 (PKD2L1), TRPP5 (PKD2L2) are all predicted to have six transmembrane domains. TRPP1(PKD13 PC1)5 PKD-REJ and PKD-IL1 are all thought to have 11 transmembrane domains. The TRPA1 is expressed in a great number or organisms: mammals (humans, mice, rats, monkeys and chimpanzee), zebrafish, insects (*Drosophila, Tribolium, Pediculus, Culex, Anopheles*), and red jungle fowl to name a few.

The inventors have discovered that the Transient Receptor Potential ion channel A1 (TRPA1) exhibits species specific differences in response to different chemical compounds. Accordingly, in one aspect the invention provides a method of identifying an insect-specific TRPA1 modulator comprising: (a) contacting a test compound with an insect TRPA1 and a mammalian TRPA1; (b) assaying activation of the insect and mammalian TRPA1.

In some embodiments, the method further comprises the step of comparing the activation of the insect TRPA1 with the mammalian TRPA1.

In some embodiments, the method also comprises the step of selecting the compound which preferentially modulates the insect TRPA1 relative to the mammalian TRPA1.

Activation of TRPA1 can be assayed using conventional in vitro and in vivo methods well known to the skilled artisan, such as the two-electrode voltage clamping on *Xenopus lavis* oocytes or EJP frequency measuring in larval neuromuscular junctions as described herein. Other methods of assaying TRPA1 activation include those described in Hinman, et al., *Proc. Natil. Acad. Sci. USA*, 103: 19564-19568 (2006); Macpherson, et al., *Nature*, 445: 541-445 (2007); Hamada, et al., *Nature*, 454: 217-220 (2008); Xiao, et al., *J. Neurosci.* 28: 9640-9651 (2008); Talvara, Talavera, et al., *Nature Neurosci.* 12, 1293-1299 (2009); and Int. Pat. App. No. PCT/US09/46933, filed Jun. 10, 2009, content of all of which is herein incorporated by reference. For example, the channel activity of TRPA1 can be assayed using a variety of assays to measure changes in ion fluxes including patch clamp techniques, measurement of whole cell currents, radiolabeled ion flux assyas, and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Hoevinsky et al., *J. Membrane Biol.* 137:59-70 (1994)). For example, a nucleic acid encoding a TRPA1 protein or homolog thereof can be injected into *Xenopus* oocytes. Channel activity can then be assessed by measuring changes in membrane polarization, i.e., changes in membrane potential. One means to obtain electrophysiological measurements is by measuring currents using patch clamp techniques, e.g., the "cell-attached" mode, the "inside-out" mode, and the "whole cell" mode (see, e.g., Ackerman et al., *New Engl. J. Med.* 336: 1575-1595, 1997). Whole cell currents can be determined using standard methodology such as that described by Hamil et al., *PFlugers. Archiv.* 391:185 (1981).

Channel activity is also conveniently assessed by measuring changes in intracellular $Ca^{2+}$ levels. Such methods are well known in the art. For example, calcium flux can be measured by assessment of the uptake of $Ca^{2+}$ or by using fluorescent dyes such as Fura-2. In a typical microfluorimetry assay, a dye such as Fura-2, which undergoes a change in fluorescence upon binding a single $Ca^{2+}$ ion, is loaded into the cytosol of TRPM8-expressing cells. Upon exposure to a test compound, an increase in cytosolic calcium is reflected by a change in fluorescence of Fura-2 that occurs when calcium is bound.

The activity of TRPA1 can be also assessed using a variety of other in vitro and in vivo assays to determine functional, chemical, and physical effects, e.g., measuring the binding of TRPA1 to other molecules, including peptides, small organic molecules, and lipids; measuring TRPA1 protein and/or RNA levels, or measuring other aspects of TRPA1 polypeptides, e.g., transcription levels, or physiological changes. When the functional consequences are determined using intact cells or animals, one can also measure a variety of effects such as changes in cell growth or pH changes or changes in intracellular second messengers such as IP3, cGMP, or cAMP, or components or regulators of the phospholipase C signaling pathway.

Generally, a compound can be tested at any concentration that can modulate the activity of insect TRPA1 over an appropriate time period. In some embodiments, the compound is tested at a concentration in the range of about 0.1 nM to about 1000 mM. Preferably the compound is tested in the range of about 100 µM to about 1000 µM. In one non-limiting example, the compound is tested at 0.05 mM, 0.1 mM, 0.2 mM, 0.3 mM, 0.4 mM, 0.5 mM, 0.6 mM, 0.7 mM, 0.8 mM, 0.9 mM, 1 mM, 1.1 mM, 1.2 mM, 1.3 mM, 1.4 mM, 1.5 mM, 1.6 mM, 1.7 mM, 1.8 mM, 1.0 mM, or 2 mM.

In some embodiments, the compound is tested at two or more different concentrations. Preferably the highest concentration tested is at least 2×, at least 3×, at least 4×, at least 5×, at least 6×, at least 7×, at least 8×, at least 9×, at least 10×, at least 250×, at least 25×, at least 50×, at least 75×, at least 100× higher than the lowest concentration employed. For a non-limiting example, the compound is tested at 0.1 mM, 0.5 mM, and 1 mM.

Generally, a compound can be contacted with insect and/or mammalian TRPA1 for any length of time before measuring and activity of said TRPA1. For example, a compound can be contacted with insect and/or mammalian TRPA1 for at least 5 seconds, at least 10 seconds, at least 15 seconds, at least 30 seconds, at least 45 seconds, at least 1 minute, at least 2 minutes, at least 3 minutes, at least 4 minutes, at least 5 minutes, at least 10 minutes, at least 15 minutes, at least 30 minutes, at least 60 minutes, or more before activity of TRPA1 is measured. In some embodiments, activity is measured at the instant when the TRPA1 is contacted with a compound.

In some embodiments, activity is measured over a period of time. For example, activity can be measured for a period of at least 5 seconds, at least 10 seconds, at least 15 seconds, at least 30 seconds, at least 45 seconds, at least 1 minute, at least 2 minutes, at least 3 minutes, at least 4 minutes, at least 5 minutes, at least 10 minutes, at least 15 minutes, at least 30 minutes, at least 60 minutes, or more. The measurement period can start at the instant when the TRPA1 is first contacted with a compound or start after a period of time after the TRPA1 is first contacted with a compound. The TRPA1 can be continuously contacted with the compound while activity is measured.

In some embodiments, the method further comprising the step of selecting the test compound that preferentially modulates the insect TRPA1 relative to a mammalian TRPA1. By preferential modulation is meant that activity of insect TRPA1 is modulated by at least 5%, at least 10%, at least 20%, at least 30%, at least 40%, at least 50%, at least 60%, at least 70%, at least 80%, at least 90%, at least 95%, at least 100%, or more relative to the mammalian TRPA1.

In some embodiments, the test compound does not modulate the activity of the mammalian TRPA1, e.g., the tested compound has no significant effect on the mammalian TRPA1 activity.

In some embodiments, the test compound has an EC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM for activating an insect TRPA1.

In some embodiments, the compound has an IC50 of less than or equal to 500 nM, less than or equal to 250 nM, less than or equal to 100 nM, less than or equal to 50 nM, less than or equal to 10 nM, less than or equal to 1 nM, less than or equal to 0.1 nM, less than or equal to 0.01 nM, or less than or equal to 0.001 nM for inhibiting an insect TRPA1.

Without wishing to be bound by theory, identification of selective modulators of insect TRPA1s can maximize pest deterrence while minimizing irritation to other animals.

As used herein, the term "test compound" refers to the collection of compounds that are to be screened for their ability to specifically modulate insect TRPA1 while having little effect on mammalian TRPA1s. The test compounds of the invention encompass numerous classes of chemical molecules, e.g., small organic or inorganic molecules, polysaccharides, biological macromolecules, e.g., peptides, proteins, peptide analogs and derivatives, peptidomimetics, nucleic acids, nucleic acid analogs and derivatives, an extract made from biological materials such as bacteria, plants, fungi, or animal cells or tissues, naturally occurring or synthetic compositions. Generally, the test compounds can have a molecular weight of about 50 to 500,000.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

In some embodiments, the test compound is a synthetic molecule. By synthetic molecule is meant a molecule that does not occur in nature.

In some embodiment, the test compound is a naturally occurring molecule. Such a molecule can be used in a purified or unpurified form, i.e., as obtained from the biological source.

Depending upon the particular embodiment being practiced, the test compounds may be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, the test compounds may be screened individually, or in groups. Group screening is particularly useful where hit rates for effective test compounds are expected to be low such that one would not expect more than one positive result for a given group.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). A number of small molecule libraries are known in the art and commercially available. Commercially available compound libraries can be obtained from, e.g., ArQule, Pharmacopia, graffinity, Panvera, Vitas-M Lab, Biomol International and Oxford. These libraries can be screened using the screening methods described herein. Chemical compound libraries such as those from of 10,000 compounds and 86,000 compounds from NIH Roadmap, Molecular Libraries Screening Centers Network (MLSCN) can also be used. A comprehensive list of compound libraries can be found at www.broad.harvard.edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

In some embodiments, the insect TRPA1 is in a biological cell. In some embodiments, the mammalian TRPA1 is in a biological cell. The term "biological cell" or "cell" as used herein has its commonly understood meaning. Inside a cell, the TRPA1 can be expressed from an endogenous gene in the cell or a from a vector that is transfected into the cell. The skilled artisan is well aware of methods and protocols for transfecting cells with vectors for expressing proteins of interest.

The insect TRPA1 used in the screening assay can be any insect TRPA1 or homolog thereof. In some embodiments, the insect TRPA1 is selected from the group consisting of *D. melanogaster* TRPA1 isoform F (Accession No. ABW08500.3), *D. melanogaster* TRPA1 isoform E (Accession No. AAF50356.4), *D. melanogaster* TRPA1 isoform F (Accession No. NP_001097554.3), *D. melanogaster* TRPA1 isoform E (Accession No. NP_648263.4), *D. melanogaster* TRPA1 (Accession No. Q7Z020.3), *Anopheles gambiae* TRPA1 (Accession No. ACC86138.1), *Tribolium castaneum* hypothetical protein TcasGA2_TC002449 (Accession No. EFA01253.1), and conservative variants thereof.

The mammalian TRPA1 used in the screening assay can be any mammalian TRPA1 or homolog thereof. In some embodiments, the mammalian TRPA1 is selected from the group consisting of *Rattus norvegicus* transient receptor potential cation channel, subfamily A, member 1 (Accession No. NP_997491.1); *Rattus norvegicus* transient receptor potential cation channel subfamily A member 1 (Accession No. AAS78661.1); *Mus musculus* transient receptor potential cation channel, subfamily A, member 1 (Accession No. NP_808449.1); *Homo sapiens* transient receptor potential cation channel subfamily A member 1 (Accession No. NP_015628.2); *Mus musculus* transient receptor potential cation channel, subfamily A, member 1 (Accession No. AAI31964.1); *Mus musculus* transient receptor potential cation channel, subfamily A, member 1 (Accession No. AAI20564.1); *Mus musculus* transient receptor potential cation channel, subfamily A, member 1, isoform CRA_b (Accession No. EDL14332.1); *Mus musculus* transient receptor potential cation channel, subfamily A, member 1, isoform CRA_a (Accession No. EDL14331.1); *Bos Taurus* transformation sensitive protein p120 (Accession No. XP_581588.2); *Pan troglodytes* predicted ankyrin-like protein 1 (Accession No. XP_519806.2); *Macaca mulatta* predicted ankyrin-like protein 1 (Accession No. XP_001083172.1); *Gallaus gallus* predicted similar to transient receptor potential cation channel subfamily A member 1 (Accession No. XP_418294.2); *Danio rerio* TRPA1 (Accession No. AAV37177.1)*Danio rerio* transient receptor potential cation channel, subfamily A, member 1a (Accession No. NP_001007066.1), and conservative variants thereof.

As used herein, a "conservative variant" is an amino acid sequence in which a first amino acid is replaced by a second amino acid or amino acid analog having at least one similar biochemical property, which can be, for example, similar size, charge, hydrophobicity or hydrogen bonding capacity. For example, a first hydrophobic amino acid can be conservatively substituted with a second (non-identical) hydrophobic amino acid such as alanine, valine, leucine, or isoleucine, or an analog thereof. Similarly, a first basic amino acid can be conservatively substituted with a second (non-identical) basic amino acid such as arginine or lysine, or an analog thereof. In the same way, a first acidic amino acid can be conservatively substituted with a second (non-identical) acidic amino acid such as aspartic acid or glutamic acid, or an analog thereof or an aromatic amino acid such as phenylalanine can be conservatively substituted with a second aromatic amino acid or amino acid analog, for example tyrosine. In some embodiments, the peptide comprises conservative variant substitution of at least one amino acid, e.g. 1, 2, 3, 4, 5, 6, 7, 8, 9, 10 or more amino acids. Typically, a conservative variant will retain at least 50%, 55%, 60%, 65%, 70%, 75%, 80%, 85%, 90%, 95%, 97%, 98%, 99% or more of the activity of the wild-type peptide sequence.

Exemplary conservative variant substitution include, but are not limited to, replacement of Alanine (A) with D-ala, Gly, Aib, β-Ala, Acp, L-Cys, or D-Cys; Arginine (R) with D-Arg, Lys, D-Lys, homo-Arg, D-homo-Arg, Met, Ile, D-Met, or D-Ile; Asparagine (N) with D-Asn, Asp, D-Asp, Glu, D-Glu, Gln, or D-Gln; Aspartic acid (D) with D-Asp, D-Asn, Asn, Glu, D-Glu, Gln, or D-Gln; Cysteine (C) with D-Cys, S-Me-Cys, Met, D-Met, Thr, or D-Thr; Glutamine (Q) with D-Gln, Asn, D-Asn, Glu, D-Glu, Asp, or D-Asp; Glutamic Acid (E) with D-Glu, D-Asp, Asp, Asn, D-Asn, Gln, or D-Gln; Glycine (G) with Ala, D-Ala, Pro, D-Pro, Aib, β-Ala, aor Acp; Isoleucine (I) with D-Ile, Val, D-Val, AdaA, AdaG, Leu, D-Leu, Met, orD-Met; Leucine (L) with D-Leu, Val, D-Val, AdaA, AdaG, Leu, D-Leu, Met, or D-Met; Lysine (K) with D-Lys, Arg, D-Arg, homo-Arg, D-homo-Arg, Met, D-Met, Ile, D-Ile, Orn, or D-Orn; Methionine (M) with D-Met, S-Me-Cys, Ile, D-Ile, Leu, D-Leu, Val, or D-Val; Phenylalanine (F) with D-Phe, Tyr, D-Thr, L-Dopa, His, D-His, Trp, D-Trp, Trans-3,4 or 5-phenylproline, AdaA, AdaG, cis-3,4 or 5-phenylproline, Bpa, or D-Bpa; Proline (P) with D-Pro, L-I-thioazolidine-4-carboxylic acid, or D-or-L-1-oxazolidine-4-carboxylic acid (U.S. Pat. No. 4,511,390); Serine (S) with D-Ser, Thr, D-Thr, allo-Thr, Met, D-Met, Met (O), D-Met (O), L-Cys, or D-Cys; Threonine (T) with D-Thr, Ser, D-Ser, allo-Thr, Met, D-Met, Met (O), D-Met (O), Val, or D-Val; Tyrosine (Y) with D-Tyr, Phe, D-Phe, L-Dopa, His, or D-His; and Valine (V) with D-Val, Leu, D-Leu, Ile, D-Ile, Met, D-Met, AdaA, or AdaG.

Conservative variants of the TRPA1s can be prepared according to methods for altering peptide sequences known to one of ordinary skill in the art, and include those that are found in references which compile such methods, e.g., *Molecular Cloning: A Laboratory Manual*, J. Sambrook, et al., eds., Second Edition, Cold Spring Harbor, or *Current Protocols in Molecular Biology*, F. M. Ausubel, et al., eds., John Wiley & Sons, Inc. New York. Conservative variants of TRPA1 can also be made by alteration of a nucleic acid encoding the TRPA1 polypeptide.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976, 813; 6,472,144; 6,692,856; 6,824,982; and 7,091,048, and contents of each of these are herein incorporated by reference in their entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic, that features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as current or voltage measurements, colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

In another aspect, the invention provides a compound selected by the screening assay described herein. It is to be understood that analogs, derivatives, isomers, and pharmaceutically acceptable salts of the compounds selected by the screening assays described herein are also included herein.

The compound or group of compounds being selected by the method according to the invention can be used in methods of insect control, e.g. by modulating an environment sensing mechanism, for example modulating thermo- and/or chemo-sensing, in an insect. The identified compounds, analogs, derivatives, isomers, and pharmaceutically acceptable salts thereof are also referred to as active agents herein. While not wishing to be bound by theory, the modulation of TRPA1 elicits a signaling pathway that brings forth motor neuron modulation which can increase or decrease movement of an insect from a non-optimal environment. Accordingly, in one aspect the invention provides a method of insect control by modulating thermo- and/or chemo-sensing in an insect using a compound identified by the screening methods described herein. As used in context of methods of insect control, compounds identified by the screening methods described herein also include analogs, derivatives, isomers and pharmaceutically acceptable salts of such compounds.

In some embodiments, the compound modulates the thermo-sensing pathway of the insect. As used herein, the term "thermo-sensing pathway" refers to a signaling pathway involved in setting the preferred temperature in an insect. Without wishing to be bound by theory, activation of the thermo-sensing pathway allows an insect or non-insect pest to move from a non-preferred temperature (hot or cold) to a preferred temperature.

In some embodiments, the compound modulates the chemo-sensing pathway of said insect. As used herein, the term "chemo-sensing pathway" refers to a signaling pathway involved in making the insect or non-insect move away from or towards a compound present in the environment.

It is envisioned that the methods described herein are also applicable to pest control, wherein the pests are not insects but rather, e.g., nematodes, slugs or snails.

Without wishing to be bound by theory, activation of TRPA1 ion gated channel or family members in the insect leads to an increase in avoidance behavior of such insect. This increase in avoidance behavior can be used to repel insects away from a particular location and thus controlling such insects. Thus, in some embodiments, the method comprises activation of TRPA1 ion channel or family members in the insect with a compound identified by a screening method described herein.

Because compounds incorporating hydrophobic moieties will penetrate the insect cuticle, active agents can be conjugated with hydrophobic moieties. Hydrophobic moieties include, but are not limited to, lipids and sterols. These conjugated active agents can then be administered topically, such as by direct spraying on the insect or a substrate which is likely to be contacted by the insect. Alternatively, the active agents may also be administered either subcutaneously, percutaneously, or orally. When they are to be ingested, they should be applied with their carrier to the insect diet.

In one embodiment, the methods described herein are applicable to insects that are disease vectors. Vectors are organisms that can introduce a pathogen such as a bacterium or virus into a host organism to cause an infection or disease. Exemplary disease vector include, but are not limited to, mosquitoes, Ticks, Siphonaptera (fleas), Diptera (flies), Phthiraptera (lice) and Hemiptera (true bugs).

Rat fleas, especially *Xenopsylla cheopis* (the Oriental rat flea), are the principle vectors of *Pasturella pestis*, the bacterial pathogen of bubonic plague. Fleas can also transmit murine typhus caused by *Rickettsia mooseri*.

Black flies spread *Onchocerca volvulus*, a parasitic roundworm. Onchoceriasis, the disease caused by infestation of these worms, may cause blindness in peoples of Africa, Mexico, and Central and South America. Sand flies in the genus *Phlebotomus* are vectors of a bacterium (*Bartonella bacilliformis*) that causes Carrion's disease (oroyo fever) in South America. In parts of Asia and North Africa, they spread a viral agent that causes sand fly fever (pappataci fever) as well as protozoan pathogens (*Leishmania* spp.) that cause Leishmaniasis. Mosquitoes in the genus *Anopheles* are the principle vectors of malaria, a disease caused by protozoa in the genus *Trypanosoma*. *Aedes aegypti* is the main vector of the viruses that cause yellow fever and dengue. Other viruses, the causal agents of various types of encephalitis, are also carried by *Aedes* spp. mosquitoes. *Wuchereria bancrofti* and *Brugia malayi*, parasitic roundworms that cause filariasis, are usually spread by mosquitoes in the genera *Culex, Mansonia*, and *Anopheles*. Horse flies and deer flies may transmit the bacterial pathogens of tularemia (*Pasteurella tularensis*) and anthrax (*Bacillus anthraces*), as well as a parasitic roundworm (*Loa loa*) that causes loiasis in tropical Africa. Eye gnats in the genus *Hippelates* can carry the spirochaete pathogen that causes yaws (*Treponema pertenue*), and may also spread conjunctivitis (pinkeye). House flies (family Muscidae), blow flies (family Calliphoridae), and flesh flies (family Sarcophagidae) often live among filth and garbage. They can carry the pathogens for dysentary (*Shigella dysentariae*), typhoid fever (*Eberthella typhosa*), and cholera (*Vibrio comma*) on their feet and mouthparts. They have also been suspected as vectors of the viral agent that causes poliomyelitis. Tsetse flies in the genus *Glossina* transmit the protozoan pathogens that cause African sleeping sickness (*Trypanosoma gambiense* and *T. rhodesiense*).

Human lice (*Pediculus humanus* and *P. capitus*) spread *Borellia recurrentis*, a spirochaete pathogen that causes epidemic relapsing fever. They also carry the rickettsial pathogens that cause epidemic typhus (*Rickettsia prowazeki*) and trench fever (*R. quintana*).

Assassin bugs (or kissing bugs) in the genera *Triatoma* and *Rhodnius* transmit a protozoan pathogen (*Trypanosoma cruzi*) that causes Chagas disease in South and Central America. In another embodiment, the methods described herein are applicable to arachnids that are disease vectors, such as spiders or ticks. As used herein, the term insect may be extended to include other members of the phylum anthropoda that are not scientifically classified as members of the class insecta.

In one embodiment, the methods described herein are applicable to insects that are agricultural or horticultural vectors or pest. Insects, mites, and nematode vectors focus the movement of plant pathogens among immobile plants. Many insects or other arthropods may contain plant pathogens but cannot transmit these to plants and thus are not vectors. Some of our most important plant diseases require mobile vectors. Almost all plant viruses and all wall-free, plant pathogenic bacteria known as mollicutes have recognized or suspected vectors. See elsewhere for insect vector transmission of bacterial plant pathogens. Examples of some of such plant pathogen vectors are Agromyzidae, Anthomyiidae, Aphid, *Brevicoryne brassicae*, Curculionidae, *Eumetopina flavipes, Frankliniella occidentalis*, Jumping plant louse, Leaf beetle, Leafhopper, Mealybug, *Molytinae, Pissodes-Pissodes* strobe, *Pissodini*, Planthopper *Pseudococcus viburni, Scirtothrips dorsalis, Tephritidae, Thripidae, Tomicus piniperda* Treehopper, Whitefly, and *Bactrocera* and *Ceratitis* species of fruit flies In one embodiment, the methods described herein are applicable to insects that are parasites. Examples of some insect parasites are Braconid Wasps, family Braconidae; Ichneumonid Wasps, family Ichneumonidae; Chalcid Wasps, family Chalcidae; Tachinid Flies, family Tachonidae.

The active ingredient, or formulations comprising them, may be applied directly to the target insects (i.e., larvae, pupae and/or adults), or to the locus of the insects. In one embodiment, the active ingredient or a formulation containing the active ingredient is applied directly to the adult insect. In one embodiment, the active agent is applied directly to the larvae and/or pupae of the target insect. In another embodiment, the active ingredient is applied to the locus of the insects.

In another embodiment, after application of active ingredient, heat is applied to the target insects or to the locus of the insects.

In one embodiment, the active ingredient is applied as a spray. For example, the active ingredient is applied as an agricultural spray in aerial crop dusting, an environmental spray to control biting insects, or as a topical spray for localized control of biting insects. The active ingredient is formulated for the purpose for spray application such as an aerosol formulation. Spray application can be accomplished with a spray pump. The active ingredient can be also encapsulation within materials such as starch, flour and gluten in granular formulations.

In one embodiment, the active ingredient is applied topically, for example, as a lotion, a cream, or as a spray.

In one embodiment, the active ingredient is applied in conjunction with other insecticides and/or pesticides such as organo-phosphates, synthetic pyrethroids, carbamates, chlorinated hydrocarbons, when used in agricultural and/or environmental insect control.

In another embodiment, for topical application, the active ingredient is applied in conjunction with other compounds such as insect repellents and sunscreen. Insect repellents include, but are not limited to, DEET (N,N-diethyl-m-toluamide), essential oil of the lemon eucalyptus and its active ingredient p-menthane-3,8-diol (PMD), icaridin (also known as picaridin, Bayrepel, and KBR 3023), nepetalactone, also known as "catnip oil", citronella oil, permethrin, soybean oil, neem oil and Bog Myrtle, Sunscreens include, but are not limited to, oxybenzone, titanium dioxide and zinc oxide.

The active ingredient is administered in an amount effective to induce the desired response as determined by routine testing. The actual effective amount will of course vary with the specific active ingredient, the target insect and its stage of development, the application technique, the desired effect, and the duration of the effect, and may be readily determined by the practitioner skilled in the art. An effective amount of active ingredient is the amount of active ingredient to modulate activation of TRPA1, e.g., themosensing and/or chemosensing in an insect.

Formulation and Application

Methods of formulation are well known to one skilled in the art and are also found in Knowles, DA (1998) Chemistry and technology of agricultural formulations. Kluwer Academic, London, which is hereby incorporated by reference in its entirety. One skilled in the art will, of course, recognize that the formulation and mode of application may affect the activity of the active ingredient in a given application. Thus, for agricultural and/or horticultural use the TRPA1 inhibitors and/or agonists may be formulated as a granular of relatively large particle size (for example, 8/16 or 4/8 US Mesh), as water-soluble or water-dispersible granules, as powdery dusts, as wettable powders, as emulsifiable concentrates, as aqueous emulsions, as solutions, as suspension concentrate, as capsule suspensions, as soluble (liquid) concentrates, as soluble powders, or as any of other known types of agriculturally-useful formulations, depending on the desired mode of application. It is to be understood that the amounts specified in this specification are intended to be approximate only, as if the word "about" were placed in front of the amounts specified.

These formulations may be applied either as water-diluted sprays, or dusts, or granules in the areas in which insect control is desired. These formulations may contain as little as 0.1%, 0.2% or 0.5% to as much as 95% or more by weight of active ingredient, e.g. TRPA1 inhibitor.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 90 parts, 80 parts, 70 parts, 60 parts, 50 parts, 40 parts, 30 parts, 20 parts, preferably 10 parts, or less of the active ingredient, e.g. TRPA1 inhibitor or TRPA1 agonist. In one embodiment, the dust formulation comprises 1 part or less of the active ingredient and 99 parts or more of talc. As used herein, the terms "active ingredient" and "active agent" refer to a compound that modulate the activity of TRPA1 ion gated channel or family member. By the term "modulate" is meant either to inhibit TRPA1 or activate TRPA1.

Wettable powders, useful as formulations, are in the form of finely divided particles that disperse readily in water or other dispersant. The wettable powder is ultimately applied to the locus where insect control is needed either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5-80% of active ingredient, depending on the absorbency of the carrier, and usually also contain a small amount of a wetting, dispersing or emulsifying agent to facilitate dispersion. For example, a useful wettable powder formulation contains 80.0 parts of the active ingredient, 17.9 parts of Palmetto clay, and 1.0 part of sodium lignosulfonate and 0.3 part of sulfonated aliphatic polyester as wetting agents. Additional wetting agent and/or oil will frequently be added to a tank mix for to facilitate dispersion on the foliage of the plant.

Other useful formulations are emulsifiable concentrates (ECs) which are homogeneous liquid compositions dispersible in water or other dispersant, and may consist entirely of the active ingredient, and a liquid or solid emulsifying agent, or may also contain a liquid carrier, such as xylene, heavy aromatic naphthas, isophorone, or other non-volatile organic solvents. For insecticidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the insecticidal composition.

Flowable formulations are similar to ECs, except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural and/or horticultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for insecticidal applications include simple solutions of the active ingredient in a solvent in which it is completely soluble at the desired concentration, such as acetone, alkylated naphthalenes, xylene, or other organic solvents. Granular formulations, wherein the active ingredient is carried on relative coarse particles, are of particular utility for aerial distribution or for penetration of cover crop canopy. Pressurized sprays, typically aerosols wherein the active ingredient is dispersed in finely divided form as a result of vaporization of a low-boiling dispersant solvent carrier may also be used. Water-soluble or water-dispersible granules are free flowing, non-dusty, and readily water-soluble or water-miscible. In use by the farmer on the field, the granular formulations, emulsifiable concentrates, flowable concentrates, aqueous emulsions, solutions, etc., may be diluted with water to give a concentration of active ingredient in the range of say 0.1% or 0.2% to 1.5% or 2%.

By far the most frequently used are water-miscible formulations for mixing with water then applying as sprays. Water miscible, older formulations include: emulsifiable concentrate, wettable powder, soluble (liquid) concentrate, and soluble powder. Newer, non-powdery formulations with reduced or no hazardous solvents and improved stability include: suspension concentrate, capsule suspensions, water dispersible granules. Such formulations are preferably solutions and suspension, e. g., aqueous suspension and solutions, ethanolic suspension and solutions, aqueous/ethanolic suspension and solutions, saline solutions, and colloidal suspensions.

Alternatively, a sprayable wax emulsion formulation can be used. The formulation contains the active ingredient, in an amount from about 0.01% to 75% by weight. The aqueous wax emulsions are broadly described in U.S. Pat. No. 6,001,346, which is hereby incorporated by reference in is entirety. The TRPA1 inhibitors of the methods described herein can have a viscosity appropriate for use in aerial or backpack spray applications.

The biodegradable wax carrier comprises at least about 10% by weight of the formulation. The biodegradable wax carrier is selected from the group consisting of paraffin, beeswax, vegetable based waxes such as soywax (soybean based), and hydrocarbon based waxes such as Gulf Wax Household Paraffin Wax; paraffin wax, avg. m.p. 53C (hexacosane), high molecular weight hydrocarbons). carnauba wax, lanolin, shellac wax, bayberry wax, sugar cane wax, microcrystalline, ozocerite, ceresin, montan, candelilla wax, and combinations thereof.

Formulations can contain an emulsifier in an amount from about 1% to about 10% by weight. Suitable emulsifiers include lecithin and modified lecithins, mono- and diglycerides, sorbitan monopalmitate, sorbitan monooleate, sorbitan monolaurate, polyoxyethylene-sorbitan monooleate, fatty acids, lipids, etc. The emulsifiers provide or improve emulsification properties of the composition. The emulsifier can be selected from many products which are well known in the art, including, but not limited to, sorbitan monolaurate (anhydrosorbitol stearate, molecular formula $C_{24}H_{46}O_6$), ARLACEL 60, ARMOTAN MS, CRILL 3, CRILL K3, DREWSORB 60, DURTAN 60, EMSORB 2505, GLYCOMUL S, HODAG SMS, IONET S 60, LIPOSORB S, LIPOSORB S-20, MONTANE 60, MS 33, MS33F, NEWCOL 60, NIKKOL SS 30, NISSAN NONION SP 60, NONION SP 60, NONION SP 60R, RIKEMAL S 250, sorbitan c, sorbitan stearate, SORBON 60, SORGEN 50, SPAN 55, AND SPAN 60; other sorbitan fatty acid ester that may be used include sorbitan monopalmitate, sorbitan monostearate, sorbitan tristearate, sorbitan monooleate, sorbitan sesquioleate, sorbitan trioleate, sorbitan monooleate, sorbitan trioleate. In certain embodiments, SPAN 60 is preferred.

In certain embodiments, formulations can includes a phagostimulant, such as corn oil, molasses, glycerol, or corn syrup, proteinaceous material (protein or hydrolyzed protein), sugars like sucrose, or food-based ingredients such as trimethylamine, putrescine, bacterial or yeast volatiles or metabolites, ammonium acetate, ammonium carbonate or other ammonia-emitting compounds. Acetic acid vapor can be provided by compounds that produce volatilized acetic acid, for example, aqueous acetic acid, glacial acetic acid, glacial (concentrated) acetic acid, or ammonium producing compounds such as but not restricted to ammonium hydroxide, ammonium carbonate, ammonium bicarbonate, ammonium acetate, etc. Ammonium acetate is most preferred for providing acetic acid and ammonia vapors.

The active ingredient, may be formulated and/or applied with one or more second compounds. Various combinations TRPA1 inhibitors and TRPA1 agonists can be used to obtain greater advantage. For example both a TRPA1 inhibitor and TRPA1 agonist are applied at the same time. In one embodiment, a formulation described herein comprises both a TRPA1 inhibitor and a TRPA1 agonist. In one embodiment, two or more active agents are formulated together. In one embodiment, two or more active agents formulated together are all either TRPA1 inhibitors or are all TRPA1 agonists. Such combinations may provide certain advantages, such as, without limitation, exhibiting synergistic effects for greater control of insects or non-insect pests, reducing rates of application thereby minimizing any impact to the environment and to worker safety, controlling a broader spectrum of insects and non-insect pests, and improving tolerance by non-pest species, such as mammals and fish. Other second compounds include, without limitation, insecticides, pesticides, plant growth regulators, fertilizers, soil conditioners, or other agricultural and horticultural chemicals. The formulation may include such second compounds in an amount from about 0.002% to about 25% by weight of the composition.

Insecticides include, but are not limited to, organophosphate insecticides, such as chlorpyrifos, diazinon, dimethoate, malathion, parathion-methyl, naled, and terbufos; nicotinic insecticides such as imidacloprid and thiacloprid; pyrethroid insecticides, such as fenvalerate, delta-methrin, fenpropathrin, cyfluthrin, flucythrinate, alpha-cypermethrin, biphenthrin, resolved cyhalothrin, etofenprox, esfenvalerate, tralomethrin, tefluthrin, cycloprothrin, betacyfluthrin, and acrinathrin; carbamate insecticides, such as aldecarb, carbaryl, carbofuran, and methomyl; organochlorine insecticides, such as endosulfan, endrin, heptachlor, and lindane; benzoylurea insecticides, such as diflubenuron, triflumuron, teflubenzuron, chlorfluazuron, flucycloxuron, hexaflumuron, flufenoxuron, dimlin, novaluron, and lufenuron; diacylhydrazines such as methoxyfenozide; phenylpyrazoles such as fipronil or ethiprole, chlorfenapyr, diafenthiuron, indoxacarb, metaflumazone, emamectin benzoate, abamectin, pyridalyl, flubendiamide, rynaxypyr; and other insecticides, such as amitraz, clofentezine, fenpyroximate, hexythiazox, spinosad, and imidacloprid.

Pesiticide include, but are not limited to, benzimidazine fungicides, such as benomyl, carbendazim, thia-bendazine, and thiophanate-methyl; 1,2,4-triazine fungicides, such as epoxyconazole, cyproconazole, flusilazine, flutriafol, propiconazine, tebuconazine, triadimefon, and tri-adimenol; substituted anilide fungicides, such as metalaxyl, oxadixyl, procymidone, and vinclozolin; organophosphorus fungicides, such as fosetyl, iprobenfos, pyrazophos, edifen-phos, and tolclofos-methyl; morpholine fungicides, such as fenpropimorph, tridemorph, and dodemorph; other systemic fungicides, such as fenarimol, imazalil, prochloraz, tricyclazine, and triforine; dithiocarbamate fungicides, such as mancozeb, maneb, propineb, zineb, and ziram; non-systemic fungicides, such as chlorothalonil, dichlorofluanid, dithianon, and iprodione, captan, dinocap, dodine, fluazinam, gluazatine, PCNB, pencycuron, quintozene, tricylamide, and validamycin; inorganic fungicides, such as copper and sulphur products, and other fungicides; nematicides such as carbofuran, carbosulfan, turbufos, aldecarb, ethoprop, fenamphos, oxamyl, isazofos, cadusafos, and other nematicides.

Formulations can contain visual attractants, e.g. food coloring.

A variety of additives may be incorporated into the formulation. These additives typically change and/or enhance the physical characteristics of the carrier material and are, therefore, suitable for designing compositions having specific requirements as to the release rate and amount of the active ingredient, protection of the wax composition from weather conditions, etc. These additives are, among others, plasticizers, volatility suppressants, antioxidants, lipids, various ultraviolet blockers and absorbers, or antimicrobials, typically added in amounts from about 0.001% to about 10%, more typically between 1-6%, by weight.

Plasticizers, such as glycerin or soy oil affect physical properties of the composition and may extend its resistance to environmental destruction.

Antioxidants, such as vitamin E, BHA (butylated hydroxyanisole), BHT (butylated hydroxytoluene), and other antioxidants which protect the bioactive agent from degradation, may be added in amounts from about 0.1% to about 3%, by weight.

Ultraviolet blockers, such as beta-carotene, lignin or p-aminobenzoic acid protect the bioactive agents from light degradation may be added in amounts from about 1% to about 3%, by weight.

Antimicrobials, such as potassium sorbate, nitrates, nitrites, and propylene oxide, protect the bioactive agents from microbial destruction may be added in amounts from 0.1% to about 2% by weight.

Adjuvants can also be added to the formulation. An adjuvant is broadly defined as any substance added to the spray tank, separate from the pesticide formulation, that will improve the performance of the pesticide. These includes but are not limited to wetter-spreaders, stickers, penetrants, compatibility agents, buffers, and so on.

Other compounds and materials can be added provided they do not substantially interfere with the activity of active ingredient. Whether or not an additive substantially interferes with the active ingredient's activity can be determined by standard test formats, involving direct comparisons of efficacy of the composition of the active ingredient without an added compound and the composition of the active ingredient with an added compound.

In one embodiment, the active ingredient is preferably applied topically on a subject at risk of insect bites. The active ingredient is applied in therapeutically effective amount in admixture with pharmaceutical carriers, in the form of topical pharmaceutical compositions. Such compositions include solutions, suspensions, lotions, gels, creams, ointments, emulsions, sprays, etc. All of these dosage forms, along with methods for their preparation, are well known in the pharmaceutical and cosmetic art and described, for example in, Harry's Cosmeticology (Chemical Publishing, 8th ed. 2000) and Remington's Pharmaceutical Sciences (Mack Publishing Co., 18th ed. 1990), contents of both of which are incorporated herein by reference in their entirety. Typically, such topical formulations contain the active ingredient in a concentration range of 0.001 to 10 mg/ml, in admixture with suitable vehicles. Other desirable ingredients that can be added to the topical preparations include preservatives, co-solvents, viscosity building agents, carriers, etc.

Penetration enhancers may, for example, be surface active agents; certain organic solvents, such as di-methylsulfoxide and other sulfoxides, dimethyl-acetamide and pyrrolidone; certain amides of heterocyclic amines, glycols (e.g. propylene glycol); propylene carbonate; oleic acid; alkyl amines and derivatives; various cationic, anionic, nonionic, and amphoteric surface active agents; and the like.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols.

Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences (Mack Publishing Co., 18$^{th}$ ed., 1990), content of which is incorporated herein by reference in its entirety. The pH and exact concentration of the various components of the pharmaceutical composition are adjusted according to routine skills in the art. See Goodman and Gilman's The Pharmacological Basis for Therapeutics (McGraw-Hill Professional, 10$^{th}$ ed., 2001), content of which is incorporated herein by reference in its entirety.

Excipients include those described, for example, in Handbook of Pharmaceutical Excipients (Pharmaceutical Press, 6$^{th}$ ed., 1990), content of which is incorporated herein by reference in its entirety.

Inventors have discovered that an insect will stop eating after ingesting a TRPA1 activating compound. For example ingesting a TRPA1 ion gated channel agonist can cause an insect to stop eating. Thus, in one embodiment, the compounds are formulated with a food source for insects, e.g., formulated with compounds in insect diet. In another embodiment, the compounds are formulated with sucrose. Without wishing to be bound by theory, the insect will feed on such mixtures and stop eating.

In some embodiments, the compound can be applied to breeding locus of insects. Without wishing to be bound by theory, application of active agent to breeding locus inhibits insects from breeding by either repelling them from that locus or preventing laying of eggs at that locus, or both.

In another embodiment, the active agent is applied to feeding locus of insects. This inhibits insect feeding leading to starvation of insects.

In yet another embodiment, the active agent is applied to both breeding and feeding locus of insects.

In one embodiment, the active agent is applied as a spray to locus of insects, e.g., breeding locus, feeding locus.

In one embodiment, the active agent is applied to insect traps. For example, the trap may be coated with the active agent or trap may be loaded with insect food comprising an active agent.

In one embodiment, the active agent is applied to clothing, such as a shirt, hat, pants, shorts, outer garment, etc. . . . of a subject. In one embodiment, the active agent is applied to clothing by soaking the clothing in a solution comprising the active agent. In another embodiment, the active agent is applied to clothing by spraying the clothing with a formulation comprising the active agent.

Definitions

Unless otherwise explained, all technical and scientific terms used herein have the same meaning as commonly understood by one of ordinary skill in the art to which this disclosure belongs. Definitions of common terms in neurobiology and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); The ELISA guidebook (Methods in molecular biology 149) by Crowther J. R. (2000); Fundamentals of RIA and Other Ligand Assays by Jeffrey Travis, 1979, Scientific Newsletters; Immunology by Werner Luttmann, published by Elsevier, 2006. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Unless otherwise stated, experiments detailed herein were performed using standard procedures, as described, for example in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987)).

Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol 57, Jennie P. Mather and David Barnes editors, Academic Press, 1st edition, 1998) which are all incorporated by reference herein in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural referents unless context clearly indicates otherwise. Similarly, the word "or" is intended to include "and" unless the context clearly indicates otherwise.

As used herein the term "comprising" or "comprises" is used in reference to compositions, methods, and respective component(s) thereof, that are essential to the invention, yet open to the inclusion of unspecified elements, whether essential or not. The term "comprises" means "includes." The abbreviation, "e.g." is derived from the Latin exempli gratia, and is used herein to indicate a non-limiting example. Thus, the abbreviation "e.g." is synonymous with the term "for example."

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Although methods and materials similar or equivalent to those described herein can be used in the practice or testing of this disclosure, suitable methods and materials are described below.

The terms "decrease", "reduced", "reduction", "decreased" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) change from a reference level. The term refers to statistical evidence that there is a difference. It is defined as the probability of making a decision to reject the null hypothesis when the null hypothesis is actually true. The decision is often made using the p-value.

As used herein, the term "peptide" is used in its broadest sense to refer to compounds containing amino acids, amino acid equivalents or other non-amino groups, while still retaining the desired functional activity of a peptide. Peptide equivalents can differ from conventional peptides by the replacement of one or more amino acids with related organic acids (such as PABA), amino acids or the like or the substitution or modification of side chains or functional groups. The peptides can be linear or cyclic. A peptide can be modified to include one or more of D-amino acids, beta-amino acids, chemically modified amino acids, naturally occurring non-proteogenic amino acids, rare amino acids, and chemically synthesized compounds that have properties known in the art to be characteristic of an amino acid. As used herein, the term "proteogenic" indicates that the amino acid can be incorporated into a protein in a cell through well-known metabolic pathways.

As used herein, the term "nucleic acid" or "oligonucleotide" or grammatical equivalents herein means at least two nucleotides, including analogs or derivatives thereof, that are covalently linked together. The nucleic acids can be single stranded or double stranded. The nucleic acid can be DNA, RNA or a hybrid, where the nucleic acid contains any combination of deoxyribo- and ribo-nucleotides, and any combination of uracil, adenine, thymine, cytosine and guanine. The nucleic acids can comprise one or more backbone modifications, e.g., phosphoramide (Beaucage et al., Tetrahedron 49(10):1925 (1993) and references therein; Letsinger, J. Org. Chem. 35:3800 (1970)), phosphorothioate, phosphorodithioate, O-methylphophoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); Nielsen, Nature, 365:566 (1993)). The nucleic acids can also include modifications to nucleobase and/or sugar moieties of nucleotides. Exemplary sugar modifications at the sugar moiety include replacement of 2'-OH with halogens (e.g., fluoro), O-methyl, O-methoxyethyl, $NH_2$, SH and S-methyl.

As used herein, the term "polysaccharide" refers to macromolecular carbohydrates whose molecule consists of a large number of monosaccharide molecules which are joined to one another by glycosidic linkage. Polysaccharides are classified by dividing them into. The term polysaccharide is also intended to embrace an oligosaccharide. The polysaccharide can be homopolysaccharides or heteropolysaccharides. Whereas the homopolysaccharides contain only one kind of unit, the heteropolysaccharides consist of monomer units of different kinds.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "analog" as used herein refers to a compound that results from substitution, replacement or deletion of various organic groups or hydrogen atoms from a parent compound. As such, some monoterpenoids can be considered to be analogs of monoterpenes, or in some cases, analogs of other monoterpenoids, including derivatives of monoterpenes. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.*: 39(1-3):63-80 (1999); Waller et al., "Prodrugs", *Br. J. Clin. Pharmac.* 28: 497-507 (1989), content of all of which is herein incorporated by reference in its entirety.

The term "pharmaceutically acceptable salt" is a salt of a compound of the invention that retains the biological effectiveness and properties of the compound of the invention and which is not biologically or otherwise undesirable. Salts may be derived from inorganic or organic acids and bases, and include pharmaceutically acceptable anions, the anions of acid addition salts, and pharmaceutically acceptable cations, the cations of base addition salts. Acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. Base addition salts may be derived from inorganic bases such as sodium hydroxide, potassium hydroxide, lithium hydroxide, ammonium, calcium hydroxide, magnesium hydroxide, and the like. Salts derived from organic bases include those formed from primary, secondary, and tertiary amines, substituted amines including naturally occurring substituted amines, including isopropylamine, trimethylamine, diethylamine, triethylamine, tripropylamine, ethanolamine, 2-dimethylaminoethanol, cyclohexylamine, pyridine, ethylenediamine, tromethamine, lysine, arginine, histidine, caffeine, procaine hydrabamine choline, betaine, glucosamine, N-alkylglucamines, theobromine, purines, piperazine, piperidine, N-ethylpiperidine, and the like.

As used herein, the term "EC50," refers to the concentration of a compound that produces 50% of maximal activation of a TRPA1 activity measurable using the same assay in the absence of the compound. Stated differently, the "EC50" is the concentration of a compound that gives 50% activation, when 100% activation is set at the amount of activity that does not increase with the addition of more of the compound. The EC50 can be as measured in vitro or in vivo.

As used herein, the term "IC50" refers to the concentration of a compound that produces 50% of the maximal inhibition of an TRPA1 activity measurable using the same assay in the absence of said compound. The IC50 can be as measured in vitro or in vivo.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The present invention may be defined in any of the following numbered paragraphs:

1. A method of identifying an insect-specific TRPA1 modulator comprising:
   (a) contacting a test compound with an insect TRPA1 and a mammalian TRPA1; and
   (b) assaying modulation of insect and mammalian TRPA1 activity.
2. The method of claim 1, further comprising the step of selecting the test compound that modulates the activity of insect TRPA1 by at least 10% relative to the mammalian TRPA1.
3. The method of any of claims 1-2, wherein the compound inhibits the activity of the insect TRPA1.
4. The method of any of claim 1-2, wherein the compound activates the insect TRPA1.
5. The method of any of claims 1-4, wherein the insect TRPA1 is selected from the group consisting of *D. melanogaster* TRPA1 isoform F (Accession No. ABW08500.3), *D. melanogaster* TRPA1 isoform E (Accession No. AAF50356.4), *D. melanogaster* TRPA1 isoform F (Accession No. NP_001097554.3), *D. melanogaster* TRPA1 isoform E (Accession No. NP_648263.4), *D. melanogaster* TRPA1 (Accession No. Q7Z020.3), *Anopheles gambiae* TRPA1 (Accession No. ACC86138.1), *Tribolium castaneum* hypothetical protein TcasGA2 TC002449 (Accession No. EFA01253.1), and conservative variants thereof.
6. The method of any of claims 1-5, wherein mammalian TRPA1 is selected from the group consisting of *Rattus norvegicus* transient receptor potential cation channel, subfamily A, member 1 (Accession No. NP_997491.1); *Rattus norvegicus* transient receptor potential cation channel subfamily A member 1 (Accession No. AAS78661.1); *Mus musculus* transient receptor potential cation channel, subfamily A, member 1 (Accession No. NP_808449.1); *Homo sapiens* transient receptor potential cation channel subfamily A member 1 (Accession No. NP_015628.2); *Mus musculus* transient receptor potential cation channel, subfamily A, member 1 (Accession No. AAI31964.1); *Mus musculus* transient receptor potential cation channel, subfamily A, member 1 (Accession No. AAI20564.1); *Mus musculus* transient receptor potential cation channel, subfamily A, member 1, isoform CRA_b (Accession No. EDL14332.1); *Mus musculus* transient receptor potential cation channel, subfamily A, member 1, isoform CRA_a (Accession No. EDL14331.1); *Bos Taurus* transformation sensitive protein p120 (Accession No. XP_581588.2); *Pan troglodytes* predicted ankyrin-like protein 1 (Accession No. XP_519806.2); *Macaca mulatta* predicted ankyrin-like protein 1 (Accession No. XP_001083172.1); *Gallaus gallus* predicted similar to transient receptor potential cation channel subfamily A member 1 (Accession No. XP_418294.2); *Danio rerio* TRPA1 (Accession No. AAV37177.1) *Danio rerio* transient receptor potential cation channel, subfamily A, member 1a (Accession No. NP_001007066.1), and conservative variants thereof.
7. The method of any of claims 1-6, wherein the test compound is selected from the group consisting of small organic molecule, small inorganic molecule, polysaccharides, peptides, proteins, nucleic acids, an extract made from biological materials such as bacteria, plants, fungi, animal cells, animal tissues, and any combinations thereof.
8. The method of any of claims 1-7, wherein the test compound is synthetic compound.
9. The method of any of claims 1-8, wherein the test compound is unpurified.
10. The method of any of claims 1-9, wherein the test compound has a molecular weight of less than 5000 Daltons (5 kD).
11. The method of any of claims 1-10, wherein the test compound is tested at a concentration in the range of about 0.1 nM to about 1000 mM.
12. The method of any of claims 1-11, wherein the insect TRPA1 is inside a cell.
13. The method of any of claims 1-12, wherein the mammalian TRPA1 is inside a cell.
14. The method of claim 12 or 13, wherein the cell is an oocyte.
15. The method of claim 14, wherein oocyte is an *Xenopus lavis* oocyte.
16. A compound selected by the method of any of claims 1-10.
17. A method of insect control comprising applying to an insect a compound selected by the method of any of claims 1-15.
18. The method of claim 17, wherein the compound is an inhibitor of TRPA1.
19. The method of claim 18, wherein the compound has an IC50 value of less than 500 nM.
20. The method of claim 17, wherein the compound is an activator of TRPA1.
21. The method of claim 19, wherein the compound has and EC50 value of less than 500 nM.
22. The method of any of claims 17-21, wherein the insect is selected from the group consisting of fleas, rat fleas, oriental rat fleas, flies, black flies, sand flies, mosquitoes, horse flies, deer flies, eye gnats, house flies, blow flies, flesh flies, tsetse flies, lice, human lice, true bugs, assassin bugs, kissing bugs, and any combinations thereof.
23. The method of any of claims 17-22, wherein the insect is a disease vector.
24. The method of any of claims 17-23, wherein the insect is an agricultural/horticultural pest.
25. The method of any of claim 17-24, wherein the insect is a parasite.
26. The method of any of claim 17-24, wherein compound is applied as a spray.
27. The method of any of claim 17-24, wherein compound is applied topically.
28. The method of any of claim 17-24, wherein compound is applied directly to adult insects.
29. The method of any of claim 17-24, wherein compound is applied to a locus of insects.
30. The method of claim 29, wherein said locus is a breeding locus.
31. The method of claim 29, wherein said locus is a feeding locus.
32. The method of any of claims 17-31, wherein the compound is formulated with a food source.
33. The method of any of claims 17-32, wherein the compound is formulated with sucrose.

34. The method of any of claims 17-33, wherein the compound modulates thermo- and/or chemo-sensing in the insect.

EXAMPLES

Methods

Proboscis Extension Behavior.

The proboscis extension assay was modified from ones previously described in Thorne, et al., *Curr Biol* 14, 1065-1079 (2004) and Wang, et al., Scott, *Cell* 117, 981-991 (2004) and as detailed in herein.

Physiology.

Oocyte and larval physiology were performed largely as described in Hamada, et al., *Nature* 454, 217-220 (2008) and Pulver, et al., *J Neurophysiol* 101, 3075-3088 (2009), with additional details provided in below. Chemical sensitivities of wild type and mutant (dTRPA1-2C) channels were assessed by normalizing all currents to currents observed at 1 mM AITC. Chemically unrelated insect repellents like DEET, IR-3535, and deltamethrin failed to activate dTRPA1 (data not shown).

Phylogeny.

TRPA sequences were assembled from available genomic and EST data. Multiple sequence alignment was performed using ProbCons (Do, C. B., M. S. Mahabhashyam, M. Brudno, and S. Batzoglou, *Genome Res* 15, 330-340 (2005)) for region from ~310 amino acids N-terminal of transmembrane regions (containing the residues implicated in chemical sensing) to ~50 amino acids C-terminal of transmembrane regions (Data not shown). Bayesian analysis was calculated with the parallel version of MrBayes 3.1.2 using mixed substitution rate matrices and gamma distributed rate variation across sites (8 categories). An exponential prior (mean=1.0) was assumed for shape parameter of the gamma distribution, an unconstrained exponential prior (mean=1.0) assumed for branch lengths, and a uniform prior assumed for all labeled topologies. Two independent MCMC analyses were performed (each with one cold and three heated chains), with other parameters set to defaults. Chains were run for 10,000,000 generations, and convergence inferred after cold chain topologies reached a standard deviation of split frequencies of less than 0.005 (~250,000 generations). After convergence, the first half of the chain was discarded as "burnin". Maximum likelihood analysis was performed with PhyML 3.0, using LG substitution rate matrix, gamma distributed rate variation (8 categories) and was bootstrapped 1000 times. A BioNJ distance-based phylogenetic analysis was performed with PAUP 4b10 (Swofford, D. L., *Phylogenetic Analysis Using Parsimony (\*and Other Methods), Version* 4 (Sinauer Associates, Sunderland, Mass., 2003)) and bootstrapped 1000 times. Ancestral sequence reconstruction was performed with PAML 4.2b (Yang, Z., *Mol Biol Evol* 24, 1586-1591 (2007)) using the consensus Bayesian phylogenetic tree and mean alpha rate parameter. Branch lengths were fixed.

Fly Strains and Immunohistochemistry.

dTrpA1$^{SH}$-Gal4, UAS-dTRPA1, and UAS-dTRPA1$^{dsRNA}$ transgenic strains (Hamada, et al., *Nature* 454, 217-220 (2008), as well as Dll-Gal4 (Calleja, et al., *Science* 274, 252-255 (1996)), MJ94-Gal4 (Gendre, et al., *Development* 131, 83-92 (2004) and Joiner et al., *J Neurosci* 17, 9384-9391 (1997)), Gr66a-Gal4 (Dunipace, et al., *Curr Biol* 11, 822-835 (2001)), UAS-Painless$^{AR9}$ (Al-Anzi, B., W. D. Tracey, Jr., and S. Benzer, *Curr Biol* 16, 1034-1040 (2006)), and painless (Tracey, et al., *Cell* 113, 261-273 (2003)) mutants have been previously described. UAS-nls:GFP and UAS-mCD8: GFP fly strains were obtained from Bloomington. Anti-dTRPA1 immunohistochemistry was performed as described in (Rosenzweig, et al., *Genes Dev* 19, 419-424 (2005)). Details of the creation of dTrpA1$^{fs}$ and dTrpA1$^{ins}$ were previously reported and described in Rosenzweig, M., K. Kang, and P. A. Garrity, *Proc Natl Acad Sci USA* 105, 14668-14673 (2008) and Hamada, et al., *Nature* 454, 217-220 (2008)). Briefly, dTrpA1$^{fs}$ has a 2-bp insertion creating frameshift mutation within the third ankyrin repeat of dTRPA1, prior to the transmembrane regions. dTrpA1$^{ins}$ contains two mutated copies of dTrpA1 that flank vector targeting sequences: one copy lacks the ion pore and sixth transmembrane domain, while the other copy lacks the promoter and upstream sequences, all of exon 1, part of exon 2, and contains the 2 bp insertion mutation present in dTrpA1$^{fs}$.

PER Behavioral Assays,

Two to seven day old flies were starved overnight on wet Kim wipes, anaesthetized on ice, and affixed to a glass slide. Flies recovered in a humidified chamber for at least 2 hrs at room temperature prior to testing. During the PER assay, the fly was first satiated with water, then a solution containing tastants was touched to the forelegs as a liquid ball on a pipette tip. If the proboscis was extended and contact with the food was maintained for 2-3 sec, the response was scored as 1. If the proboscis stuttered on the tastant, or contact was brief, a 0.5 was awarded. If the proboscis failed to contact the solution within 5 sec of offering, a 0 was awarded. Each fly was offered tastants five times per experiment, and between offerings water was given to satiation. Because AITC, cinnamaldehyde and NMM were usually accepted on first offering, PER frequency was calculated for the second through fifth offerings (sum of four scores per fly divided by 4). Responses to sucrose resumed within ~10 minutes after pungent chemical exposure, indicating that feeding was not permanently impaired (K.K. and P.G., unpublished). For leg only PER assays, the procedures were as above except flies were not allowed to contact the food with their proboscis. The inventors found that NMM had no effect on ingestion when using a previously published ingestion-independent PER assay for chemical sensitivity (Al-Anzi, B., W. D. Tracey, Jr., and S. Benzer, *Curr Biol* 16, 1034-1040 (2006)), suggesting the inhibitory effects of AITC in that assay were not gustatory.

Two-Electrode Voltage Clamping on *Xenopus laevis* Oocytes.

Agonist-evoked dTRPA1 currents were recorded as previously described in (Hamada, et al., *Nature* 454, 217-220 (2008)), with the following modifications. Agonists of interest were added to the oocyte perfusion buffer (96 mM NaCl, 1 mM MgCl2, 4 mM KCl, and 5 mM HEPES, pH 7.6). Voltage was initially held at −60 mV, and a 300-ms voltage ramp (−60 mV to 60 mV) per sec was applied to dTRPA1- or AgTRPA1-expressing oocytes during perfusion of agonist-containing buffer. Typical oocyte resting membrane potentials were between −25 and −60 mV. Agonist-elicited currents were specific and TRPA1-dependent; they were absent from uninjected or water-injected oocytes and were significantly reduced by mutation of two cysteine residues within dTRPA1 (FIGS. 3A-3E and 4A, and data not shown). Furthermore, they were inhibited by ruthenium red, which partially inhibits warmth-activated dTRPA1 and agTRPA1 currents, and they exhibited the reversal potential and rectification properties previously associated with warmth-activated dTRPA1 and agTRPA1 currents (Hamada, et al., *Nature* 454, 217-220 (2008)). EC50s for wild type dTRPA1 channels were obtained at −60 mV, with AITC provided for 60 sec with 30 sec intervals between increasing concentrations. The low sensitivity of dTRPA1-2C to AITC precluded EC50 analysis of the mutant channel.

Larval Neuromuscular Junction Electrophysiology.

TRPA channels were expressed in larval motor neurons using OK371-GAL4, a driver specific for glutamatergic neurons, as described in Pulver, et al., *J Neurophysiol* 101, 3075-3088 (2009)). In all preparations, the ventral ganglion was dissected away, leaving only motor axons and terminals. Larval muscle 6 (m6) was impaled with a sharp electrode (10-20 MΩ □□containing 3M KCl. Resting membrane potentials were typically between −40 and −50 mV. Saline was perfused over the preparation, then increasing concentrations of cinnamaldehyde applied using a custom built gravity perfusion system. EJP frequency was measured ~30 sec after application of each concentration using analysis scripts in Spike 2 (Cambridge Electronic Design, Cambridge, UK). Painless was overexpressed using the functional rescue construct UAS-Painless$^{AR9}$ (Al-Anzi, B., W. D. Tracey, Jr., and S. Benzer, *Curr Biol* 16, 1034-1040 (2006)).

Molecular Biology.

Substitutions of cysteine/lysine residues in dTrpA1 were made by swapping a region of wild type cDNA sequence including codons of cysteine or lysine with mutated cassettes. A pair of mutually complementary oligonucleotide primers with a desired mutation were prepared, and each of them was paired with upstream or downstream primers for the first two PCR reactions. The resulting two PCR fragments overlap in the mutant primer-annealing region that contains the replaced codons, and served as template for the second PCR reaction amplified only with the upstream and down stream primers. The upstream and down stream primers were designed to be just outside of specific restriction endonuclease target sites that were used to clone the second PCR products back in the wild type dTrpA1 cDNA background sequence. The fragments amplified by PCR were confirmed by sequencing after cloning to make sure that only desired mutations were introduced in the final cDNA constructs.

Sequence Alignment and Phylogeny.

Figure 4A:
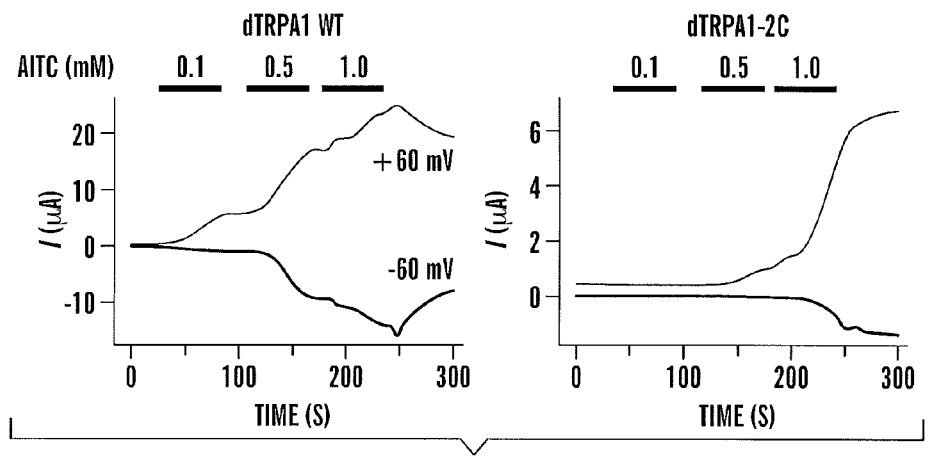
FIG. 4A shows response of TRPA1-wt (wild type) and dTRPA1-2C channels in *Xenopus* oocytes. 60 sec pulses of AITC (0.1, 0.5, and 1.0 mM) were applied with 25 sec intervals.

Multiple sequence alignments were visualized using JAL2.4 (Waterhouse, et al., *Bioinformatics* 25, 1189-1191 (2009)). Conservation reflects conservation of physicochemical properties of residues was calculated as described in (Livingstone, C. D. and G. J. Barton, *CABIOS* 9, 745-756 (1993)). Quality is inversely proportional to the cost of mutations in a residue, measure of likelihood of observing mutations (Waterhouse, et al., *Bioinformatics* 25, 1189-1191 (2009)). Consensus reflects percentage of modal residue. FIGS. 4A and 13 provide alternative alignments for Painless in C450 and C650 regions; neither indicates cysteine conservation. The LG substitution matrix was as described in Le, S. Q. and O. Gascuel, *Mol Biol Evol* 25, 1307-1320 (2008). The input data for the ancestral reconstruction was the consensus Bayesian phylogenetic tree depicted in FIG. 4D. The inventors used the "marginal reconstruction" method (RateAncestor=1) in PAML4 (Nakagawa, T. and L. B. Vosshall, *Curr Opin Neurobiol* 19, 284-292 (2009)), which determines the posterior probability of each amino acid at each site in the protein alignment for a given node. The alpha parameter (for gamma distributed rate variation across sites) was fixed to the Bayesian expected value as determined by MrBayes.

Results and Discussion

Chemical nociception, the detection of tissue-damaging chemicals, is important for animal survival and causes human pain and inflammation, but its evolutionary origins are largely unknown. Reactive electrophiles are a class of noxious compounds humans find pungent and irritating, like allyl isothiocyanate (in wasabi) and acrolein (in cigarette smoke). See for example, Basbaum, et al., *Cell* 139, 267-284 (2009); Bessac, B. F. and S. E. Jordt, *Physiology (Bethesda)* 23, 360-370 (2008); and Eisner, T., in *Chemical Ecology*, edited by E. Sondheimer and J. B. Simeone (New York, 1970), Vol. Academic Press. Insects to humans find reactive electrophiles aversive (Basbaum, et al., *Cell* 139, 267-284 (2009); Bessac, B. F. and S. E. Jordt, *Physiology (Bethesda)* 23, 360-370 (2008); and Eisner, T., in *Chemical Ecology*, edited by E. Sondheimer and J. B. Simeone (New York, 1970), Vol. Academic Press), but whether this reflects conservation of an ancient sensory modality has been unclear. Here the inventors have identify the molecular basis of reactive electrophile detection in flies. The inventors demonstrate that dTRPA1, the *Drosophila melanogaster* ortholog of the human irritant sensor, acts in gustatory chemosensors to inhibit reactive electrophile ingestion. The inventors further demonstrate that fly and mosquito TRPA1 orthologs are molecular sensors of electrophiles, using a mechanism conserved with vertebrate TRPA1s. Phylogenetic analyses indicate invertebrate and vertebrate TRPA1s share a common ancestor that possessed critical characteristics required for electrophile detection. These findings support emergence of TRPA1-based electrophile detection in a common bilaterian ancestor, with widespread conservation throughout vertebrate and invertebrate evolution. Such conservation contrasts with the evolutionary divergence of canonical olfactory and gustatory receptors and can relate to electrophile toxicity.

Figure 1B:
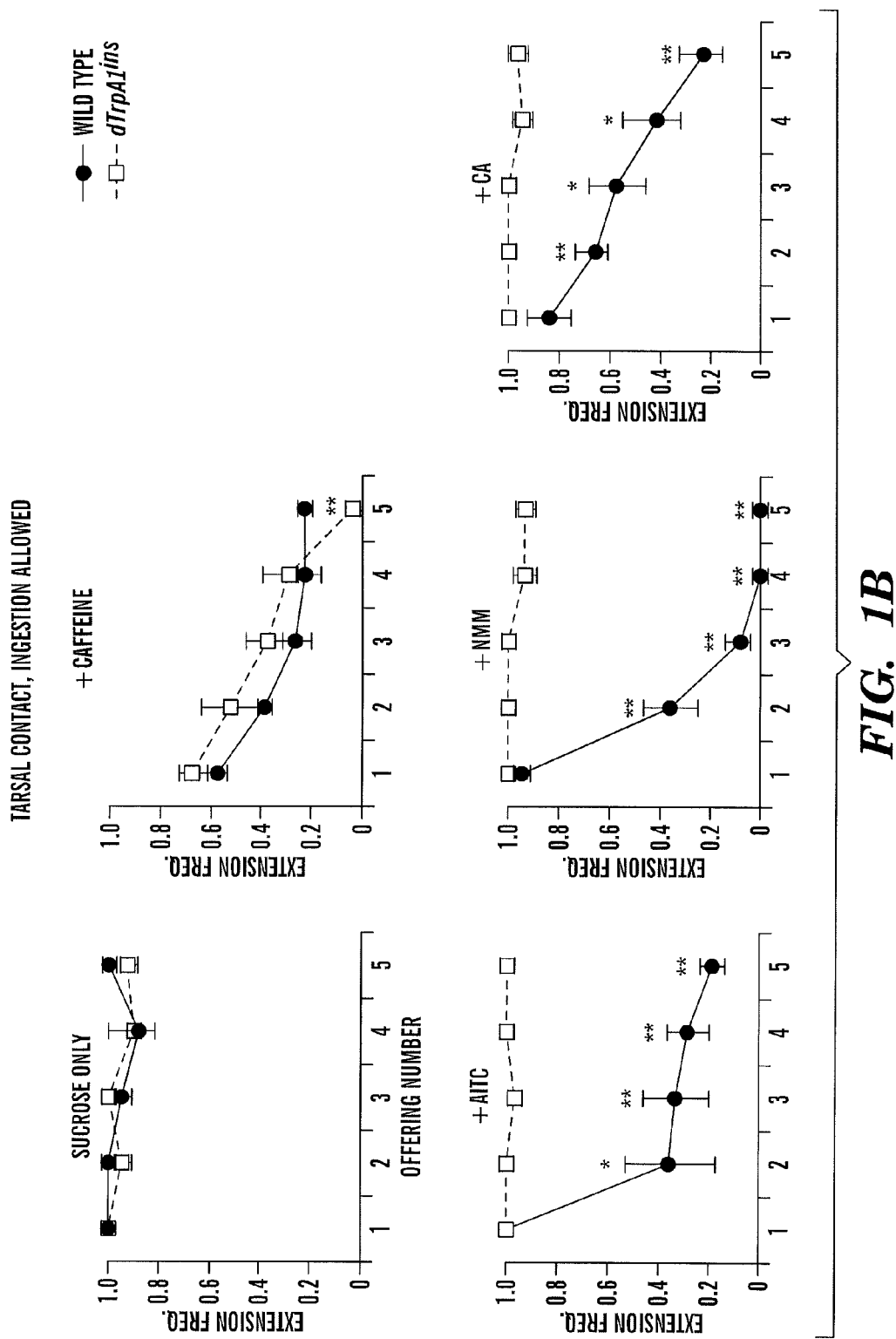
Figure 1C:
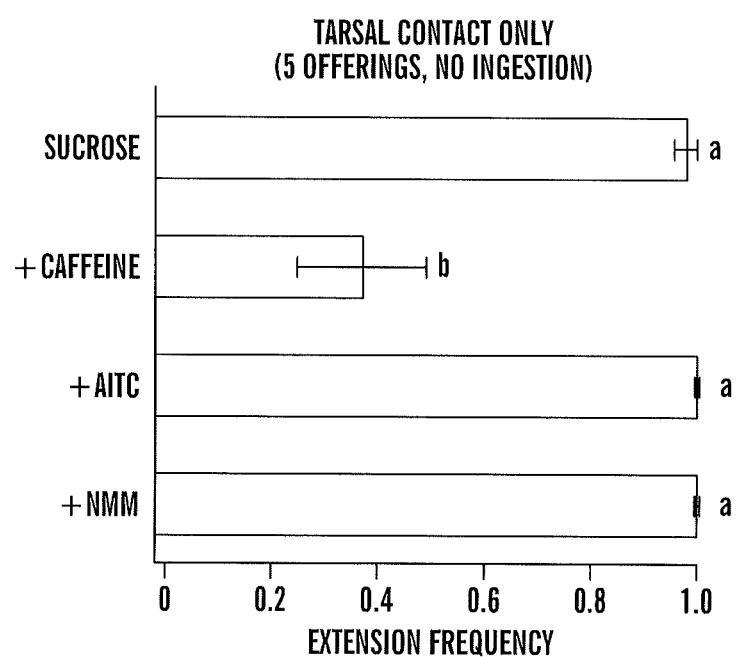

Reactive electrophiles are tissue-damaging agents that modify nucleic acids, proteins and other biomolecules. Reactive electrophiles are aversive to both vertebrates and invertebrates (Basbaum, et al., *Cell* 139, 267-284 (2009); Bessac, B. F. and S. E. Jordt, *Physiology (Bethesda)* 23, 360-370 (2008); and Eisner, T., in *Chemical Ecology*, edited by E. Sondheimer and J. B. Simeone (New York, 1970), Vol. Academic Press); plants and animals use them as deterrents (Eisner, T., in *Chemical Ecology*, edited by E. Sondheimer and J. B. Simeone (New York, 1970), Vol. Academic Press). Despite their importance as natural repellents, the cellular and molecular mechanisms by which reactive electrophiles deter insects have not been established. We examined *Drosophila* responses to reactive electrophiles using feeding. When a droplet of food (350 mM sucrose) contacts the legs of a hungry fly, the fly extends its proboscis to drink. This proboscis extension response (PER) is robust and sustained; >90% of the second through fifth offerings of food elicited PER (FIG. 1B). Adding the reactive electrophile allyl isothiocyanate (AITC, FIG. 1A) to the food dramatically inhibited this response (FIG. 1B). This effect was generalized to other reactive electrophiles using N-methyl maleimide (NMM) and cinnamaldehyde (CA) (FIG. 1A). Both NMM and CA robustly inhibited feeding (FIG. 1B). This inhibitory effect appeared gustatory, not olfactory, because NMM is non-volatile (m.p. 93° C.) and avoidance required ingestion. When only leg contact with food was permitted, reactive electrophiles did not affect PER (FIG. 1C), suggesting that chemosensors along the path of food intake rather than the legs mediate their inhibitory effects. The bitter compound caffeine, for which there are tarsal receptors (Thorne, et al., *Curr Biol* 14, 1065-1079 (2004) and Wang, et al., *Cell* 117, 981-991 (2004)), robustly inhibited PER even when ingestion was not permitted (FIG. 1C).

Figure 1D:
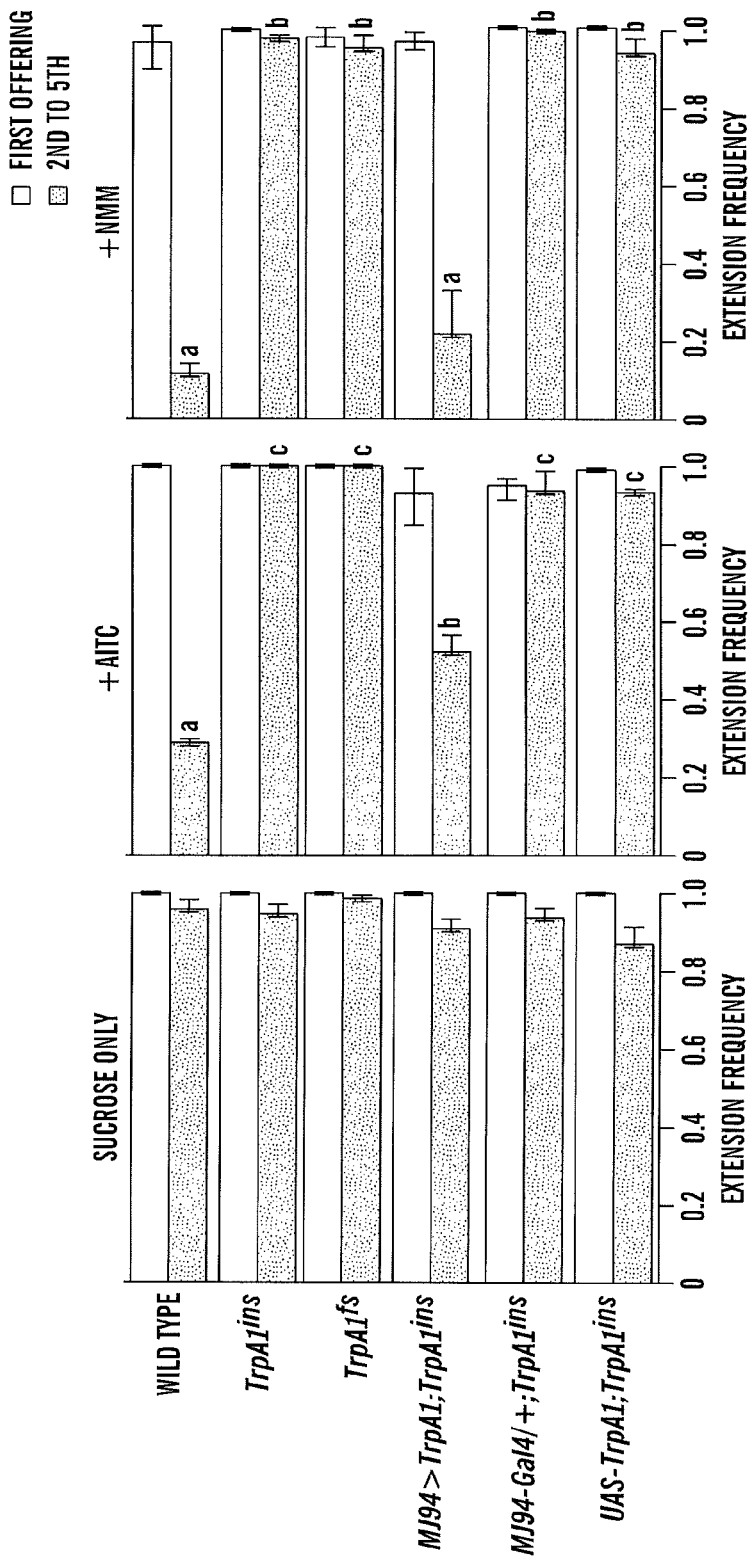
Figure 5:
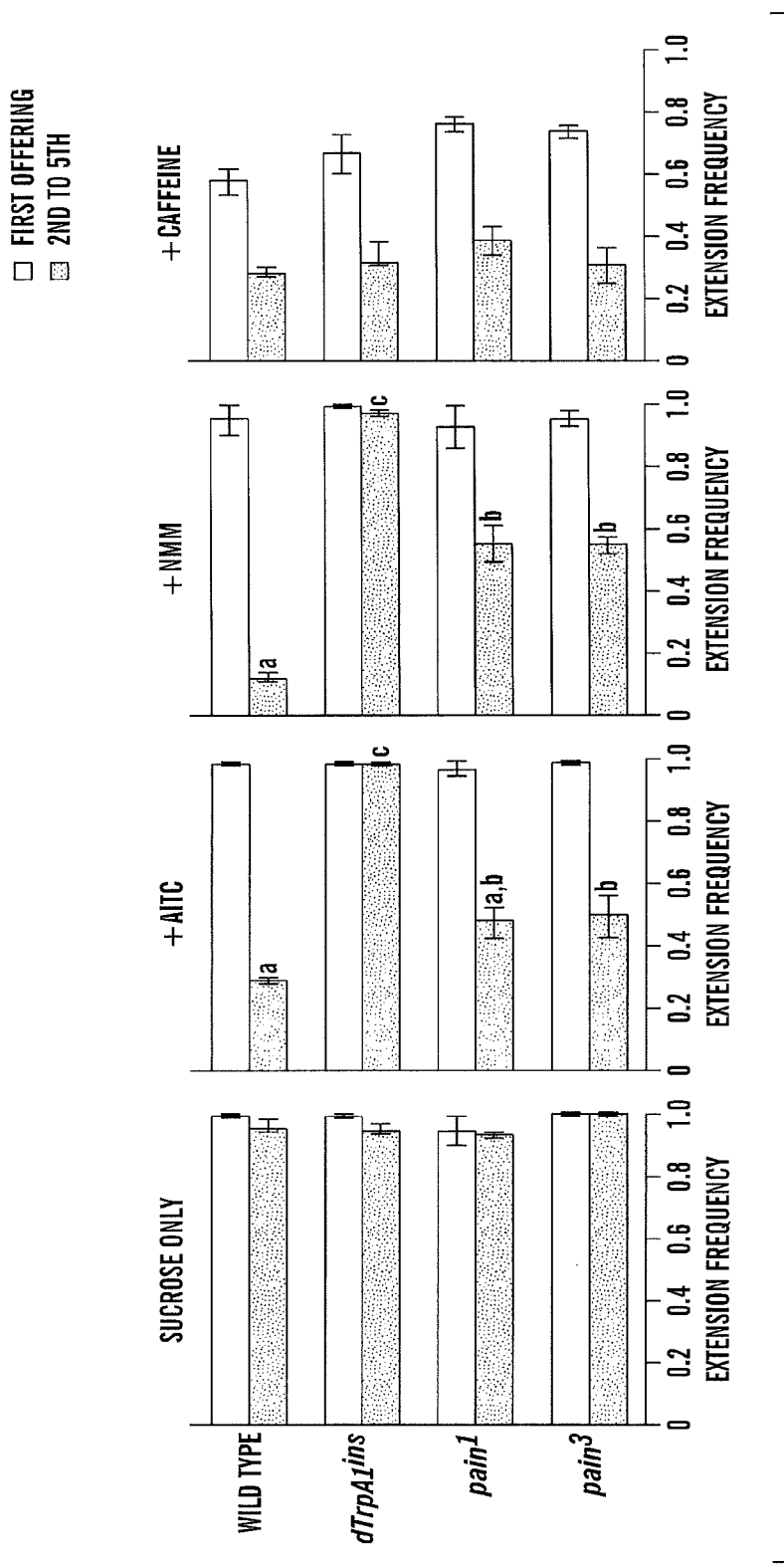
FIG. 5 depicts bar graph showing painless mutant responses to reactive electrophiles. PER responses, ingestion permitted. Upper bar (light blue), PER for first offering; lower bar (dark blue), PER for second to fifth offerings combined. AITC and NMM significantly inhibited PER responses in painless mutant flies, although the inhibitory effect was less than in wild type. Statistically distinct groups marked by different letters (Tukey HSD, $\alpha=0.05$ for +AITC, $\alpha=0.01$ for +NMM). n=3 groups of 7-8 flies. For each construct: upper bar (light), first offering; lower bar (dark), second to fifth offerings combined.
Figure 6A:
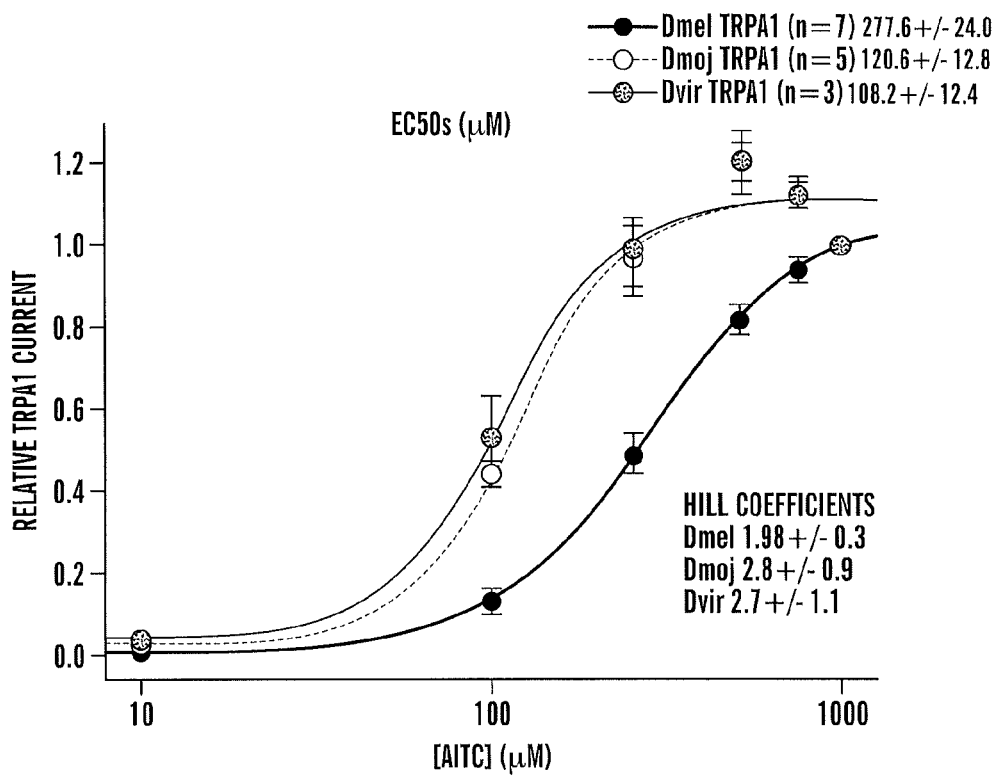
FIGS. 6A-6D show dose-response and dTRPA1-dependence of chemically activated currents in oocytes. AITC dose-response curves for dTRPA1 orthologs from *D. melanogaster*, *D. mojavensis* and *D. virilis* (FIG. 6A). Uninjected oocytes did not respond to reactive electrophiles when treated with 3 mM AITC (FIG. 6B), 1 mM CA (FIG. 6C) and 0.1 mM NMM (FIG. 6D).
Figure 6B:
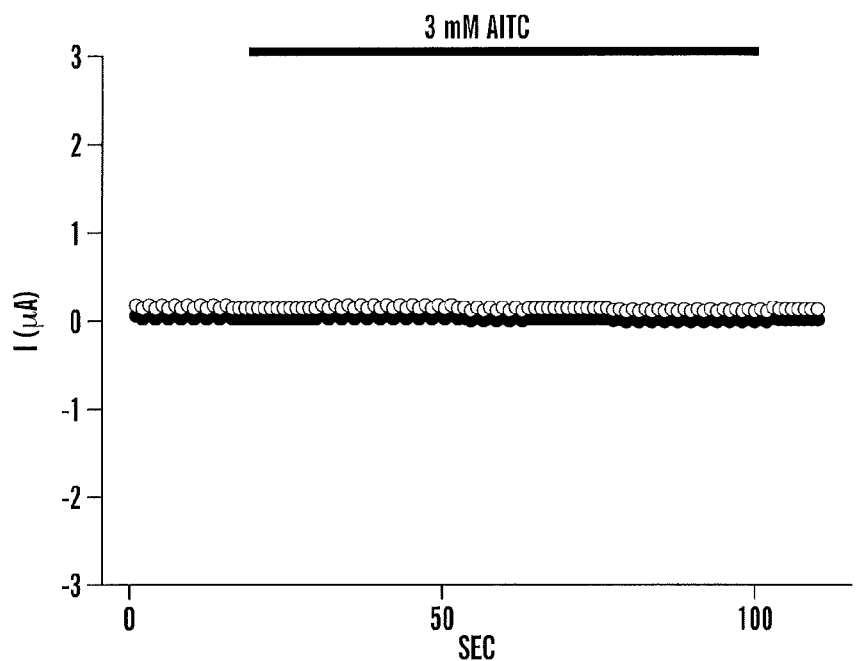
Figure 6C:
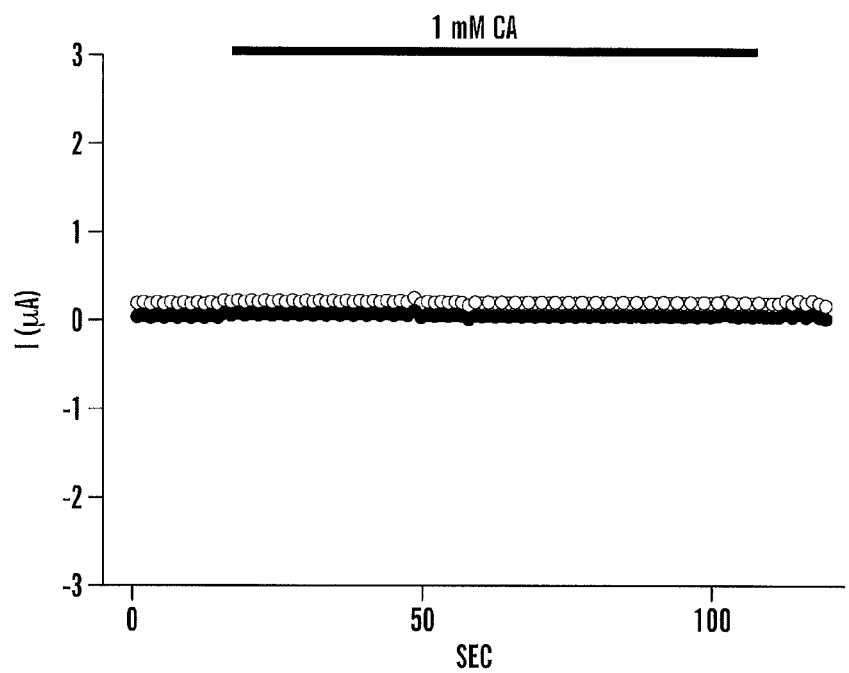
Figure 6D:
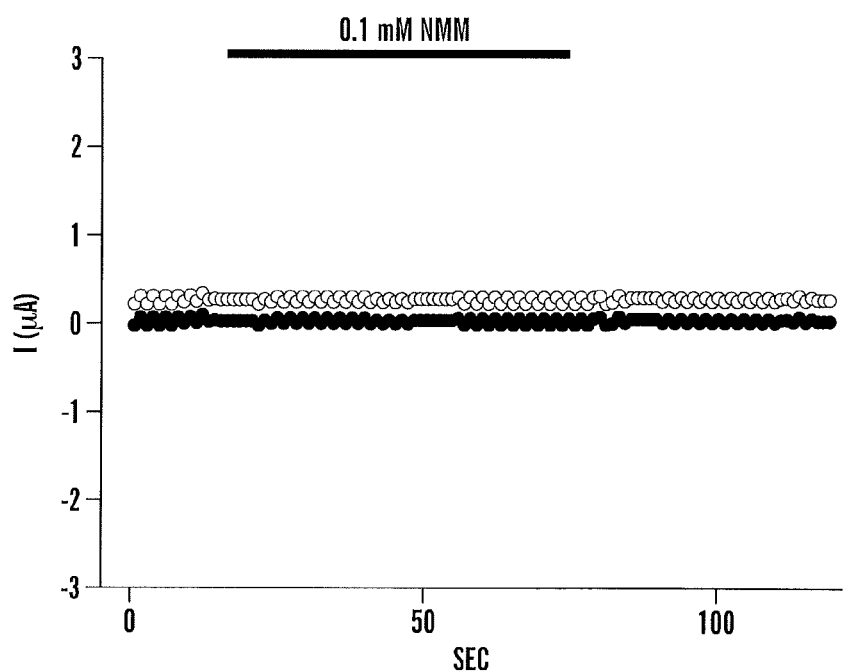
Figure 7A:
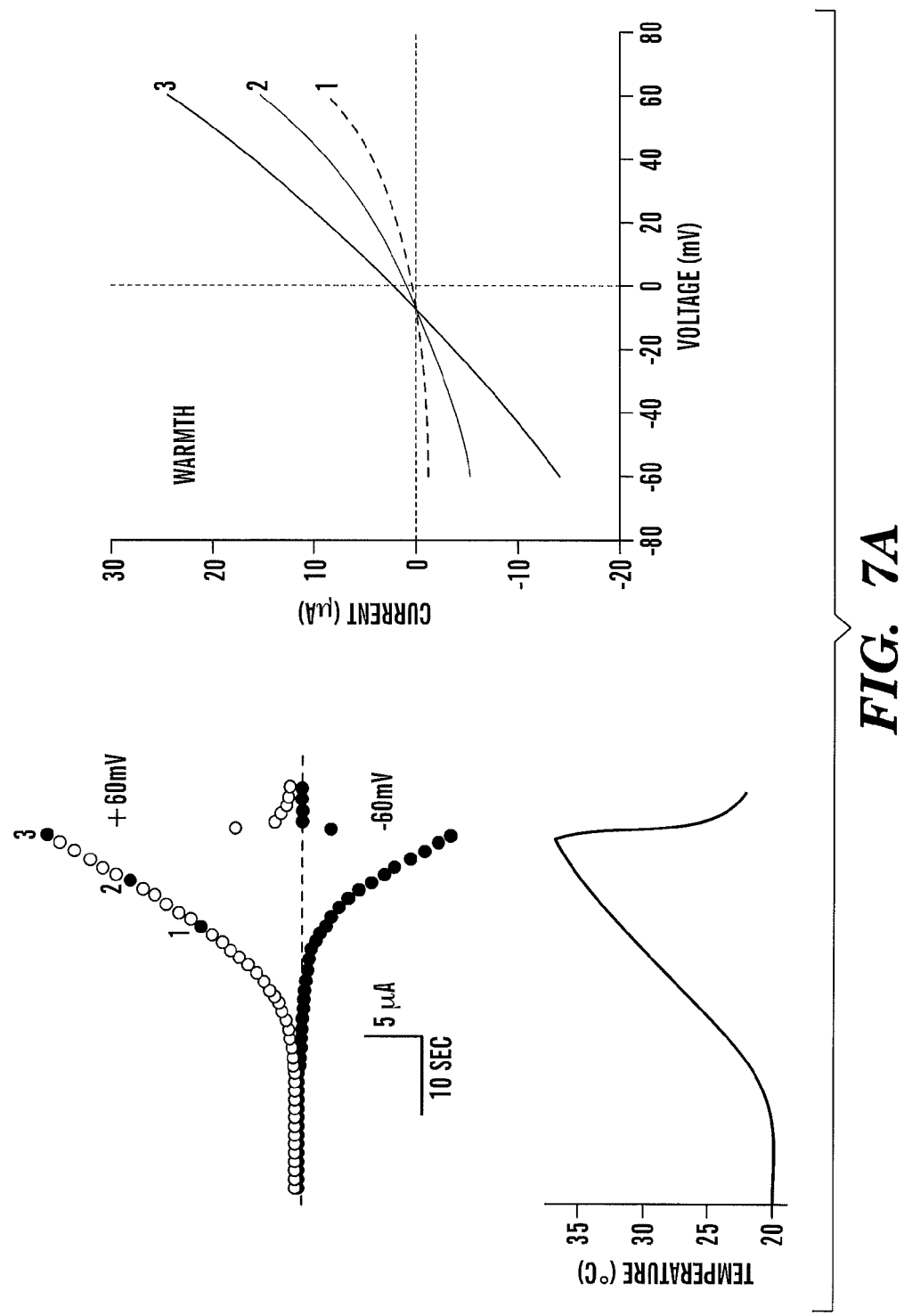
FIGS. 7A and 7B show that thermal and chemical activation of dTRPA1 yield currents with similar I-V properties. Warmth-activated dTRPA1 currents (left panel) and their I-V relationships (right panel) (FIG. 7A) and AITC-activated dTRPA1 currents (left panel) and their I-V relationships (right panel) (FIG. 7B). In both cases, the degree of outward rectification of the channel decreases as dTRPA1 is increasingly activated. Also note that while heat-activated currents decline rapidly upon cooling (FIG. 7A), chemically activated currents are more sustained (FIG. 7B), consistent with covalent modification of the channel by AITC.
Figure 7B:
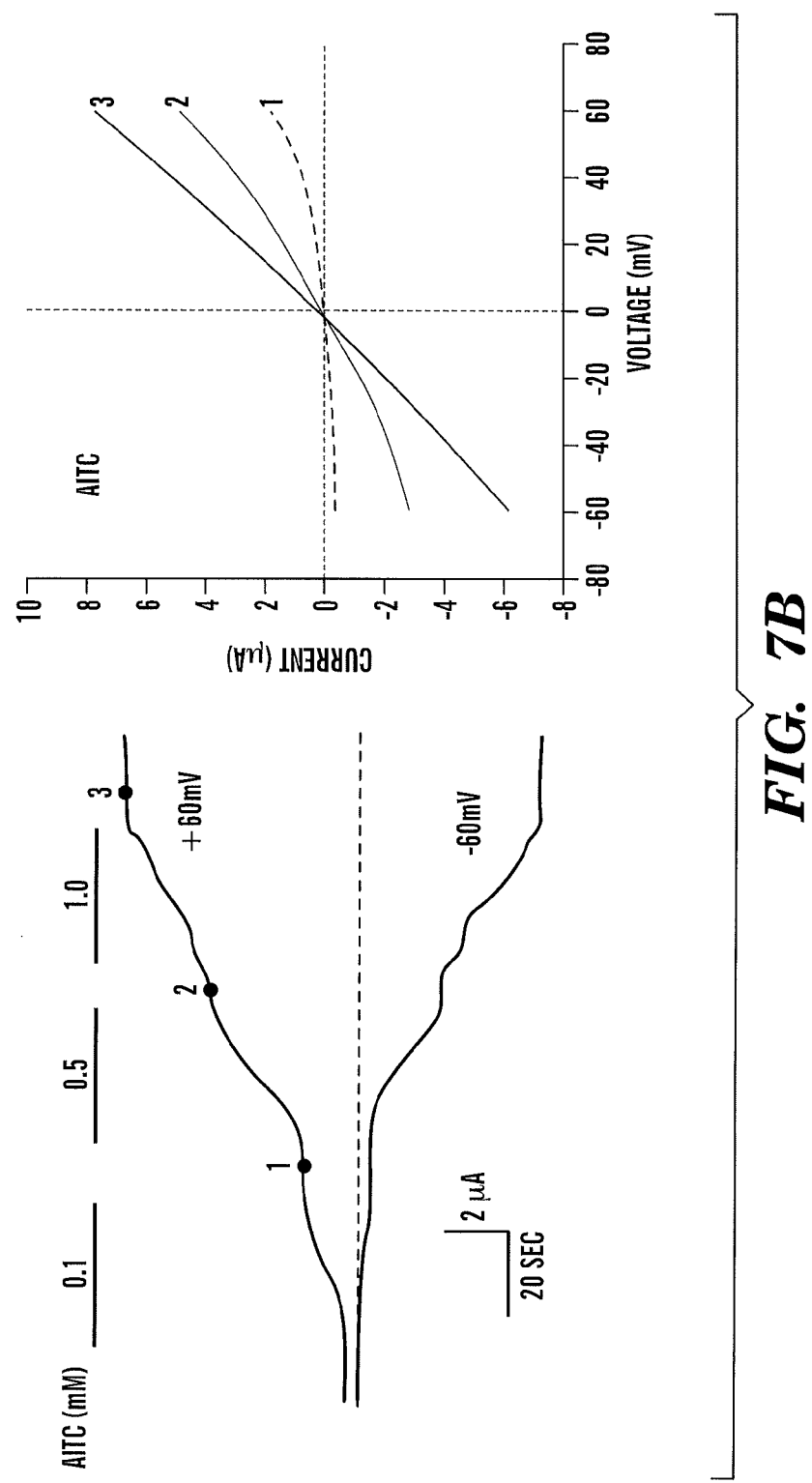

In vertebrates, the cation channel TRPA1 is a molecular receptor for reactive electrophiles, forming covalent adducts with these chemicals and activating sensory neurons to mediate irritation and pain. See for example, Bandell, et al., *Neuron* 41, 849-857 (2004); Jordt, et al., *Nature* 427, 260-265 (2004); Bautista, et al., *Cell* 124, 1269-1282 (2006); Kwan, et al., *Neuron* 50, 277-289 (2006); Hinman, et al., *Proc Natl Acad Sci USA* 103, 19564-19568 (2006); and Macpherson, et al., *Nature* 445, 541-545 (2007). Previous in vitro physiological analyses suggested that *Drosophila* TRPA1 relatives dTRPA1 and Painless were not activated by electrophiles (Bandell, et al., *Neuron* 41, 849-857 (2004) and Sokabe, et al., *J Neurosci* 28, 9929-9938 (2008)), raising the possibility that flies might use different mechanisms to detect these chemicals. We reexamined the possible involvement of dTRPA1 and Painless in vivo, assessing the gustatory response to reactive electrophiles. In contrast to wild type, dTrpA1 loss-of-function mutants showed no reduction in PER when offered food containing AITC, NMM, or CA (FIG. 1B). Similar defects were observed using two loss-of-function dTrpA1 alleles (dTrpA1$^{ins}$ and dTrpA1$^{fs}$) (Rosenzweig, M., K. Kang, and P. A. Garrity, *Proc Natl Acad Sci USA* 105, 14668-14673 (2008)) and dTrpA1 cDNA expression rescued this defect (FIG. 1D). Thus this response to reactive electrophiles is entirely TRPA1-dependent. dTrpA1 mutants responded to other deterrents, as caffeine inhibited PER (FIG. 1B). In contrast, painless mutants remained responsive to reactive electrophiles (FIG. 5), although responses were less robust than controls, suggesting a possible auxiliary function consistent with previous report (Al-Anzi, B., W. D. Tracey, Jr., and S. Benzer, *Curr Biol* 16, 1034-1040 (2006)).

dTRPA1 protein expression was detected in the mouthparts (data not shown), but not legs or labellum. Within the mouthparts, dTRPA1 was expressed in neurons innervating sensilla #8 and #9 of the labral sense organ (LSO) (data not shown). LSO sensilla contain pores that open onto the esophagus lumen, providing access to chemicals in ingested food. Thus, dTRPA1 is expressed in an appropriate place to mediate ingestion-dependent responses.

Figure 2A:
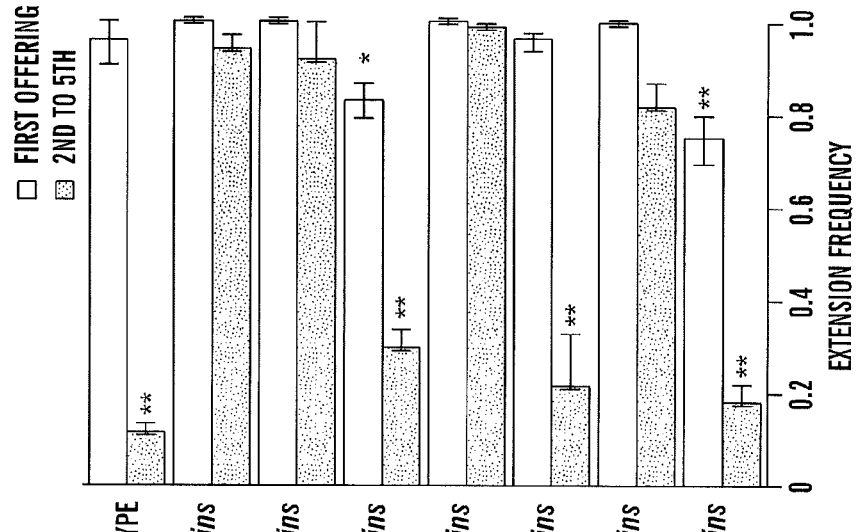
FIGS. 2A-2C are bar graph showing dTrpA1 functions in chemosensors. PER to 350 mM sucrose containing 10 mM NMM for dTRPA1 knockdown (FIG. 2A), dTRPA1 rescue (FIG. 2B), and dTRPA1 gain-of-function (FIG. 2C). Ingestion permitted (FIGS. 2A and 2B, n=3 groups of 7-8 flies) or tarsal contact only (FIG. 2C, n≥10 flies). (*: $\alpha=0.05$, **: $\alpha=0.01$, differ from Gal4 and UAS controls, Tukey HSD).
Figure 2B:
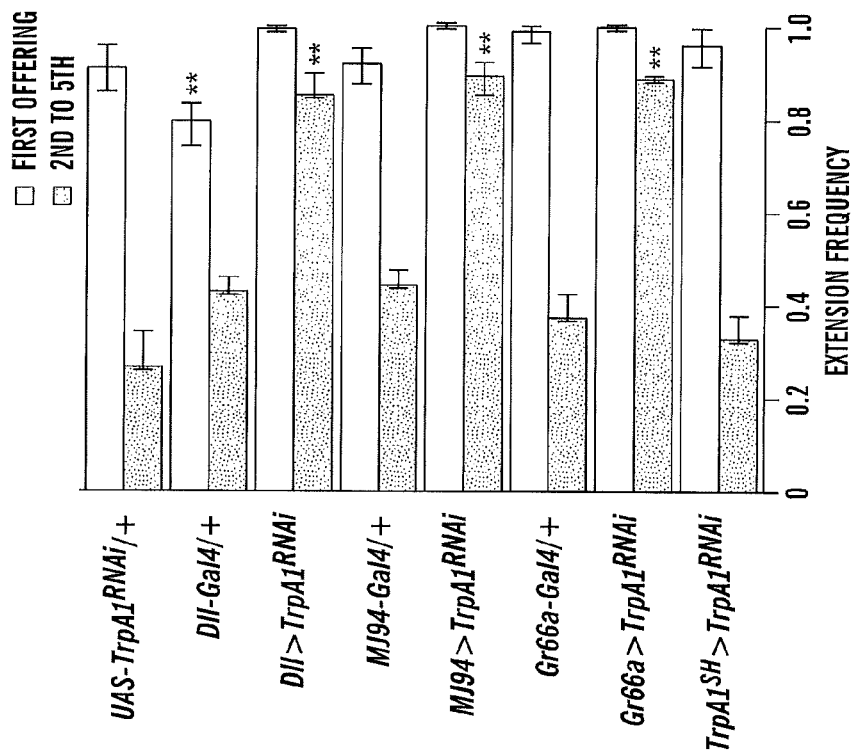
Figure 2C:
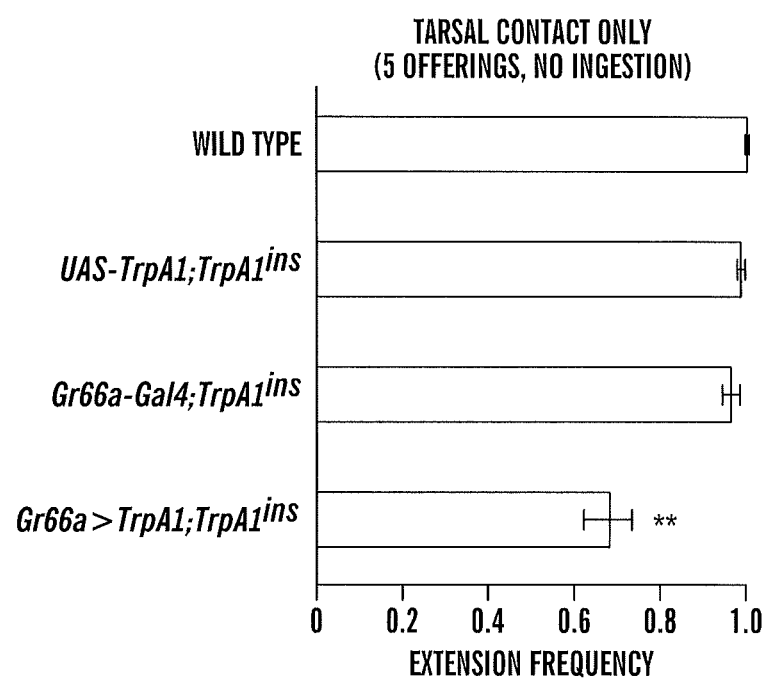
Figure 3A:
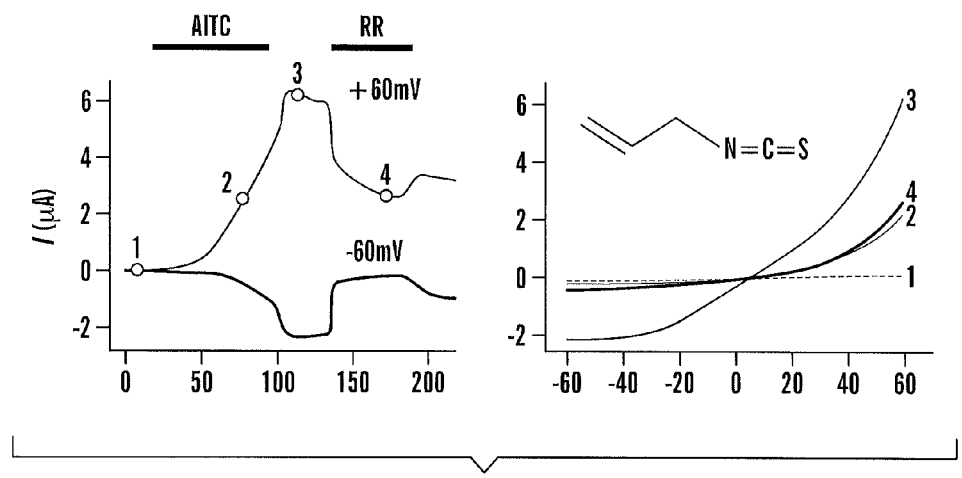
FIGS. 3A-3G show that insect TRPA1s are reactive electrophile sensors. Representative responses of dTRPA1 (FIGS. 3A-3D) and agTRPA1 (FIG. 3E) expressed in oocytes. Left panels, currents at −60 and +60 mV. Perfusion buffer containing indicated chemical at 100 µM (FIGS. 3A, 3C and 3D) or 40 µM (FIGS. 3B and 3E) was applied for 60-80 sec. 100 µM ruthenium red (RR) applied as noted. Right panels show I-V relationships at points marked on left panels.
Figure 3B:
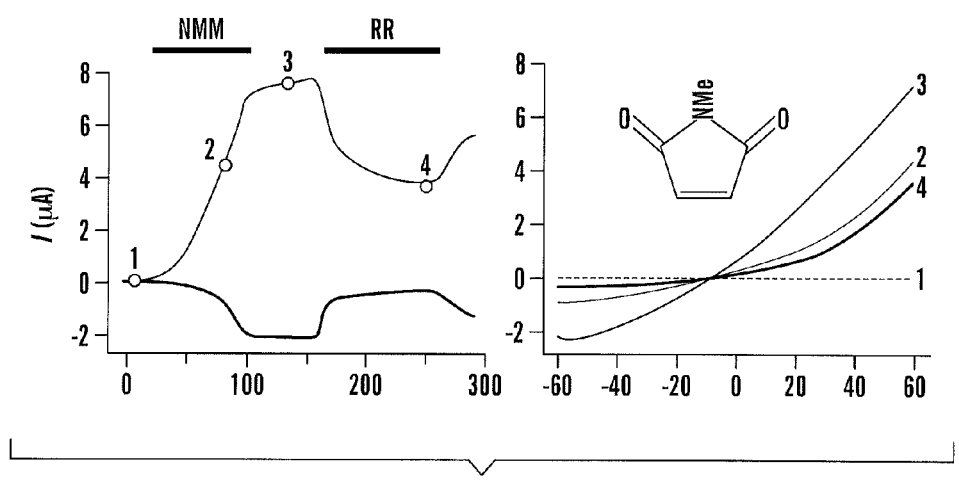
Figure 3C:
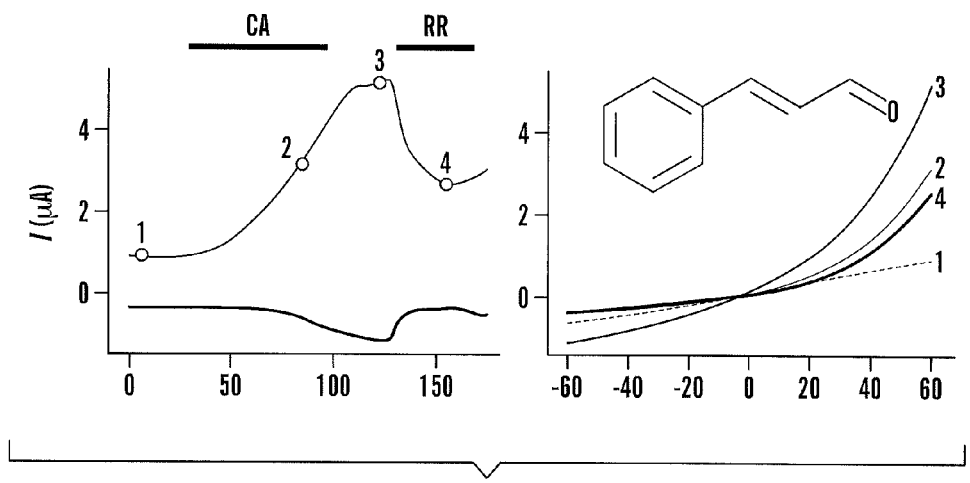
Figure 3D:
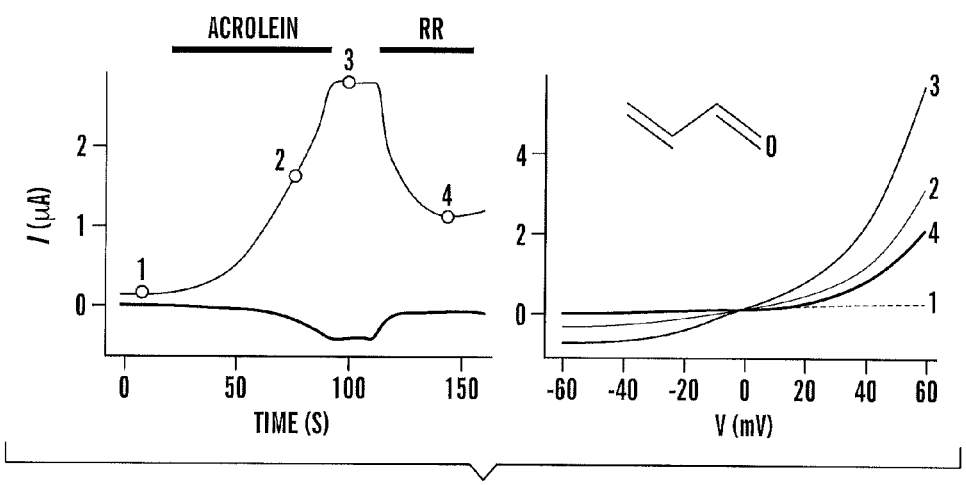
Figure 3E:
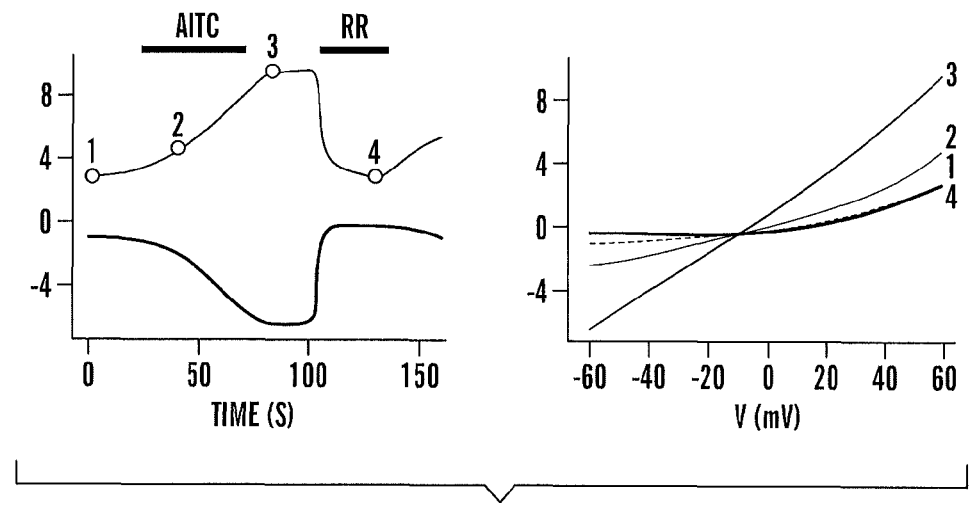
Figure 3F:
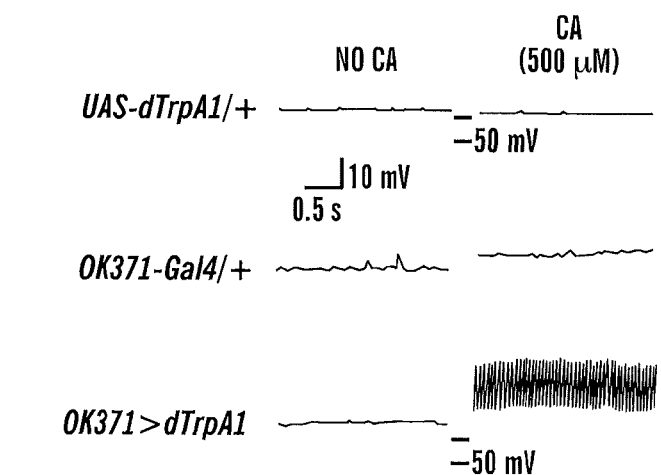
Figure 3G:
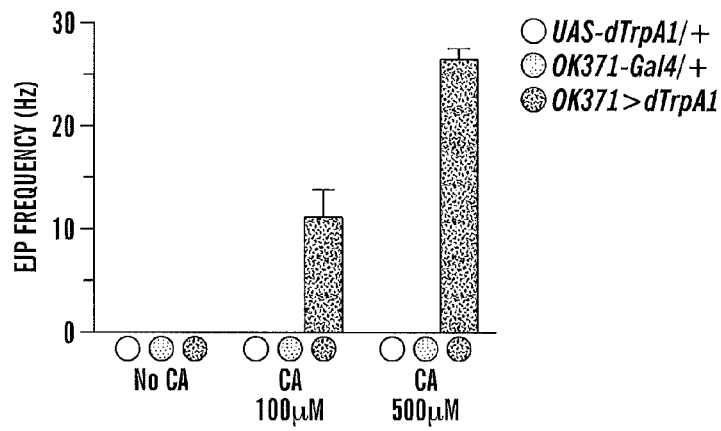
Figure 8:
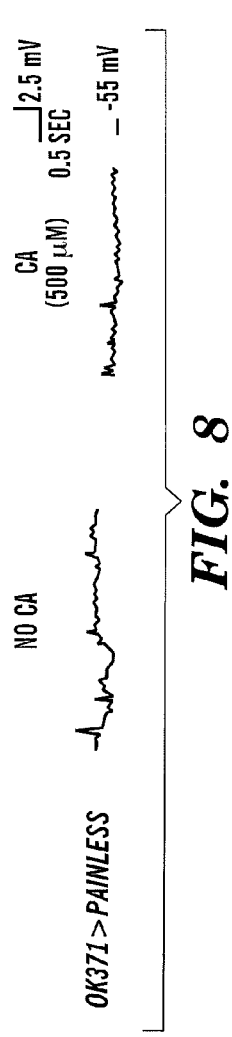
FIG. 8 shows that ectopic Painless expression does not confer pungent chemical sensitivity upon motor neurons. Intracellular recordings from third instar larval muscles of OK371>Painless animals before and during treatment with 500 µM cinnamaldehyde (CA). CA application does not induce excitatory junctional potentials (EJPs).

To test the significance of peripheral dTRPA1 expression, tissue-specific RNAi was performed using three promoters whose expression overlaps dTRPA1-positive LSO neurons: Dll-Gal4, expressed broadly within peripheral tissue, MJ94-Gal4, expressed in chemoreceptors and the brain (Gendre, et al., *Development* 131, 83-92 (2004)), and Gr66a-Gal4, expressed in chemoreceptors implicated in aversive responses (Thorne, et al., *Curr Biol* 14, 1065-1079 (2004) and Wang, et al., *Cell* 117, 981-991 (2004)) (data not shown). dTRPA1 knockdown using each promoter robustly reduced NMM's effect on PER, consistent with a requirement for dTRPA1 in peripheral chemoreceptors (FIG. 2A). In contrast, dTRPA1 knockdown in the AC thermosensory neurons of the head using dTrpA1$^{SH}$-Gal4 (Hamada, et al., *Nature* 454, 217-220 (2008)) had no effect (FIG. 2A). These data cleanly distinguish the sites of action for dTRPA1 in thermotaxis and gustation, with the former involving AC neurons (Hamada, et al., *Nature* 454, 217-220 (2008)) and the latter peripheral sensory neurons.

dTRPA1 expression in peripheral chemosensors also sufficed to induce reactive electrophile-dependent PER inhibition. dTRPA1 cDNA expression with Dll-Gal4, MJ94-Gal4, or Gr66a-Gal4 rescued the mutant phenotype (FIG. 2B). In addition, ectopic expression of dTRPA1 in leg chemoreceptors (using Gr66a-Gal4) allowed flies to respond to electrophiles via leg contact (FIG. 2C). Thus, dTRPA1 expression in peripheral chemosensory neurons is both necessary and sufficient for reactive electrophile-induced feeding inhibition.

dTRPA1 has been considered unresponsive to electrophiles (Bandell, M. et al., *Neuron* 41, 849-857 (2004) and Xiao, B., et al., *J Neurosci* 28, 9640-9651 (2008)); however, the inventors recently found that the original dTRPA1 cDNA contained a partially inactivating mutation (Hamada, et al., *Nature* 454, 217-220 (2008)). Using wild-type dTRPA1, the inventors discovered dTRPA1 was activated by multiple reactive electrophiles when expressed in *Xenopus* oocytes (FIGS. 3A-3D, 6 and 7). dTRPA1 orthologs from two other *Drosophila* species, *D. mojavensis* and *D. virilis*, and the malaria mosquito *Anopheles gambiae* also responded to these chemicals (FIGS. 3E and 6). Combined with the sensitivity of mosquito TRPA1 to AITC in HEK cells, as described in Xiao, B., et al., *J Neurosci* 28, 9640-9651 (2008), these findings demonstrate multiple insect TRPA1s respond to electrophiles. Notably, electrophile-activated currents persisted after chemical withdrawal (FIGS. 3A-3F), contrasting with the transient activation of dTRPA1 by warmth (Hamada, et al., *Nature* 454, 217-220 (2008)). Persistent activation by electrophiles has been observed for mammalian TRPA1s, and it is thought to reflect covalent association between agonists and channel. See, for example, Hinman, A., et al., *Proc Natl Acad Sci USA* 103, 19564-19568 (2006) and Macpherson, L. J., et al., *Nature* 445, 541-545 (2007). This similarity suggested reactive electrophiles might activate insect and mammalian TRPA1s via similar mechanisms. Finally, we demonstrated that ectopic expression of dTRPA1 in fly neurons can confer physiological sensitivity to electrophiles. In contrast to controls or motorneurons expressing Painless, dTRPA1-expressing motorneurons were cinnamaldehyde-responsive (FIGS. 3F and 8). Thus, dTRPA1 acts as an electrophile sensor in multiple contexts.

Figure 4B:
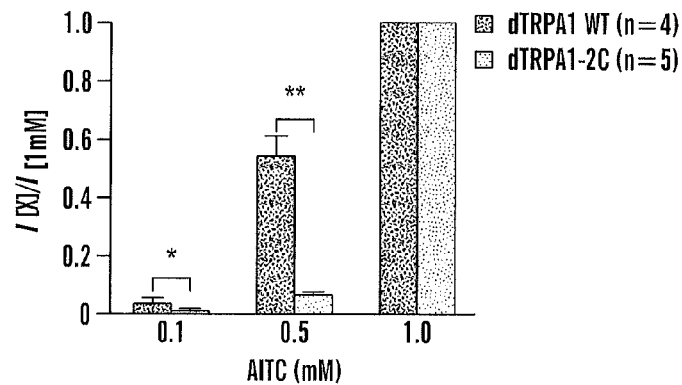
FIG. 4B depicts a bar graph showing +60 mV currents normalized to channel's response to 1.0 mM AITC. $*p<0.05$, $**p<0.001$, unpaired t-test.
Figure 9A:
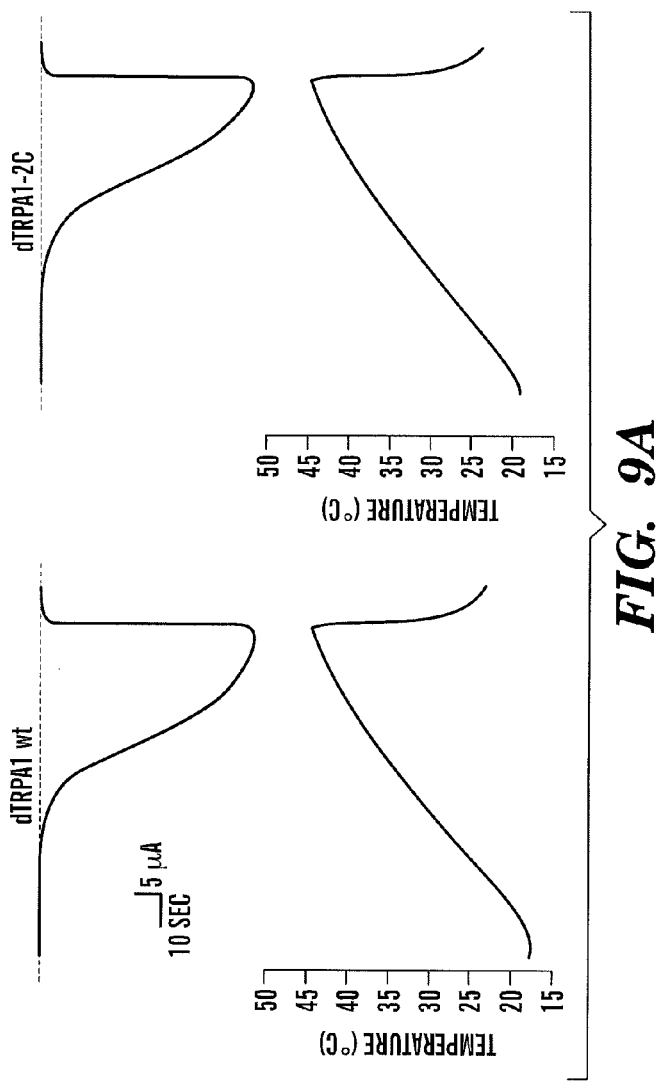
FIGS. 9A and 9B show that warming robustly activates dTRPA1-2C. Representative warmth-evoked currents in oocytes expressing wild type (dTRPA1 wt) and mutant (dTRPA1-2C) TRPA1 channels. Peak amplitude of warmth-evoked currents (FIG. 9B). Differences in peak amplitude did not reach statistical significance.
Figure 9B:
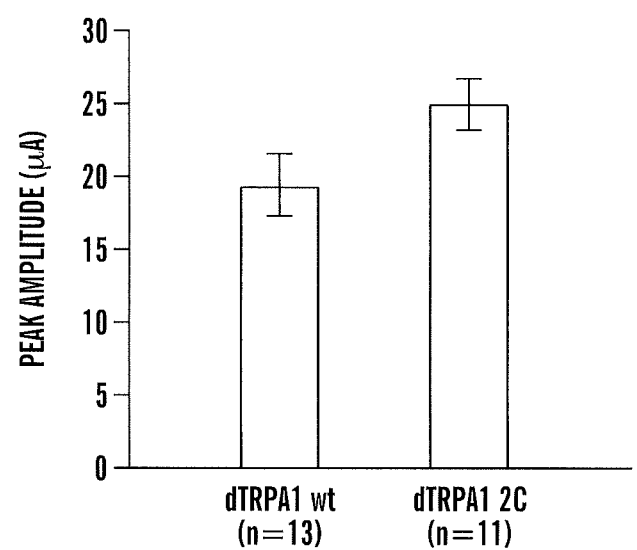
Figure 10B:
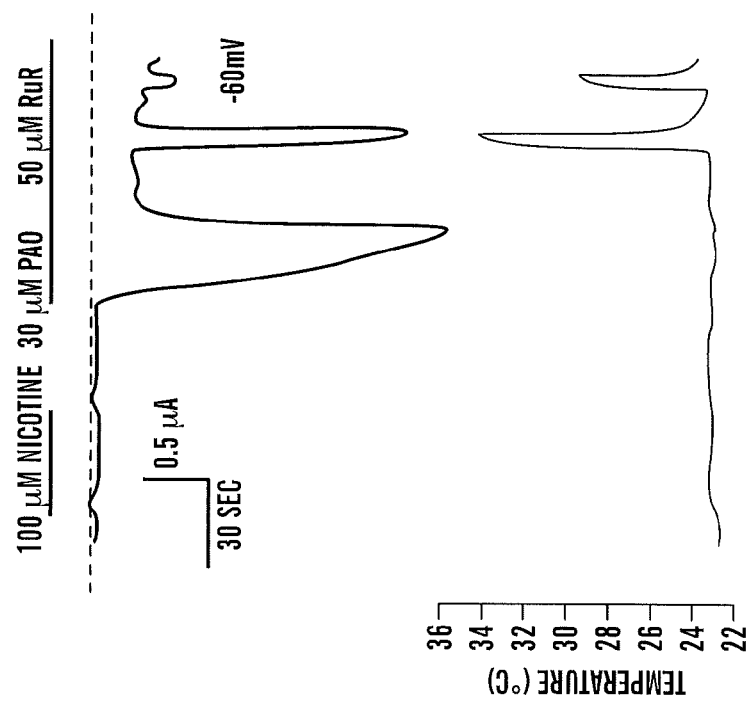
FIGS. 10A and 10B show that dTRPA1 did not detectably respond to 2-APB or nicotine. dTRPA1 expressing oocytes did not respond to treatment with 100 µM 2-APB (FIG. 10A) or nicotine (FIG. 10B). Subsequent activation of dTRPA1 by heat (FIG. 10A) and/or the cysteine-modifying reagent phenylarsine oxide (PAO, 30 µM) (FIG. 10B) was used to confirm that the oocytes expressed functional dTRPA1 channels.
Figure 10A:
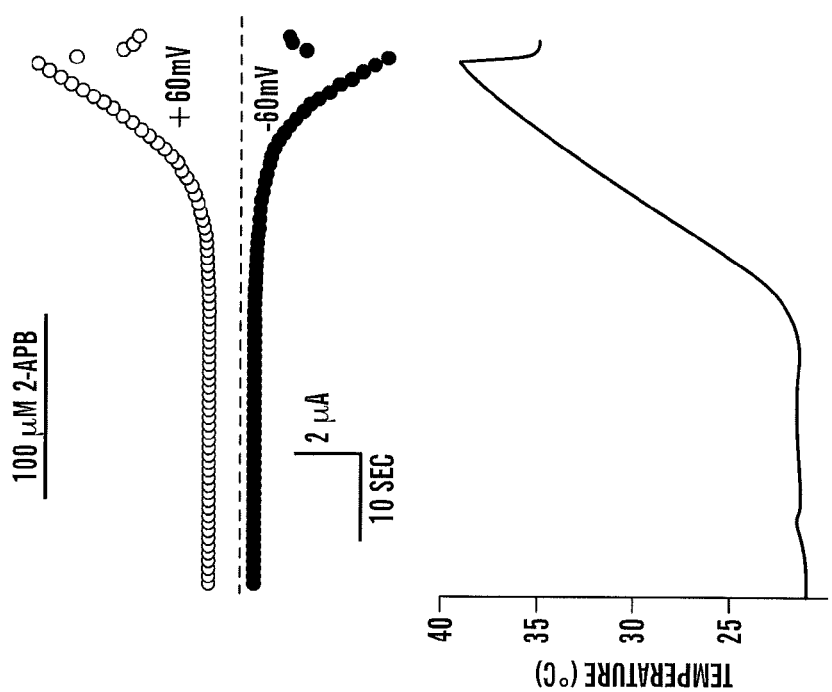

Reactive electrophiles activate mammalian TRPA1s by forming covalent bonds with cysteine and lysine residues in the channel; six residues (five cysteines and one lysine) are implicated in electrophile detection and mutations in these residues decrease electrophile sensitivity. See, for example, Hinman, A., et al., *Proc Natl Acad Sci USA* 103, 19564-19568 (2006) and Macpherson, L. J., et al., *Nature* 445, 541-545 (2007). Insect TRPA1s conserve five of these six residues (data not shown). Mutating dTRPA1 cysteines 650 and 670 to serines (dTRPA1-2C) significantly decreased AITC sensitivity (FIGS. 4A and 4B); this dTRPA1-2C mutant remained robustly warmth-activated (FIG. 9). The shared requirement for these residues further supports a common mechanism for reactive electrophile sensing by fly and vertebrate TRPA1s. TRPA1s also exhibit some species-specific differences in chemical sensitivity; 2-aminoethoxydiphenyl borate (2-APB) and nicotine, conserved cysteine-independent agonists of mammalian TRPA1s (Hinman, A., et al., *Proc Natl Acad Sci USA* 103, 19564-19568 (2006) and Talavera, K. et al., Nicotine activates the chemosensory cation channel TRPA1. *Nat Neurosci* 12, 1293-1299 (2009)), did not activate dTRPA1 (FIG. 10).

While functional similarities between insect and vertebrate TRPA1s could reflect conservation of an ancestral mechanism for electrophile detection, the electrophile insensitivity of invertebrate TRPA1 relatives like Painless (Sokabe, T., et al., *J Neurosci* 28, 9929-9938 (2008)) and *C. elegans* TRPA1 (ceTRPA1) (Kindt, K. S., et al., *Nat Neurosci* 10, 568-577 (2007)) raised the possibility that some insect and vertebrate TRPA1s recently converged on similar mechanisms. To test these alternatives, a phylogeny of TRPA proteins was constructed using three different approaches, Bayesian inference (Ronquist, F. and J. P. Huelsenbeck, *Bioinformatics* 19, 1572-1574 (2003)), maximum likelihood (Guindon, S., et al., *Methods Mol Biol* 537, 113-137 (2009)), and neighbor joining (Saitou, N. and M. Nei, *Mol Biol Evol* 4, 406-425 (1987)).

Trees were rooted using TRPAs from the unicellular choanoflagellate *M. brevicollis*. All methods indicated with high confidence that the electrophile-activated TRPA1 channels of invertebrates and vertebrates belong to a monophyletic clade, the TRPA1 clade, distinct from other TRPAs (termed basal TRPAs) by both tree topology and branch lengths (data not shown). The TRPA1 clade channels derive from a common ancestral TRPA1 present in the common ancestor of vertebrates and invertebrates (data not shown). Consistent with a common evolutionary origin of electrophile detection, sequence reconstruction (Yang, Z., *Mol Biol Evol* 24, 1586-1591 (2007)) suggested this ancestral TRPA1 contained all six critical residues associated with electrophile sensing. PAML residue identity estimates for ancestral TRPA1 were calculated to be 99.9% for cysteine at position 445, 79% for cysteine at position 452, 99.8% for cysteine at position 650, 100% for cysteine at position 670, 98.9% for cysteine at position 694, and 100% for lysine at position 744. This mode of electrophile detection appears specific to TRPA1 clade members, as no known basal TRPAs conserve more than one of the five cysteines implicated in electrophile detection (data not shown).

These analyses also suggest revisions to proposed relationships among TRPAs. Painless has been called the fly homolog of mammalian TRPA1, and ceTRPA1 considered the nematode TRPA1 ortholog. However, all analyses indicated that neither Painless nor ceTRPA1 descend from the ancestral TRPA1; both are closer to anemone and choanoflagellate TRPAs (data not shown). Consistent with their electrophile insensitivity (Sokabe, T., et al., *J Neurosci* 28, 9929-9938 (2008) and Kindt, K. S., et al., *Nat Neurosci* 10, 568-577 (2007)), Painless and ceTRPA1 lack most cysteines implicated in electrophile detection (data not shown). During evolution, nematodes appear to have lost their TRPA1 ortholog and vertebrates their basal TRPA(s) (data not shown).

Functional conservation of TRPA1 provides a simple molecular foundation for the widespread aversion to reactive electrophiles across the animal kingdom. The conservation of reactive electrophile detection differs from other chemical senses like olfaction and gustation whose origins are molecularly diverse and evolutionarily distinct. See for example, Bargmann, C. I., *Nature* 444, 295-301 (2006) and Nakagawa, T. and L. B. Vosshall, *Curr Opin Neurobiol* 19, 284-292 (2009). For example, many fly olfactory receptors are ion channels rather than the G-protein coupled receptors of vertebrates. See Nakagawa, T. and L. B. Vosshall, *Curr Opin Neurobiol* 19, 284-292 (2009). Reactive electrophile detection also contrasts with capsaicin detection; capsaicin activates mammalian nociceptors (Basbaum, A. I., et al., *Cell* 139, 267-284 (2009)), but elicits no acute response in flies or nematodes. The exceptional conservation of TRPA1-mediated nociception could relate to the toxicity of reactive electrophiles (Gomes R, Meek M E, and Eggleton M, *Concise International Chemical Assessment Document No 43*. (World Health Organization, Geneva, (2002)), which could provide selective pressure for maintaining an effective monitoring system.

dTRPA1's ability to mediate aversive responses to natural deterrents suggests insect TRPA1s as targets for developing new deterrents. Insect TRPA1 agonists can be useful against an array of pests, as disease vectors from mosquitoes to lice and agricultural pests from flour beetles to aphids (Hamada, F. N., et al., *Nature* 454, 217-220 (2008)) contain dTRPA1 relatives. The invention provides methods of identifying insect specific TRPA1 modulators. Such selective insect TRPA1 modulators can maximize pest deterrence while minimizing irritation to other animals.

REFERENCES

1. Basbaum, A. I., D. M. Bautista, G. Scherrer, and D. Julius, Cellular and molecular mechanisms of pain. Cell 139, 267-284 (2009).
2. Bessac, B. F. and S. E. Jordt, Breathtaking TRP Channels: TRPA1 and TRPV1 in Airway Chemosensation and Reflex Control. Physiology (Bethesda) 23, 360-370 (2008).
3. Eisner, T., in Chemical Ecology, edited by E. Sondheimer and J. B. Simeone (New York, 1970), Vol. Academic Press.
4. Thorne, N., C. Chromey, S. Bray, and H. Amrein, Taste perception and coding in *Drosophila*. Curr Biol 14, 1065-1079 (2004).
5. Wang, Z., A. Singhvi, P. Kong, and K. Scott, Taste representations in the *Drosophila* brain. Cell 117, 981-991 (2004).
6. Bandell, M. et al., Noxious cold ion channel TRPA1 is activated by pungent compounds and bradykinin. Neuron 41, 849-857 (2004).
7. Jordt, S. E. et al., Mustard oils and cannabinoids excite sensory nerve fibres through the TRP channel ANKTM1. Nature 427, 260-265 (2004).
8. Bautista, D. M. et al., TRPA1 mediates the inflammatory actions of environmental irritants and proalgesic agents. Cell 124, 1269-1282 (2006).
9. Kwan, K. Y., A. J. Allchorne, M. A. Vollrath, A. P. Christensen, D. S. Zhang, C. J. Woolf, and D. P. Corey, TRPA1 contributes to cold, mechanical, and chemical nociception but is not essential for hair-cell transduction. Neuron 50, 277-289 (2006).
10. Hinman, A., H. H. Chuang, D. M. Bautista, and D. Julius, TRP channel activation by reversible covalent modification. Proc Natl Acad Sci USA 103, 19564-19568 (2006).
11. Macpherson, L. J., A. E. Dubin, M. J. Evans, F. Marr, P. G. Schultz, B. F. Cravat, and A. Patapoutian, Noxious compounds activate TRPA1 ion channels through covalent modification of cysteines. Nature 445, 541-545 (2007).
12. Sokabe, T., S. Tsujiuchi, T. Kadowaki, and M. Tominaga, *Drosophila* painless is a Ca2+-requiring channel activated by noxious heat. J Neurosci 28, 9929-9938 (2008).
13. Rosenzweig, M., K. Kang, and P. A. Garrity, Distinct TRP channels are required for warm and cool avoidance in *Drosophila melanogaster*. Proc Natl Acad Sci USA 105, 14668-14673 (2008).
14. Al-Anzi, B., W. D. Tracey, Jr., and S. Benzer, Response of *Drosophila* to wasabi is mediated by painless, the fly homolog of mammalian TRPA1/ANKTM1. Curr Biol 16, 1034-1040 (2006).
15. Hamada, F. N., M. Rosenzweig, K. Kang, S. R. Pulver, A. Ghezzi, T. J. Jegla, and P. A. Garrity, An internal thermal sensor controlling temperature preference in *Drosophila*. Nature 454, 217-220 (2008).
16. Gendre, N., K. Luer, S. Friche, N. Grillenzoni, A. Ramaekers, G. M. Technau, and R. F. Stocker, Integra- 17. Xiao, B., A. E. Dubin, B. Bursulaya, V. Viswanath, T. J. Jegla, and A. Patapoutian, Identification of transmembrane domain 5 as a critical molecular determinant of menthol sensitivity in mammalian TRPA1 channels. J Neurosci 28, 9640-9651 (2008).
18. Talavera, K. et al., Nicotine activates the chemosensory cation channel TRPA1. Nat Neurosci 12, 1293-1299 (2009).
19. Kindt, K. S., V. Viswanath, L. Macpherson, K. Quast, H. Hu, A. Patapoutian, and W. R. Schafer, Caenorhabditis elegans TRPA-1 functions in mechanosensation. Nat Neurosci 10, 568-577 (2007).
20. Ronquist, F. and J. P. Huelsenbeck, MrBayes 3: Bayesian phylogenetic inference under mixed models. Bioinformatics 19, 1572-1574 (2003).
21. Guindon, S., F. Delsuc, J. F. Dufayard, and O. Gascuel, Estimating maximum likelihood phylogenies with PhyML. Methods Mol Biol 537, 113-137 (2009).
22. Saitou, N. and M. Nei, The neighbor-joining method: a new method for reconstructing phylogenetic trees. Mol Biol Evol 4, 406-425 (1987).
23. Yang, Z., PAML 4: phylogenetic analysis by maximum likelihood. Mol Biol Evol 24, 1586-1591 (2007).
24. Bargmann, C. I., Comparative chemosensation from receptors to ecology. Nature 444, 295-301 (2006).
25. Nakagawa, T. and L. B. Vosshall, Controversy and consensus: noncanonical signaling mechanisms in the insect olfactory system. Curr Opin Neurobiol 19, 284-292 (2009).
26. Gomes R, Meek M E, and Eggleton M, Concise International Chemical Assessment Document No 43. (World Health Organization, Geneva, 2002).
27. Viswanath, V. et al., Opposite thermosensor in fruitfly and mouse. Nature 423, 822-823 (2003).
28. Pulver, S. R., S. L. Pashkovski, N. J. Hornstein, P. A. Garrity, and L. C. Griffith, Temporal dynamics of neuronal activation by Channelrhodopsin-2 and TRPA1 determine behavioral output in Drosophila larvae. J Neurophysiol 101, 3075-3088 (2009).
29. Do, C. B., M. S. Mahabhashyam, M. Brudno, and S. Batzoglou, ProbCons: Probabilistic consistency-based multiple sequence alignment. Genome Res 15, 330-340 (2005).
30. Swofford, D. L., Phylogenetic Analysis Using Parsimony (*and Other Methods). Version 4. (Sinauer Associates, Sunderland, Mass., 2003).
31. Rosenzweig, M., K. M. Brennan, T. D. Tayler, P. O. Phelps, A. Patapoutian, and P. A. Garrity, The Drosophila ortholog of vertebrate TRPA1 regulates thermotaxis. Genes Dev 19, 419-424 (2005).
32. Calleja, M., E. Moreno, S. Pelaz, and G. Morata, Visualization of gene expression in living adult Drosophila. Science 274, 252-255 (1996).
33. Joiner Ml, A. and L. C. Griffith, CaM kinase II and visual input modulate memory formation in the neuronal circuit controlling courtship conditioning. J Neurosci 17, 9384-9391 (1997).
34. Dunipace, L., S. Meister, C. McNealy, and H. Amrein, Spatially restricted expression of candidate taste receptors in the Drosophila gustatory system. Curr Biol 11, 822-835 (2001).
35. Tracey, W. D., Jr., R. I. Wilson, G. Laurent, and S. Benzer, painless, a Drosophila gene essential for nociception. Cell 113, 261-273 (2003).
36. Waterhouse, A. M., Procter, J. B., Martin, D. M. A., Clamp, M., and G. J. Barton, Jalview version 2: A multiple sequence alignment and analysis workbench. Bioinformatics 25, 1189-1191 (2009).
37. Livingstone, C. D. and G. J. Barton. Protein sequence alignments: a strategy for the hierarchical analysis of residue conservation. CABIOS 9, 745-756 (1993).
38. Le, S. Q. and O. Gascuel, An improved general amino acid replacement matrix. Mol Biol Evol 25, 1307-1320 (2008).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed:

1. A method of insect control, the method comprising contacting an insect in need of control with an effective amount of an insect-specific transient receptor potential ion channel A1 (TRPA1) modulator compound selected from allyl isothiocyanate (AITC) or N-methyl-maleimide (NMM).

2. The method of claim 1, wherein the compound is an inhibitor or activator of TRPA1 activity.

3. The method of claim 1, wherein the insect in need of control is selected from the group consisting of fleas, rat fleas, oriental rat fleas, flies, black flies, sand flies, mosquitoes, horse flies, deer flies, eye gnats, house flies, blow flies, flesh flies, tsetse flies, lice, human lice, true bugs, assassin bugs, kissing bugs, and any combinations thereof.

4. The method of claim 1, wherein the insect in need of control is a disease vector, a parasite, an agricultural pest, or a horticultural pest.

5. The method of claim 1, wherein compound is applied to a locus of the insects.

6. The method of claim 5, wherein said locus is a breeding locus or a feeding locus.

7. The method of claim 1, wherein the compound is formulated with a food source.

8. The method of claim 1, wherein the compound is formulated with sucrose.

9. The method of claim 1, wherein the compound modulates thermo- and/or chemo-sensing in the insect.

10. The method of claim 1, wherein the compound inhibits feeding of the insect in need of control.

* * * * *